(12) United States Patent
Rabinowitz et al.

(10) Patent No.: US 7,172,893 B2
(45) Date of Patent: Feb. 6, 2007

(54) VIRUS VECTORS AND METHODS OF MAKING AND ADMINISTERING THE SAME

(75) Inventors: Joseph E. Rabinowitz, Carrboro, NC (US); Richard Jude Samulski, Chapel Hill, NC (US); Weidong Xiao, Jenkintown, PA (US)

(73) Assignee: University of North Carolina at Chapel Hill, Chapel Hill, NC (US)

( * ) Notice: Subject to any disclaimer, the term of this patent is extended or adjusted under 35 U.S.C. 154(b) by 472 days.

(21) Appl. No.: 10/205,942

(22) Filed: Jul. 26, 2002

(65) Prior Publication Data
US 2003/0053990 A1  Mar. 20, 2003

Related U.S. Application Data

(62) Division of application No. 09/438,268, filed on Nov. 10, 1999, now Pat. No. 6,491,907.

(60) Provisional application No. 60/123,651, filed on Mar. 10, 1999, provisional application No. 60/107,840, filed on Nov. 10, 1998.

(51) Int. Cl.
| C12N 7/00 | (2006.01) |
| C12N 7/02 | (2006.01) |
| C12N 15/74 | (2006.01) |
| C12Q 1/70 | (2006.01) |
| A01N 63/00 | (2006.01) |

(52) U.S. Cl. ............... 435/235.1; 435/5; 435/239; 435/471; 424/93.1

(58) Field of Classification Search ............ 427/93.1, 427/93.2, 93.21, 93.3, 93.6; 435/235.1, 455; 536/23.1, 23.4
See application file for complete search history.

(56) References Cited

U.S. PATENT DOCUMENTS

| 5,139,941 A | 8/1992 | Muzyczka et al. ........ 435/172.3 |
| 5,436,146 A | 7/1995 | Shenk et al. .............. 435/172.3 |
| 5,478,745 A | 12/1995 | Samulski et al. ......... 435/320.1 |
| 5,589,377 A | 12/1996 | Lebkowski et al. |
| 5,622,856 A | 4/1997 | Natsoulis .................... 435/325 |
| 5,658,785 A | 8/1997 | Johnson ...................... 435/367 |
| 5,681,731 A | 10/1997 | Lebkowski et al. ...... 435/172.3 |
| 5,753,500 A | 5/1998 | Shenk et al. .............. 435/320.1 |
| 5,756,283 A | 5/1998 | Wilson et al. ................... 435/5 |
| 5,773,289 A | 6/1998 | Samulski et al. ......... 435/320.1 |
| 5,780,280 A | 7/1998 | Lebkowski et al. ...... 435/172.3 |
| 5,780,447 A | 7/1998 | Nienhuis ..................... 514/44 |
| 5,786,211 A | 7/1998 | Johnson ................... 435/320.1 |
| 5,834,441 A | 11/1998 | Philip et al. .................. 514/44 |
| 5,843,742 A | 12/1998 | Natsoulis et al. ......... 435/172.3 |
| 5,846,528 A | 12/1998 | Podsakoff et al. ......... 424/93.2 |
| 5,846,546 A | 12/1998 | Hurwitz et al. .......... 424/202.1 |
| 5,856,152 A | 1/1999 | Wilson et al. ............ 435/172.3 |
| 5,858,351 A | 1/1999 | Podsakoff et al. ......... 424/93.2 |
| 5,858,775 A | 1/1999 | Johnson ................... 435/320.1 |
| 5,861,171 A | 1/1999 | Philip et al. ................. 424/450 |
| 5,861,314 A | 1/1999 | Philip et al. .............. 424/372.3 |
| 5,863,541 A | 1/1999 | Samulski et al. ......... 424/192.1 |
| 5,866,552 A | 2/1999 | Wilson et al. ................. 514/44 |
| 5,866,696 A | 2/1999 | Carter et al. ............... 536/23.5 |
| 5,869,305 A | 2/1999 | Samulski et al. ......... 435/172.3 |
| 5,871,982 A | 2/1999 | Wilson et al. ........... 435/172.3 |
| 5,872,005 A | 2/1999 | Wang et al. ............. 435/320.1 |
| 5,874,304 A | 2/1999 | Zolotukhin et al. ......... 435/366 |
| 5,874,556 A | 2/1999 | Lupton et al. ............. 536/23.1 |
| 5,882,652 A | 3/1999 | Valdes et al. ............. 424/221.1 |
| 5,905,040 A | 5/1999 | Mazzara et al. ......... 435/320.1 |
| 5,916,563 A | 6/1999 | Young et al. ............. 424/192.1 |
| 5,922,315 A | 7/1999 | Roy .......................... 424/93.2 |
| 5,945,335 A | 8/1999 | Colosi ........................ 435/369 |
| 5,952,221 A | 9/1999 | Kurtzman et al. ....... 435/320.1 |
| 5,962,274 A | 10/1999 | Parks ........................ 435/91.1 |
| 5,962,313 A | 10/1999 | Podsakoff et al. ........ 435/320.1 |
| 6,001,371 A | 12/1999 | Young et al. ............. 424/233.1 |
| 6,156,303 A * | 12/2000 | Russell et al. ............. 424/93.2 |
| 6,468,524 B1 | 10/2002 | Chiorini et al. |
| 6,491,907 B1 * | 12/2002 | Rabinowitz et al. ....... 424/93.2 |
| 6,759,237 B1 | 7/2004 | Wilson et al. |
| 2004/0057931 A1 | 3/2004 | WIlson et al. |
| 2004/0057932 A1 | 3/2004 | Wilson et al. |
| 2004/0057933 A1 | 3/2004 | Wilson et al. |

FOREIGN PATENT DOCUMENTS

| AU | 199942205 | 6/2003 |
| WO | WO 95/28493 | 10/1995 |
| WO | WO 96/00587 | 1/1996 |
| WO | WO 96/36364 | 11/1996 |
| WO | WO 97/05266 | 2/1997 |
| WO | WO 97/38423 | 10/1997 |

(Continued)

OTHER PUBLICATIONS

Horiuchi et al. J Gen Virol. Jun. 1994; 75 (Pt 6):1319-28, Mapping of determinants of the host range for canine cells in the genome of canine parvovirus using canine parvovirus/mink enteritis virus chimeric viruses.*

(Continued)

*Primary Examiner*—Joseph Woitach
(74) *Attorney, Agent, or Firm*—Myers Bigel Sibley & Sajovec, PA

(57) ABSTRACT

The present invention provides genetically-engineered parvovirus capsids and viruses designed to introduce a heterologous gene into a target cell. The parvoviruses of the invention provide a repertoire of vectors with altered antigenic properties, packaging capabilities, and/or cellular tropisms as compared with current AAV vectors.

54 Claims, 7 Drawing Sheets

FOREIGN PATENT DOCUMENTS

| | | |
|---|---|---|
| WO | WO 98/09524 | 3/1998 |
| WO | WO 98/11244 | 3/1998 |
| WO | WO 98/32842 | 7/1998 |
| WO | WO 98/41240 | 9/1998 |
| WO | WO 99/61601 | 12/1999 |
| WO | WO 99/67393 | 12/1999 |
| WO | WO 00/28061 | 5/2000 |
| WO | WO 01/05991 | 1/2001 |
| WO | WO 01/05990 | 2/2001 |

OTHER PUBLICATIONS

Wang et al: J Virol. Mar. 1996; 70(3):1668-77. Rescue and replication of adeno-associated virus type 2 as well as vector DNA sequences from recombinant plasmids containing deletions in the viral inverted terminal repeats: selective encapsidation of viral gen.*

Srivastava et al. Proc. Natl Acad Sci U S A. Oct. 1989; 86(20):8078-82. Construction of a recombinant human parvovirus B19: adeno-associated virus 2 (AAV) DNA inverted terminal repeats are functional in a AAV-B19 hybrid virus.*

Bartlett et al. Viral Vectors, Chapter 4, pp. 55-73.*

Chapman et al. Virology (1993) 194:491-508.*

Brown et al. Virology (1994), 198:477-488.*

Rabinowitz et al., "Insertional Mutagenesis of AAV2 Capsid and the Production of Recombinant Virus," *Virology* 265:274-285 (1999).

Bloom et al., "Characterization of Chimeric Full-Length Molecular Clones of Aleutian Mink Disease Parvoviurs (ADV): Identification of a Determinant Governing Replication of ADV in Cell Culture," *Journal of Virology*: 5976-5988 (Oct. 1993).

Spitzer et al., "Tropic determinant for canine parvovirus and feline panleukopenia virus functions through the capsid protein VP2," *Journal of General Virology* 78: 925-928 (1997).

Xiao et al., "Gene Therapy Vectors Based on Adeno-Associated Virus Type 1," *Journal of Virology* 73(5): 3994-4003 (May 1999).

Anderson, "Human Gene Therapy," *Nature* 392: 25-30 (1998).

Antonietti et al.; "Characterization of the Cell Type-Specific Determinant in the Genome of Minute Virus of Mice," *Journal of Virology* 62:2 552-557 (Feb. 1988).

Ball-Goodrich et al.; Two Amino Acid Substitutions within the Capsid Are Coordinately Required for Acquisition of Fibrotropism by the Lymphotropic Strain of Minute Virus of Mice, *Journal of Virology* 66:6 3415-3423 (Jun. 1992).

Bartlett et al., "Genetics and Biology of Adeno-Associated Virus," *Viral Vectors* 55-73 (1995).

Bartlett et al.; Targeted adeno-associated virus vector transduction of nonpermissive cells mediated by a bispecific F(ab'γ)₂ antibody, *Nature Biotechnology* 17 181-191 (Feb. 1999).

Bloom et al.; Construction of Pathogenic Molecular Clones of Aleutian Mink Disease Parvovirus that Replicate Both *in Vivo* and *in Vitro*, *Virology* 251 288-296 (1998).

Brown et al.; Chimeric Parvovirus B19 Capsids for the Presentation of Foreign Epitopes, *Virology* 198 477-488 (1994).

Brown et al.; Erythrocyte P Antigen: Cellular Receptor for B19 Parvovirus, *Science* 262 114-117 (Oct. 1, 1993).

Chang et al.; Multiple Amino Acids in the Capsid Structure of Canine Parvovirus Coordinately Determine the Canine Host Range and Specific Antigenic and Hemagglutination Properties, *Journal of Virology* 66:12 6858-6867 (Dec. 1992).

Chapman et al.; *Structure, Sequence, and Function Correlation Among Parvoviruses*, Virology 194:491-508 (1993).

Chiorini et al.; Adeno-Associated Virus (AAV) Type 5 Rep Protein Cleaves a Unique Terminal Resolution Site Compared with Other AAV Serotypes, *Journal of Virology* 73:5 4293-4298 (May 1999).

Chiorini et al.; Cloning and Characterization of Adeno-Associated virus Type 5, *Journal of Virology* 73:2 1309-1319 (Feb. 1999).

Chiorini et al.; Cloning of Adeno-Associated Virus Type 4 (AAV4) and Generation of Recombinant AAV4 Particles, *Journal of Virology* 71:9 6823-6833 (Sep. 1997).

Fu et al., Viral sequences enable efficient and tissue-specific expression of transgenes in *Xenopus*, *Nature Biotechnology* 16 253-257 (Mar. 1998).

Gao et al.; *High-Titer Adeno-Associated Viral Vectors from a Rep/Cap Cell Line and Hybrid Shuttle Virus*, Human Gene Therapy 9:23253-2362 (Nov. 1, 1998).

Gardiner et al.; "Mapping of the Fibrotropic and Lymphotropic Host Range Determinants of the Parvovirus Minute Virus of Mice," *Journal of Virology* 62:8 2605-2613 (Aug. 1988).

Girod et al.; Genetic capsid modifications allow efficient re-targeting of adeno-associated virus type 2, *Nature Medicine* 5:9 1052-1056 (Sep. 1999).

Goldman et al.; Targeted Gene Delivery to Kaposi's Sarcoma Cells *via* the Fibroblast Growth Factor Receptor, *Cancer Research* 57 1447-1451 (Apr. 15, 1997).

Hermonat et al.; Genetics of Adeno-Associated Virus: Isolation and Preliminary Characterization of Adeno-Associated Virus Type 2 Mutants, *Journal of Virology* 51:2 329-339 (Aug. 1984).

Horiuchi et al.; *Mapping of Determinants of the Host Range for Canine Cells in the Genome of Canine Parvovirus Using Canine Parvovirus/Mink Enteritis Virus Chimeric Viruses*, Journal of General Virology 75:1319-1328 (1994).

International Search Report, PCT/US99/26505, Date of Mailing: Mar. 22, 2000.

Li et al.; Role for Highly Regulated *rep* Gene Expression in Adeno-Associated Virus Vector Production, *Journal of Virology* 71:7 5236-5243 (Jul. 1997).

Maxwwell et al.; Targeting a Feline Parvovirus to Human Tumor Cells (abstract), Cold Spring Harbor Laboratory, Vector Targeting Strategies for Therapeutic Gene Delivery meeting (Mar. 11-14, 1999) p. 87.

Miyamura et al.; Parvovirus particles as platforms for protein presentation, *Proc. Natl. Acad. Sci. USA* 91 8507-8511 (Aug. 1994).

Moskalenko et al.; Epitope Mapping of Human Anti-Adeno-Associated Virus Type 2 Neutralizing Antibodies: Implications for Gene Therapy and Virus Structure, *Journal of Virology* 74:4 1761-1766 (Feb. 2000).

Muralidhar et al.; Site-Directed Mutagenesis of Adeno-Associated Virus Type 2 Structural Protein Initiation Codons: Effects on Regulation of Synthesis and Biological Activity, *Journal of Virology* 68:1 170-176 (Jan. 1994).

Muramatsu et al.; Nucleotide Sequencing and Generation of an Infectious Clone of Adeno-Associated Virus 3, *Virology* 221 208-217 (1996).

Parrish et al.; "Canine Host Range and a Specific Epitope Map along with Variant Sequences in the Capsid Protein Gene of Canine Parvovirus and Related Feline, Mink, and Raccoon Parvoviruses," *Virology* 166:293-307 (1988).

Parrish et al.; "Rapid Antigeneic-Type Replacement and DNA Sequence Evolution of Canine Parvovirus," *Journal of Virology* 65:12 6544-6552 (Dec. 1991).

Ponnazhagan et al.; Recombinant Human Parvovirus B19 Vectors: Erythroid Cell-Specific Delivery and Expression of Transduced Genes, *Journal of Virology* 72:6 5224-5230 (Jun. 1998).

Rabinowitz et a.; *Adeno-Associated Virus Expression Systems for Gene Transfer*, Current Opinion in Biotechnology 9:5 470-475 (Oct. 1998).

Rabinowitz et al.; Targeted Adeno-Associated Virus (abstract), Cold Spring Harbor Laboratory, Vector Targeting Strategies for Therapeutic Gene Delivery meeting (Mar. 11-14, 1999) p. 82.

Ruffing et al.; Mutations in the carboxy terminus of adeno-associated virus 2 capsid proteins affect viral infectivity: lack of an RGD integrin-binding motif, *Journal of General Virology* 75 3385-3392 (1994).

Russell et al.; Retroviral vectors displaying functional antibody fragments, *Nucleic Acids Research* 21:5 1081-1085 (1993).

Rutledge et al.; Infectious Clones and Vectors Derived from Adeno-Associated Virus (AAV) Serotypes Other Than AAV Type 2, *Journal of Virology* 72:1 309-319 (Jan. 1998).

Sedlik et al.; Recombinant parvovirus-like particles as an antigen carrier: A novel nonreplicative exogenous antigen to elicit protective antiviral cytotoxic T cells, *Proc. Natl. Acad. Sci. USA* 97 7503-7508 (Jul. 1997).

Smuda et al.; Adeno-Associated Viruses Having Nonsense Mutations in the Capsid Genes: Growth in Mammalian Cells Containing an Inducible Amber Suppressor, *Virology* 184 310-318 (1991).

Somia et al.; Generation of targeted retroviral vectors by using single-chain variable fragment: An approach to *in vivo* gene delivery, *Proc. Natl. Acad. Sci. USA* 92 7570-7574 (Aug. 1995).

Spitzer et al.; Species specificity for transduction of cultured cells by a recombinant lulll roden parvovirus genome encapsidated by canine parvovirus or feline panleukopenia virus, *Journal of General Virology* 77 1787-1792 (1996).

Srivastava et al.; Construction of a recombinant human parvovirus B19: Adeno-associated virus 2 (AAV) DNA inverted terminal repeats are functional in an AAV-B19 hybrid virus, *Proc. Natl. Acad. Sci. USA* 86 8078-8082 (Oct. 1989).

Tsao et al.; "The Three-Dimensional Structure of Canine Parvovirus and Its Functional Implications," *Science* 251:1456-1464 (Mar. 22, 1991).

Verma et al., "Gene therapy-promises, problems and prospects," *Nature* 389:239-242 (1997).

Williams & Wilkins, "Stedman's Medical Dictionary" (1995).

Xiao et al.; Efficient Long-Term Gene Transfer into Muscle Tissue of Immunocompetent Mice by Adeno-Associated Virus Vector, *Journal of Virology* 70:11 8098-8108 (Nov. 1996).

Xiao et al.; Production of high-titer recombinant adeno-associated virus vectors in the absence of helper adenovirus, *J. Virol.* 72:3 2224 (15 pp.) (Mar. 1998).

Yang et al.; Development of Novel Cell Surface CD34-Targeted Recombinant Adenoassociated Virus Vectors for Gene Therapy, *Human Gene Therapy* 9 1929-1937 (Sep. 1, 1998).

\* cited by examiner

VIRUS VECTORS AND METHODS OF MAKING AND ADMINISTERING THE SAME

RELATED APPLICATION INFORMATION

This application is a divisional of U.S. patent application Ser. No. 09/438,268, filed Nov. 10, 1999 now U.S. Pat. No. 6,491,907, which claims the benefit of U.S. Provisional Application Ser. No. 60/107,840, filed Nov. 10, 1998, and Ser. No. 60/123,651, filed Mar. 10, 1999, which are incorporated herein by reference in their entireties.

STATEMENT OF FEDERAL SUPPORT

This was made, in part, with government support under grant numbers DK42701 and 5-32938 0-110 from the National Institutes of Health. The United States government has certain rights to this invention.

FIELD OF THE INVENTION

The present invention relates to virus vectors, in particular, modified parvovirus vectors and methods of making and administering the same.

BACKGROUND

Parvoviruses are small, single-stranded, non-enveloped DNA viruses between twenty to thirty nanometers in diameter. The genomes of parvoviruses are approximately 5000 nucleotides long, containing two open reading frames. The left-hand open reading frame codes for the proteins responsible for replication (Rep), while the right-hand open reading frame encodes the structural proteins of the capsid (Cap). All parvoviruses have virions with icosahedral symmetry composed of a major Cap protein, usually the smallest of the Cap proteins, and one or two minor Cap proteins. The Cap proteins are generated from a single gene that initiates translation from Most parvoviruses have narrow host ranges; the tropism of B19 is for human erythroid cells (Munshi et al., (1993) *J. Virology* 67:562), while canine parvovirus has a tropism for lymphocytes in adult dogs (Parrish et al., (1988) *Virology* 166:293; Chang et al., (1992) *J. Virology* 66:6858). Adeno-associated virus, on the other hand, can replicate well in canine, mouse, chicken, bovine, monkey, as well as numerous human lines, when the appropriate helper virus is present. In the absence of helper virus, AAV will infect and establish latency in all of these cell types, suggesting that the AAV receptor is common and conserved among species. Several serotypes of AAV have-been identified, including serotypes 1, 2, 3, 4, 5 and 6.

Adeno-associated virus (AAV) is a dependent parvovirus twenty nanometers in size which requires co-infection with another virus (either adenovirus or certain members of the herpes virus group) to undergo a productive infection in cultured cells. In the absence of co-infection with helper virus, the AAV virion binds to a cellular receptor and enters the cell, migrating to the nucleus, and delivers a single-stranded DNA genome that can establish latency by integration into the host chromosome. The interest in AAV as a vector has centered around the biology of this virus. In addition to its unique life-cycle, AAV has a broad host range for infectivity (human, mouse, monkey, dog, etc.), is ubiquitous in humans, and is completely nonpathogenic. The finite packaging capacity of this virus (4.5 kb) has restricted the use of this vector in the past to small genes or cDNAs.

To advance the prospects of AAV gene delivery, vectors sufficient to carry larger genes must be developed. In addition, virions that specifically and efficiently target defined cell types without transducing others will be required for clinical application.

The capsid proteins of AAV2 are Vp1, 2, and 3 with molecular weights of 87, 73, and 62 kDa, respectively. Vp3 represents nearly 80% of the total protein in intact virions, while Vp1 and Vp2 represent 10% each (Muzyczka, (1992) *Curr. Topics Microbiol. Immunol.* 158:97; Rolling et al., (1995) *Molec. Biotech.* 3:9; Wistuba et al. (1997) *J. Virology* 71:1341). Early studies of AAV2 support that all three capsid subunits are required to extract single stranded genomes from the pool of replicating double stranded DNA. These genomes are then sequestered into preformed immature particles that mature to infectious particles. These particles have a density between 1.32 and 1.41 g/mL in cesium chloride and sediment between 60S and 125S in sucrose (Myers et al., (1981) *J. Biological Chem.* 256:567; Myers et al., (1980) *J. Virology* 35:65).

Previous mutagenesis studies of AAV2 capsids have shown that insertions and deletions in the Vp3 domain completely inhibit the accumulation of single stranded virions and production of infectious particles (Hermonat et al., (1984) *J. Virology* 51:329; Ruffing et al., (1992) *J. Virology* 66:6922). Yang et al., (1998) *Human Gene Therapy* 9:1929, have reported the insertion of a sequence encoding the variable region of a single chain antibody against human CD34 at the 5' end of the AAV2 Vp1, Vp2 or Vp3 coding regions. These investigators observed extremely low transduction of CD34 expressing KG-1 cells by AAV virions containing the Vp2 fusion protein (1.9 transducing units/ml or less, sentence spanning pages 1934–35). KG-1 cells are reportedly not permissive to infection by a wild-type rAAV vector. These results with the Vp2 fusion AAV are suspect as transduction of KG-1 cells by this virus was essentially insensitive to an anti-AAV capsid antibody (430 vs. 310 transducing units/ml; Table 2), whereas transduction of HeLa cells was markedly reduced by this antibody (63,2000 vs. <200 transducing units/ml; Table 2). No characterization of the putative fusion virions was undertaken to confirm that the particles contained the Vp2 fusion protein, the antibody was expressed on the capsid surface, or that the particles bound CD34 proteins. In addition, rAAV particles could only be produced if all three wild-type capsid subunits were provided, in addition to the chimeric subunit (Page 1934, Col. 2, lines 5–12). Collectively, these results suggest the chimeric subunits were not incorporated into viable AAV particles, and the low level of chimeric protein observed in target cells was, in fact, due to cellular uptake of chimeric capsid protein or protein aggregates by other mechanisms.

Several studies have demonstrated that parvovirus capsid proteins can be mutated and virion assembly studied. In one study, the coding region for 147 amino acids of the hen egg white lysozyme was substituted for B19 Vp1 unique coding sequence. This modification resulted in purified empty particles that retained lysozyme enzymatic activity (Miyamura et al., (1994) *Proc. Nat. Acad. Sci. USA* 91:8507). In addition, expression of peptides (9 and 13 residues) in B19 Vp2 resulted in empty particles that were immunogenic in mice supporting surface presentation of the insertions (Brown et al., (1994) *Virology* 198:477). In a more recent study, the CD8+CTL epitope (residues 118–132) against lymphocytic choriomeningitis virus (LCAAV) nucleoprotein was inserted into the Vp2 capsid protein of porcine parvovirus (ppv) (Sedlik et al., (1997) *Proc. Nat. Acad. Sci. USA* 94:7503). This capsid protein, with the epitope cloned at the N-terminus, self-assembled when expressed in a baculovirus system. This chimeric virus-like particle was then used to immunize mice against a lethal challenge from LCAAV. While these studies evaluated capsid structure and assembly, they did not address the issue of packaging B19 genomes into the altered capsids.

Recombinant (r)AAV vectors require only the inverted terminal repeat sequences in cis of the 4679 bases to generate virus. All other viral sequences are dispensable and may be supplied in trans (Muzyczka, (1992) *Curr. Topics Microbiol. Immunol.* 158:97). Attractive characteristics of AAV vectors for gene therapy are the stability, genetic simplicity, and ease of genetic manipulation of this virus. While each of these factors remains valid, some obstacles to the application of rAAV vectors have recently come to light. These include inefficiency of vector transduction and packaging constraints. It is not surprising, given the cryptic nature of this virus, that new insights into its biology have surfaced only after extensive research with rAAV vectors, which are more easily assayed compared with wild-type AAV.

With respect to the efficiency of vector transduction, several recent studies have shown great promise in terms of duration of transgene expression in vivo; however, there has been a shortfall in the efficiency of transduction, which was unexpected based on previous results in vitro (Flotte et al., (1993) *Proc. Nat. Acad. Sci. USA* 90:10613). One of the first experiments in rodents to demonstrate the utility of rAAV vectors in vivo was aimed at transduction of brain tissue in rat (Kaplitt et al., (1994) *Nature Genet.* 7:148). In addition to brain, muscle has been found to be efficiently transduced in vivo by AAV vectors, demonstrating long term gene expression (at least 1.5 years), lack of immune response, and no vector toxicity (Xiao et al., (1996) *J. Virol.* 70:8098; Clark et al., (1996) *Hum. Gene Ther.* 8:659; Fisher et at, (1997) *Nat Med.* 3:306; Monahan et al., (1998) *Gene Ther.* 5:40). The primary steps that influence efficient vector delivery are virus entry and conversion of second strand synthesis (see Ferrari et al., (1996) *J. Virology* 70:3227–34).

The overall success of AAV as a general-purpose viral vector depends on the ability to package larger than full-length AAV genomes (5 kb) into rAAV vectors. Studies by Dong et al., (1996) *Hum. Gene Ther.* 7:2101, have determined the packaging limitations using rAAV vectors as between 104% and 108%. This packaging restriction precludes the use of a number of important genes currently being tested for human gene therapy (e.g., the dystrophin gene or current mini-dystrophin constructs).

Accordingly, there remains a need in the art for improved virus vectors with greater packaging limits and transduction efficiency than AAV vectors. In addition, there remains a need for virus vectors with altered tropisms as compared with AAV vectors.

SUMMARY OF THE INVENTION

The present invention provides parvovirus vectors for introducing (i.e., delivering) and, preferably, expressing a nucleotide sequence in a cell. The invention is based, in part, on the discovery that parvovirus vectors possessing unique structures and characteristics as compared with current vectors may be created by substituting or inserting a foreign sequence (i.e., an exogenous amino acid sequence) into a parvovirus capsid. The invention further provides novel vectors that are generated by cross-packaging a parvovirus genome (preferably, an AAV genome) within a different parvovirus capsid. The present invention provides a repertoire of novel parvovirus vectors that may possess unique and advantageous antigenic properties, packaging capabilities, and cellular tropisms as compared with current AAV vectors.

These and other aspects of the invention are set forth in more detail in the description of the invention below.

BRIEF DESCRIPTION OF THE DRAWINGS

FIG. 1 shows the insertional mutagenesis strategy for the AAV2 capsid. A cassette containing the $Kan^r$ gene flanked by EcoRV and Nae I sites were cloned into the plasmid pAV2Cap. pAV2Cap, which contains the open reading frame of AAV2 capsid, was partially digested with Hae III, Nla IV, and Rsa I separately so that unit length products were isolated. The 43 positions of restriction sites for these enzymes are shown above the diagram of the capsid open reading frame. The position of the $Kan^r$ insert was mapped by restriction enzyme digestion and in some cases sequenced. Once the position was determined the $Kan^r$ gene was removed by EcoRV digestion, and the capsid domain subcloned into pACG. This strategy resulted in inserting a 12 base pair fragment, with half Nae I sites flanking a unique Eco RV site, into the respective Hae III, Nla IV, and Rsa I sites. The twelve base pairs code for four amino acids one of which is shown above the diagram of pACG2.

FIG. 2 shows the expression of capsid proteins in cells transfected with wild-type and insertion mutant helper plasmids of pACG2. Cell lysates from 293 cells transfected with 1, H2285; 2, H2634; 3, H2690; 4, N2944; 5, H2944; 6, H3595; 7, H4047; 8, wild-type were analyzed by acrylamide gel electrophoresis and immunoblotting with the B1 monoclonal antibody and detected by peroxidase-conjugated secondary antibody. On the left of the Western blot are the positions of the molecular weight standards and on the right are the positions of the major capsid protein, VP3 and the minor capsid proteins VP2 and VP1.

FIG. 3 shows expression of a Lac Z transgene in cells infected with insertion mutant or wild-type virus. Panel A. Dot blot hybridization to the Lac Z transgene. Cell lysates of adenovirus infected 293 cells transfected with the insertion mutant or wild-type helper plasmids and the Lac Z transgene containing vector were subjected to cesium chloride isopycnic gradient. Fractions from the gradient were treated with DNase and RNase prior to dot blotting to remove unpackaged nucleic acids, fraction numbers are labeled above the dot blot. Fraction 1 has a density range of 1.377–1.41, fraction 2 has a density range of 1.39–1.435, and fraction 3 has a density range of 1.42–1.45. The β-galactosidase gene was used as the control template, to estimate particle numbers. Estimates of particle number where derived assuming 1 μg of 1000 bp DNA has $9.1\times10^{11}$ molecules. Panel B. Infection of HeLa cells with $1.75\times10^{8}$ particles from various insertion mutants and wild-type capsid containing the Lac Z transgene. Cells expressing the transgene appear blue when stained with X-gal.

FIG. 4 shows characterization of the insertion mutants using electron microscopy. 200 uL samples of each virus from peak fraction of gradient were dialyzed against 1×PBS+1 mM $MgCl_2$ and speed-vac desiccated, then resuspended in 20 uL of distilled $H_2O$. Samples were negative stained with 2% phosphotungstic acid. Panel A. rAAV2 with wild-type virion. Infectious insertion viruses H2690 (Panel B), and H2591 (Panel C). Non-infectious viruses H2285 (Panel D), H2634 (Panel E) and, H3595 (Panel F). The black bar is 100 nm; the magnification is equivalent in each panel.

FIG. 5 presents analysis of virion composition from wild-type and various insertion mutant viruses isolated from cell lysates by cesium chloride gradient centrifugation. Peak fractions of virus were determined by dot blot hybridization and dialyzed against 1×PBS+1 mM $MgCl_2$. Foreach, viral sample between $1.0\times10^9$ and $2.5\times10^9$ particles were used. Virions from 1. Wild-type rAAV2; 2. H2285; 3. R2349; 4. H2591; 5. H2634; 6. H2690; 7. H3766; and 8. N4160 were analyzed by acrylamide gel electrophoresis and immunoblotting with the B1 monoclonal antibody and detected by peroxidase-conjugated secondary antibody. On the left of the Western blot are the positions of the molecular weight standards and on the right are the positions of the major capsid protein, VP3 and the minor capsid proteins VP2 and VP1.

FIG. 6 shows the analysis of wild-type and non-infectious insertion mutant virus batch binding to heparin agarose by dot blot hybridization. Viruses with wild-type virions and insertion in the capsids were dialysed against 0.5×PBS and 0.5 mM $MgCl_2$. One hundred microliters of each virus was bound to 100 μl of heparin agarose, at room temperature for one hour. Samples were washed six times with 500 μof wash buffer each, followed by elution with 100 μof 0.5, 1.0 and 1.5M NaCl each, and the supernatant from each wash and elution step was saved. Twenty microliters of supernatant from each step and 20 μl of the agarose pellet were used for dot blot hybridization. Pairs of washes were combined and ⅕₀ of the total volume from each pair was used for dot blot hybridization, while one fifth of the elution supernatant and agarose bed volumes were used. The 100% bound was equivalent to one fifth of the virus added to the heparin agarose. Samples 1. rAAV2 with wild-type virion; 2. H2285; 3. H2416; 4. H2634; and 5. H3761.

Figure 9:
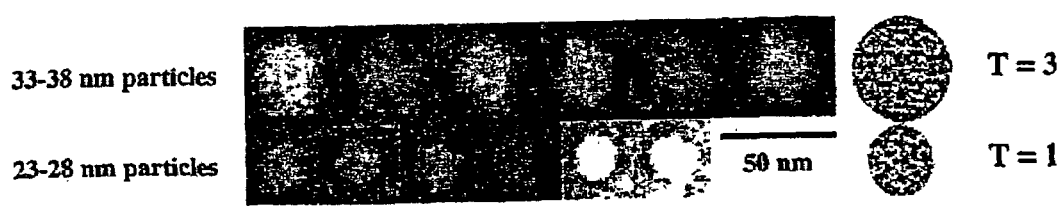
Figure 7:
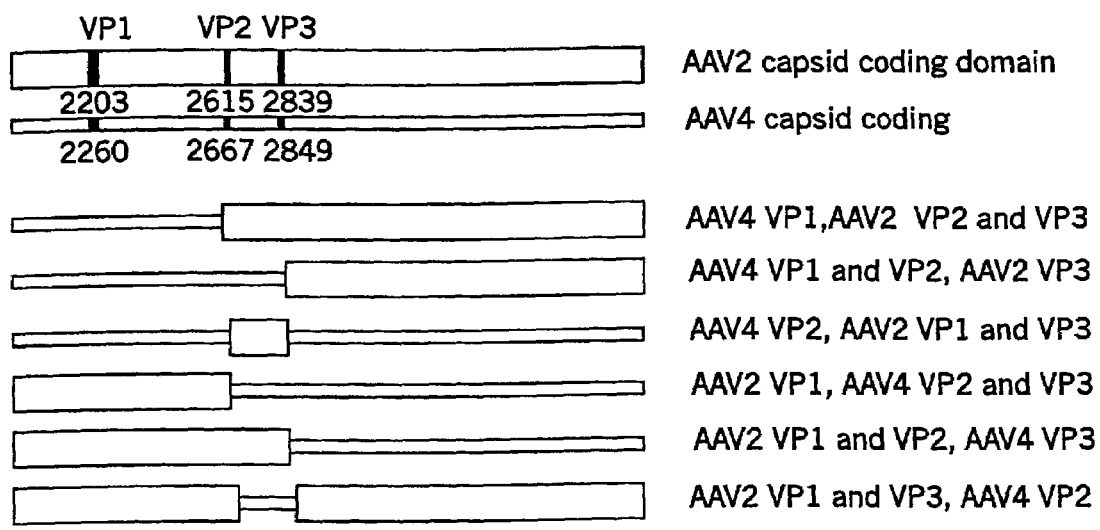
FIG. 7 is schematic representation of the AAV2/4 subunit chimeras.
Figure 8:
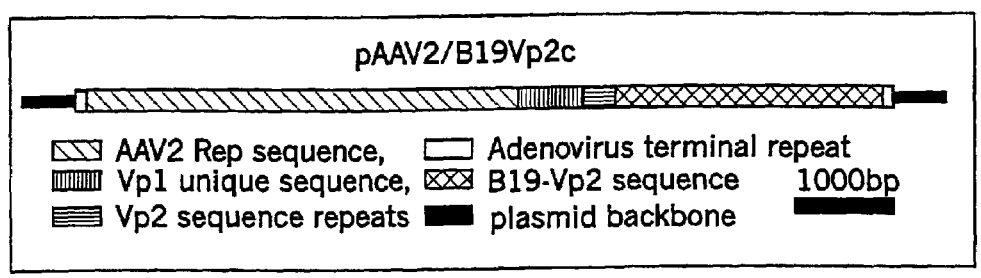
FIG. 8 is a diagram of the helper plasmid pAAV2/B19p2Cap. The coding region of the B19 major structural protein, Vp2, was seamlessly cloned from pAAV-Vp3 to TAA.

FIG. 9 provides EM analysis of chimeric virus particles produced with pAAV/B19Vp2Cap.

DETAILED DESCRIPTION OF THE INVENTION

The present invention provides parvovirus vectors for the delivery of nucleic acids to cells, both in vitro and in vivo. Alternatively, the invention provides novel capsid structures for use, e.g., as vaccines or for delivery of compounds to cells (e.g., as described by U.S. Pat. No. 5,863,541 to Samulski et al., the disclosure of which is incorporated herein by reference in its entirety). The parvovirus vectors of the present invention utilize the advantageous properties of AAV vectors, and may mitigate some of the problems encountered with these vectors. In particular embodiments, the parvovirus vectors may possess different or altered characteristics from AAV vectors, including but not limited to, antigenic properties, packaging capabilities, and/or cellular tropism.

The term "parvovirus" as used herein encompasses all parvoviruses, including autonomously-replicating parvoviruses and dependoviruses. The autonomous parvoviruses include members of the genera *Parvovirus, Erythrovirus, Densovirus, Iteravirus,* and *Contravirus*. Exemplary autonomous parvoviruses include, but are not limited to, mouse minute virus, bovine parvovirus, canine parvovirus, chicken parvovirus, feline panleukopenia virus, feline parvovirus, goose parvovirus, and B19 virus. Other autonomous parvoviruses are known to those skilled in the art. See, e.g., BERNARD N. FIELDS et al., VIROLOGY, volume 2, chapter 69 (3d ed., Lippincoff-Raven Publishers).

The genus *Dependovirus* contains the adeno-associated viruses AAV), including but not limited to, AAV type 1, AAV type 2, AAV type 3, AAV type 4, AAV type 5, AAV type 6, avian AAV, bovine AAV, canine AAV, equine AAV, and ovine AAV. See, e.g., BERNARD N. FIELDS et al., VIROLOGY, volume 2, chapter 69 (3d ed., Lippincott-Raven Publishers).

The parvovirus particles, capsids and genomes of the present invention are preferably from AAV.

The term "tropism" as used herein refers to entry of the virus into the cell, optionally and preferably, followed by expression of sequences carried by the viral genome in the cell, e.g., for a recombinant virus, expression of the heterologous nucleotide sequences(s). Those skilled in the art will appreciate that transcription of a heterologous nucleic acid sequence from the viral genome may not be initiated in the absence of trans-acting factors, e.g., for an inducible promoter or otherwise regulated nucleic acid sequence. In the case of AAV, gene expression from the viral genome may be from a stably integrated provirus, from a non-integrated episome, as well as any other form in which the virus may take within the cell.

The parvovirus vectors of the present invention are useful for the delivery of nucleic acids to cells both in vitro and in vivo. In particular, the inventive vectors may be advantageously employed to deliver or transfer nucleic acids to animal cells. Nucleic acids of interest include nucleic acids encoding peptides and proteins, preferably therapeutic (e.g., for medical or veterinary uses) or immunogenic (e.g., for vaccines) peptides or proteins.

A "therapeutic" peptide or protein is a peptide or protein that may alleviate or reduce symptoms that result from an absence or defect in a protein in a cell or subject. Alternatively, a "therapeutic" peptide or protein is one that otherwise confers a benefit to a subject, e.g., anti-cancer effects. Therapeutic peptides and proteins include, but are not limited to, CFTR (cystic fibrosis transmembrane regulator protein), dystrophin (including the protein product of dystrophin mini-genes, see, e.g, Vincent et al., (1993) *Nature Genetics* 5:130), utrophin (Tinsley et al., (1996) *Nature* 384:349), clotting factors (Factor XIII, Factor IX, Factor X, etc.), erythropoietin, the LDL receptor, lipoprotein lipase, ornithine transcarbamylase, β-globin, α-globin, spectrin, α-antitrypsin, adenosine deaminase, hypoxanthine guanine phosphoribosyl transferase, β-glucocerebrosidase, sphingomyelinase, lysosomal hexosaminidase, branched-chain keto acid dehydrogenase, hormones, growth factors (e.g., insulin-like growth factors 1 and 2, platelet derived growth factor, epidermal growth factor, nerve growth factor, neurotrophic factor −3 and −4, brain-derived neurotrophic factor, glial derived growth factor, transforming growth factor-αand -β, and the like), cytokines (e.g., α-interferon, β-interferon, interferon-γ, interleukin-2, interleukin-4, interleukin 12, granulocyte-macrophage colony stimulating factor, lymphotoxin), suicide gene products (e.g., herpes simplex virus thymidine kinase, cytosine deaminase, diphtheria toxin, cytochrome P450, deoxycytidine kinase, and tumor necrosis factor), proteins conferring resistance to a drug used in cancer therapy, tumor suppressor gene products (e.g., p53, Rb, Wt-1, NF1, VHL, APC, and the like), and any other peptide or protein that has a therapeutic effect in a subject in need thereof.

Further exemplary therapeutic peptides or proteins include those that may used in the treatment of a disease condition including, but not limited to, cystic fibrosis (and other diseases of the lung), hemophilia A, hemophilia B, thalassemia, anemia and other blood disorders, AIDS, Alzheimer's disease, Parkinson's disease, Huntington's disease, amyotrophic lateral sclerosis, epilepsy, and other neurological disorders, cancer, diabetes mellitus, muscular dystrophies (e.g., Duchenne, Becker), Gaucher's disease, Hurler's disease, adenosine deaminase deficiency, glycogen storage diseases and other metabolic defects, retinal degenerative diseases (and other diseases of the eye), and diseases of solid organs (e.g., brain, liver, kidney, heart).

The present invention also provides vectors useful as vaccines. The use of parvoviruses as vaccines is known in the art (see, e.g., Miyamura et al., (1994) *Proc. Nat. Acad. Sci USA* 91:8507; U.S. Pat. No. 5,916,563 to Young et al., 5,905,040 to Mazzara et al., U.S. Pat. Nos. 5,882,652, U.S. Pat. No. 5,863,541 to Samulski et al.; the disclosures of which are incorporated herein in their entirety by reference). The antigen may be presented in the parvovirus capsid, as described below for chimeric and modified parvovirus vectors. Alternatively, the antigen may be expressed from a heterologous nucleic acid introduced into a recombinant AAV genome and carried by the inventive parvoviruses. Any immunogen of interest may be provided by the parvovirus vector. Immunogens of interest are well-known in the art and include, but are not limited to, immunogens from human immunodeficiency virus, influenza virus, gag proteins, tumor antigens, cancer antigens, bacterial antigens, viral antigens, and the like.

As a further alternative, the heterologous nucleic acid sequence may encode a reporter peptide or protein (e.g., an enzyme). Reporter proteins are known in the art and include, but are not limited to, Green Fluorescent Protein, β-galactosidase, alkaline phosphatase, chloramphenicol acetyltransferase, and the like.

Alternatively, in particular embodiments of the invention, the nucleic acid of interest may encode an antisense nucleic acid, a ribozyme (e.g., as described in U.S. Pat. No. 5,877,022), RNAs that effect spliceosome-mediated trans-splicing (Puffaraju et al., (1999) *Nature Biotech.* 17:246), or other non-translated RNAs, such as "guide" RNAs (Gorman et al., (1998) *Proc. Nat. Acad. Sci. USA* 95:4929; U.S. Pat. No. 5,869,248 to Yuan et al.), and the like.

Except as otherwise indicated, standard methods known to those skilled in the art may be used for the construction of rAAV genomes, transcomplementing packaging vectors, transiently and stably transfected packaging cells according to the present invention. Such techniques are known to those skilled in the art. See, e.g., SAMBROOK et al., MOLECULAR CLONING: A LABORATORY MANUAL 2nd Ed. (Cold Spring Harbor, N.Y., 1989); F. M. AUSUBEL et al. CURRENT PROTOCOLS IN MOLECULAR BIOLOGY (Green Publishing Associates, Inc. and John Wiley & Sons, Inc., New York).

I. Hybrid Viruses.

The hybrid parvovirus vectors of the present invention may overcome some of the disadvantages of AAV vectors for delivery of nucleic acids or other molecules to cells.

A "hybrid" parvovirus, as used herein, is an AAV genome encapsidated within a different (i.e., another, foreign, exogenous) parvovirus capsid. Alternatively stated, a hybrid parvovirus has a parvovirus genome encapsidated within a different parvovirus capsid. As used herein, by "different" it is intended that the AAV genome is packaged within another parvovirus capsid, e.g., the parvovirus capsid is from another AAV serotype or from an autonomous parvovirus.

Preferably, the parvovirus genome is an AAV genome (preferably a recombinant AAV genome). It is also preferred that the AAV genome comprises one or more AAV inverted terminal repeat(s) as described below. Typically, as described in more detail below, a recombinant AAV (rAAV) genome will retain only those elements required in cis (e.g., one or more AAV ITRs), with the rest of the genome (e.g., the rep/cap genes) being provided in trans.

In particular preferred embodiments the parvovirus capsid is an AAV capsid (i.e., a hybrid AAV vector). According to this embodiment, the AAV capsid packages an AAV genome of a different serotype (and preferably, of a different serotype from the one or more AAV ITRs). For example, a recombinant AAV type 1, 2, 3, 4, 5 or 6 genome may be encapsidated within an AAV type 1, 2, 3, 4, 5 or 6 capsid, provided that the AAV capsid and genome (and preferably, the one or more AAV ITRs) are of different serotypes.

Illustrative hybrid parvoviruses according to the present invention are an AAV type 2 genome packaged within an AAV type 1, 3, 4, 5 or 6 capsid. In particular preferred embodiments, the hybrid parvovirus comprises an AAV type 3, type 4, or type 5 capsid packaging an AAV type 2 genome, more preferably, an AAV type 3 or type 5 capsid packaging a type 2 genome.

In other preferred embodiments, an AAV type 1, 3, 4, 5 or 6 genome is packaged within a different AAV capsid (e.g., a type 1 genome in a type 2, 3, 4, 5, or 6 capsid, and the like).

Also preferred are hybrid B19/AAV parvoviruses in which an AAV genome (e.g., an AAV type 1, 2, 3, 4, 5 or 6 genome) is packaged within a B19 capsid. More preferably, the hybrid parvovirus has a B19 capsid and an AAV type 2 genome.

Further preferred are hybrid parvoviruses in which a mouse minute virus, bovine parvovirus, canine parvovirus, chicken parvovirus, feline panleukopenia virus, feline parvovirus, or goose parvovirus capsid packages an AAV genome, more preferably an AAV type 2 genome.

Specific hybrid viruses include those having the capsid sequence encoded by nucleotides 2123 to 4341 of SEQ ID NO:1. This sequence encodes the AAV2 rep genes and AAV4 capsid in a pBluescript backbone. It is also preferred that the hybrid parvovirus having the capsid sequence given by SEQ ID NO:1 is an AAV2 genome. Alternatively, the nucleotide sequence of the AAV4 capsid is substantially homologous to the nucleotide sequence given as nucleotides 2123 to 4341 of SEQ ID NO:1. As a further alternative, the nucleotide sequence of the AAV4 capsid encodes the amino acid sequence encoded by nucleotides 2123 to 4341 in SEQ ID NO:1. The term "substantially homologous" is as defined hereinbelow.

One of the limitations of current AAV vectors for gene delivery is the prevalence of neutralizing antibodies against AAV within the human population. For example, it is estimated that 80% of adults are seropositive for AAV type 2. In preferred embodiments, the instant invention provides hybrid parvovirus vectors that may be advantageously employed to reduce (e.g., diminish, decrease, mitigate, and the like) an immune response in the subject being treated. Thus, for example, a rAAV type 2 vector genome carrying a heterologous nucleic acid sequence or sequences may be packaged within an AAV type 3 capsid and administered to a subject who is seropositive for AAV type 2 and cannot neutralize AAV type 3 virus.

According to this aspect of the invention, a rAAV genome may be packaged within any non-homologous parvovirus capsid for delivery to a cell, in vitro or in vivo. In preferred embodiments, the AAV genome is packaged within an array of non-homologous capsids to overcome neutralizing antibodies and/or or to prevent the development of an immune response. In particular preferred embodiments, the rAAV may be delivered within a series of hybrid virus particles, so as to continually present the immune system with a new virus vector. This strategy will allow for repeated administration without immune clearance.

A further limitation encountered with AAV vectors concerns the cellular tropism of this virus. The wild-type tropism of AAV is problematic both because AAV infects a wide range of cell types and because it exhibits no infectivity in other potential target cells of interest (e.g., erythroid cells). Autonomous parvoviruses, in contrast, have a narrower cellular tropism. The tropisms of particular autonomous parvoviruses are known to those skilled in the art. Illustrative cellular tropisms of autonomous parvoviruses include: B19 virus (erythroid cells), canine parvovirus (gut epithelium), AAVM(p) (fibroblasts); and goose parvovirus (myocardial lining of the heart). Furthermore, autonomous parvoviruses exhibit a wider range of host species than does AAV, which characteristic may be utilized to develop AAV vectors for administration to bovines, canines, felines, geese, ducks, and the like, e.g., for veterinary treatments. Thus, cross-packaging of AAV genomes in autonomous parvovirus capsids according to the present invention may be utilized to produce a virus vector with a different cellular tropism than AAV.

With respect to AAV/AAV hybrids, all of the AAV serotypes infect a broad host range of cells. However, there are differences in the rates of vector transduction, suggesting that the different serotypes may use different cellular receptors. In addition, only limited competition is observed among serotypes in binding experiments, which observation further indicates that the different serotypes have evolved to use distinct receptors (Mizukami et al., (1996) *Virology* 217:124). Accordingly, hybrid parvoviruses of the present invention that package an AAV genome in an AAV capsid of a different serotype also provide opportunities for delivering AAV vectors to a wider range of cell types than current AAV vectors and/or for directing AAV vectors to specific target cells.

In preferred embodiments, the hybrid parvovirus particle contains a rAAV genome. As used herein, the rAAV genome carries at least one heterologous nucleic acid sequence to be delivered to a cell. Those skilled in the art will appreciate that the rAAV genome can encode more than one heterologous nucleic acid sequence (e.g., two, three or more heterologous nucleic acid sequences), generally only limited by the packaging capacity of the virus capsid. Heterologous nucleic acid sequence(s) of interest for use according to the present invention are as described above.

As used herein, a recombinant hybrid parvovirus particle encompasses virus particles with hybrid, chimeric, targeted and/or modified parvovirus capsids as described hereinbelow. Moreover, those skilled in the art will understand that the parvovirus capsid may include other modifications or mutations (e.g., deletion, insertion, point and/or missense mutations, and the like). Likewise, the rAAV genome may include modifications or mutations (e.g., deletion, insertion, point and/or missense mutations, and the like). Those skilled in the art will further appreciate that mutations may incidentally be introduced into the rAAV genome or parvovirus capsid as a result of the cloning strategy employed.

The rAAV genome of the hybrid parvovirus preferably encodes at least one AAV inverted terminal repeat (ITR), preferably two AAV ITRs, and more preferably two homologous AAV ITRs, which flank the heterologous nucleic acid sequence(s) to be delivered to the cell. The AAV ITR(s) may be from any AAV, with types 1, 2, 3, 4, 5 and 6 being preferred, and type 2 being most preferred. The term "inverted terminal repeat" includes synthetic sequences that function as an AAV inverted terminal repeat, such as the "double-D sequence" as described in U.S. Pat. No. 5,478,745 to Samulski et al., the disclosure of which is incorporated in its entirety herein by reference. It has been demonstrated that only a single 165 bp double-D sequence is required in cis for site specific integration, replication, and encapsidation of vector sequences. AAV ITRs according to the present invention need not have a wild-type ITR sequence (e.g., a wild-type sequence may be altered by insertion, deletion, truncation or missense mutations), as long as the ITR functions to mediate virus packaging, replication, integration, and/or provirus rescue, and the like.

In hybrid parvoviruses according to the present invention, the AAV ITR(s) is different from the parvovirus capsid. Moreover, if the capsid is an AAV capsid, the capsid and the ITR(s) are of different AAV serotypes. In preferred embodiments, the AAV ITR(s) is from AAV type 2 and the parvovirus capsid is an AAV type 3, 4 or 5 capsid, more preferably an AAV type 3 or 5 capsid. In alternate preferred embodiments, the hybrid parvovirus has a B19 capsid and the AAV ITR(s) is from AAV type 2.

The rAAV genomes of the invention may additionally contain expression control elements, such as transcription/translation control signals, origins of replication, polyadenylation signals, and internal ribosome entry sites (IRES), promoters, enhancers, and the like, operably associated with the heterologous nucleic acid sequence(s) to be delivered to the cell. Those skilled in the art will appreciate that a variety of promoter/enhancer elements may be used depending on the level and tissue-specific expression desired. The promoter/enhancer may be constitutive or inducible, depending on the pattern of expression desired. The promoter/enhancer may be native or foreign and can be a natural or a synthetic sequence. By foreign, it is intended that the promoter/enhancer region is not found in the wild-type host into which the promoter/enhancer region is introduced.

Promoters/enhancers that are native to the target cell or subject to be treated are most preferred. Also preferred are promoters/enhancers that are native to the heterologous nucleic acid sequence. The promoter/enhancer is chosen so that it will function in the target cell(s) of interest. Mammalian promoters/enhancers are also preferred.

Inducible expression control elements are preferred in those applications in which it is desirable to provide regulation over expression of the heterologous nucleic acid sequence(s). Inducible promoters/enhancer elements for gene delivery are preferably tissue-specific promoter/enhancer elements, and include muscle specific (including cardiac, skeletal and/or smooth muscle), neural tissue specific (including brain-specific), liver specific, bone marrow specific, pancreatic specific, spleen specific, retinal specific, and lung specific promoter/enhancer elements. Other inducible promoter/enhancer elements include hormone-inducible and metal-inducible elements. Exemplary inducible promoters/enhancer elements include, but are not limited to, a Tet on/off element, a RU486-inducible promoter, an ecdysone-inducible promoter, a rapamycin-inducible promoter, and a metalothionein promoter.

In embodiments of the invention in which the heterologous nucleic acid sequence(s) will be transcribed and then translated in the target cells, specific initiation signals are generally required for efficient translation of inserted protein coding sequences. These exogenous translational control sequences, which may include the ATG initiation codon and adjacent sequences, can be of a variety of origins, both natural and synthetic.

The AAV genome of the inventive parvovirus vectors may optionally include the genes that encode the AAV Cap and Rep proteins. In preferred embodiments, the genes encoding at least one of the AAV Cap proteins or at least one of the AAV Rep proteins will be deleted from the rAAV genome. According to this embodiment, the Cap and Rep functions may be provided in trans, e.g., from a transcomplementing packaging vector or by a stably-transformed packaging cell line. In more preferred embodiments, the genes encoding all of the AAV Cap proteins or all of the AAV Rep proteins will be deleted from the rAAV genome. Finally, in the most preferred embodiments, all of the AAV cap genes and all of the AAV rep genes are deleted from the AAV vector. This configuration maximizes the size of the heterologous nucleic acid sequence(s) that can be carried by the AAV genome, simplifies cloning procedures, and minimizes recombination between the rAAV genome and the rep/cap packaging sequences provided in trans.

In hybrid parvoviruses according to the present invention, the parvovirus cap genes (if present) may encode the Cap proteins from any parvovirus, preferably an AAV. In contrast, the rep genes (if present) will typically and preferably be AAV rep genes. It is further preferred that the rep genes and the AAV inverted terminal repeat(s) carried by the AAV genome are of the same serotype. Moreover, if the cap genes are AAV cap genes, the rep genes will preferably be of a different AAV serotype from the AAV cap genes.

The rep genes/proteins of different AAV serotypes may be evaluated for those giving the highest titer vector in connection with particular hybrid parvoviruses without undue experimentation. In particular preferred embodiments, the AAV rep genes encode a temperature-sensitive Rep78 and/or Rep68 protein as described by Gavin et al., (1999) *J. Virology* 73:9433 (the disclosure of which is incorporated herein by reference in its entirety).

As described above, the Cap proteins of the hybrid parvovirus are different from the AAV genome (i.e., the Cap proteins are either from a different AAV serotype or from an autonomous parvovirus). In addition, as described above, the Cap proteins will typically and preferably be different from the rep genes (if present).

Accordingly, in particular preferred embodiments, the hybrid parvovirus has an AAV type 3, 4 or 5 capsid and carries an AAV type 2 genome including an AAV type 2 ITR(s). The AAV genome may additionally include the AAV rep genes (preferably type 2) and AAV cap genes (preferably, AAV type 3, 4, or 5, respectively). Typically, however, the AAV genome will be a rAAV genome, and the rep and cap genes will be deleted therefrom. In an alternate preferred embodiment, the hybrid parvovirus has a B19 capsid and carries an AAV genome, more preferably an AAV type 2 genome, including an AAV ITR(s). The AAV genome may optionally encode the AAV Rep proteins (preferably AAV type 2) and B19 capsid proteins, but preferably is a rAAV genome lacking these sequences.

The present invention also provides nucleotide sequences and vectors (including cloning and packaging vectors) encoding the inventive AAV genomes and the parvovirus cap gene(s) and the AAV rep gene(s) for producing the inventive hybrid parvoviruses. As described above, in preferred embodiments, at least one of the AAV rep genes or one of the AAV cap genes, more preferably all of the AAV rep genes and the AAV cap genes, are deleted from the AAV genome. The Rep and Cap functions may be provided in trans by packaging vector(s). Multiple packaging vectors (e.g., two, three, etc.) may be employed, but typically and preferably all of the Rep and Cap functions are provided by a single packaging vector.

Cloning and packaging vectors may be any vector known in the art. Illustrative vectors include, but are not limited to, plasmids, naked DNA vectors, bacterial artificial chromosomes (BACs), yeast artificial chromosomes (YACs), and viral vectors. Preferred viral vectors include AAV, adenovirus, herpesvirus, Epstein-Barr virus (EBV), baculovirus, and retroviral (e.g., lentiviral) vectors, more preferably, adenovirus and herpesvirus vectors.

The present invention also provides cells containing the inventive vectors. The cell may be any cell known in the art including bacterial, protozoan, yeast, fungus, plant, and animal (e.g., insect, avian, mammalian) cells.

Further provided are stably-transformed packaging cells that express the sequences encoding the parvovirus cap gene(s) and/or the AAV rep gene(s) for producing the inventive hybrid parvoviruses. Any suitable cell known in the art may be employed to express the parvovirus cap and/or rep gene(s). Mammalian cells are preferred (e.g., HeLa cells). Also preferred are trans-complementing packaging cell lines that will provide functions deleted from a replication-defective helper virus, e.g., 293 cells or other E1a trans-complementing cells.

In particular preferred embodiments, at least one of the rep genes or at least one of the cap genes, more preferably all of the cap genes or all of the rep genes are stably integrated into the genetic material of the packaging cell and are expressed therefrom. Typically, and most preferably, all of the parvovirus cap genes and all of the AAV rep genes are stably integrated and expressed by the packaging cell.

The cap and rep genes and proteins are as described above with respect to hybrid AAV genomes. Thus, the packaging vector(s) and/or packaging cell may encode the cap genes from any parvovirus. Preferred are the B19, AAV type 3, AAV type 4 and AAV type 5 cap genes. Likewise, the packaging vector(s) and/or packaging cell may encode the rep genes from any parvovirus. Preferably, however, the rep genes will be AAV genes, more preferably, AAV type 2, AAV type 3, AAV type 4, or AAV type 5 rep genes. Most preferably, the rep genes are AAV type 2 rep genes. In particular preferred embodiments, the AAV rep sequences encode a temperature-sensitive Rep78 or Rep68 protein as described by Gavin et al., (1999) *J. Virology* 73:9433.

The expression of the cap and rep genes, whether carried by the rAAV genome, a packaging vector, or stably integrated into the genome of a packaging cell may be driven by any promoter or enhancer element known in the art, as described in more detail above. Preferably, the cap or rep genes (more preferably both) are operably associated with parvovirus promoters. In the most preferred embodiments, the cap genes and rep genes are operably associated with their authentic promoters (i.e., the native promoter).

A previous report indicates that expression of parvovirus cap genes from a B19/AAV type 2 hybrid helper vector cannot be achieved using authentic promoters. Ponnazhagan et al., (1998) *J. Virology* 72:5224, attempted to generate a helper vector for producing a B19 parvovirus capsid packaging an AAV type 2 genome. These investigators reported that virus could not be packaged when the cap genes on the helper vector were driven by either the authentic AAV p40 or B19 p6 promoters. Packaging of virus was only successfully achieved when the CAAV promoter (a strong promoter) was substituted for the authentic promoters. It appears that the natural regulation of the cap genes was disrupted, and cap gene expression was restored only by splitting up the rep and cap coding regions and using an exogenous promoter to drive cap gene expression.

Likewise, the cloning strategy proposed by U.S. Pat. No. 5,681,731 to Lebkowski et al. for generating hybrid viruses comprising an autonomous parvovirus capsid encapsidating a rAAV genome (col. 15–16) will fail to result in packaged virus.

In contrast, the present invention provides hybrid packaging vectors and packaging cells in which parvovirus promoters, preferably the authentic promoters, may be used to drive expression of the parvovirus cap and rep genes to produce the inventive hybrid parvoviruses. Previous efforts to create hybrid parvovirus cap/rep gene constructs using authentic promoters have not succeeded, at least in part, because these investigators failed to preserve the integrity of the splice sites required for proper processing of the rep genes. The present investigations have utilized a seamless cloning strategy (Stratagene USA) in which the splice sites within the rep genes have been preserved. Alternatively, site-directed mutagenesis (or similar techniques) may be used to restore the splice sites to the hybrid virus constructs.

The present invention further encompasses methods of producing the inventive hybrid parvoviruses. Hybrid parvovirus particles according to the invention may be produced by introducing an AAV genome to be replicated and packaged into a permissive or packaging cell, as those terms are understood in the art (e.g., a "permissive" cell can be infected or transduced by the virus; a "packaging" cell is a stably transformed cell providing helper functions). Preferably, the AAV genome is a rAAV genome encoding a heterologous nucleic acid sequence(s) that is flanked by at least one AAV ITR. rAAV genomes, AAV ITRs, and heterologous nucleic acid sequences are all as described in more detail hereinabove. The AAV genome may be provided to the cell by any suitable vector, as described hereinabove.

Any method of introducing the vector carrying the AAV genome into the permissive cell may be employed, including but not limited to, electroporation, calcium phosphate precipitation, microinjection, cationic or anionic liposomes, and liposomes in combination with a nuclear localization signal. In embodiments wherein the AAV genome is provided by a virus vector, standard methods for producing viral infection may be used.

Any suitable permissive or packaging cell known in the art may be employed to produce AAV vectors. Mammalian cells are preferred. Also preferred are trans-complementing packaging cell lines that provide functions deleted from a replication-defective helper virus, e.g., 293 cells or other E1a trans-complementing cells.

The AAV genome may contain some or all of the AAV cap and rep genes, as described herein. Preferably, however, some or all of the cap and rep functions are provided in trans by introducing a packaging vector(s), as described above, into the cell. Alternatively, the cell is a packaging cell that is stably transformed to express the cap and/or rep genes. Packaging vectors and packaging cells are as described hereinabove.

In addition, helper virus functions are provided for the AAV vector to propagate new virus particles. Both adenovirus and herpes simplex virus may serve as helper viruses for AAV. See, e.g., BERNARD N. FIELDS et al., VIROLOGY, volume 2, chapter 69 (3d ed., Lippincoft-Raven Publishers). Exemplary helper viruses include, but are not limited to, Herpes simplex (HSV) *varicella zoster*, cytomegalovirus, and Epstein-Barr virus. The multiplicity of infection (MOI) and the duration of the infection will depend on the type of virus used and the packaging cell line employed. Any suitable helper vector may be employed. Preferably, the helper vector(s) is a plasmid, for example, as described by Xiao et al., (1998) *J. Virology* 72:2224. The vector can be introduced into the packaging cell by any suitable method known in the art, as described above.

AAV vectors can be produced by any suitable method known in the art. The traditional production of rAAV vectors entails co-transfection of a rep/cap vector encoding AAV helper and the AAV vector into human cells infected with adenovirus (Samulski et al., (1989) *J. Virology* 63:3822). Under optimized conditions, this procedure can yield up to $10^9$ infectious units of rAAV per ml. One drawback of this method, however, is that it results in the co-production of contaminating wild-type adenovirus in rAAV preparations. Since several adenovirus proteins (e.g., fiber, hexon, etc.) are known to produce a cytotoxic T-lymphocyte (CTL) immune response in humans (Yang and Wilson, (1995) *J. Immunol.* 155:2564; Yang et al., (1995) *J. Virology* 69:2004; Yang et al., (1994) *Proc. Nat. Acad. Sci. USA* 91:4407), this represents a significant drawback when using these rAAV preparations (Monahan et al., (1998) *Gene Therapy* 5:40).

AAV vector stocks free of contaminating helper virus may be obtained by any method known in the art. For example, AAV and helper virus may be readily differentiated based on size. AAV may also be separated away from helper virus based on affinity for a heparin substrate (Zolotukhin et al (1999) *Gene Therapy* 6:973). Preferably, deleted replication-defective helper viruses are used so that any contaminating helper virus is not replication competent. As a further alternative, an adenovirus helper lacking late gene expression may be employed, as only adenovirus early gene expression is required to mediate packaging of AAV virus. Adenovirus mutants defective for late gene expression are known in the art (e.g., ts100K and ts149 adenovirus mutants).

A preferred method for providing helper functions through infectious adenovirus employs a non-infectious adenovirus miniplasmid that carries all of the helper genes required for efficient AAV production (Ferrari et al., (1997) *Nature Med.* 3:1295; Xiao et al., (1998) *J. Virology* 72:2224). The rAAV titers obtained with adenovirus miniplasmids are forty-fold higher than those obtained with conventional methods of wild-type adenovirus infection (Xiao et al., (1998) *J. Virology* 72:2224). This approach obviates the need to perform co-transfections with adenovirus (Holscher et al., (1994), *J. Virology* 68:7169; Clark et al., (1995) *Hum. Gene Ther.* 6:1329; Trempe and Yang, (1993), in, Fifth Parvovirus Workshop, Crystal River, Fla.).

Other methods of producing rAAV stocks have been described, including but not limited to, methods that split the rep and cap genes onto separate expression cassettes to prevent the generation of replication-competent AAV (see, e.g., Allen et al., (1997) *J. Virol.* 71:6816), methods employing packaging cell lines (see, e.g., Gao et al., (1998) *Human Gene Therapy* 9:2353; Inoue et al., (1998) *J. Virol.* 72:7024), and other helper virus free systems (see, e.g., U.S. Pat. No. 5,945,335 to Colosi).

Accordingly, the AAV genome to be packaged, parvovirus cap genes, AAV rep genes, and helper functions are provided to a cell (e.g., a permissive or packaging cell) to produce AAV particles carrying the AAV genome. The combined expression of the rep and cap genes encoded by the AAV genome and/or the packaging vector(s) and/or the stably transformed packaging cell results in the production of a hybrid parvovirus in which a parvovirus capsid encapsidates an AAV genome. The hybrid parvovirus particles are allowed to assemble within the cell, and are then recovered by any method known by those of skill in the art.

The reagents and methods disclosed herein may be employed to produce high-titer stocks of the inventive parvovirus vectors. Preferably, the parvovirus stock has a titer of at least about $10^5$ transducing units (tu)/ml, more preferably at least about $10^6$ tu/ml, more preferably at least about $10^7$ tu/ml, yet more preferably at least about $10^8$ tu/ml, yet more preferably at least about $10^9$ tu/ml, still yet more preferably at least about $10^{10}$ tu/ml, still more preferably at least about $10^{11}$ tu/ml, or more.

Alternatively stated, the parvovirus stock preferably has a titer of at least about 1 tu/cell, more preferably at least about 5 tu/cell, still more preferably at least about 20 tu/cell, yet more preferably at least about 50 tu/cell, still more preferably at least about 100 tu/cell, more preferably still at least about 250 tu/cell, most preferably at least about 500 tu/cell, or even more.

It is also preferred that the parvovirus is produced at essentially wild-type titers.

Those skilled in the art will appreciate that the instant invention also encompasses hybrid parvovirus vectors that contain chimeric capsids and/or capsids that have been modified by insertion of an amino acid sequence(s) into the capsid to confer altered tropisms or other characteristics, each as discussed in more detail below. The virus capsids may also include other modifications, e.g., deletion, insertion, point and/or missense mutations, and the like.

Those skilled in the art will further appreciate that mutations may incidentally be introduced into the cap and/or rep genes as a result of the particular cloning strategy employed. For example, the construction of sequences encoding hybrid parvovirus genomes as described above may result in chimeric rep genes (and proteins) because of the overlap of the rep and cap sequences (e.g., the cap genes and 3' end of the rep genes may be AAV type 3, and the remainder of the rep genes may be AAV type 2). As described above, chimeric AAV rep genes in which the 3' region is derived from an autonomous parvovirus will generally not function as the splicing signals are not conserved among AAV and the autonomous parvoviruses, unless site-directed mutagenesis, or a similar technique, is employed to restore the splice sites to the hybrid virus constructs.

II. Chimeric Viruses.

The present invention further provides the discovery that chimeric parvoviruses may be constructed that possess unique capsid structures and characteristics. The strategy described above focused on altering AAV virus structure and function by cross-packaging AAV genomes within different parvovirus capsids. Further diversity in virus particles may be achieved by substituting a portion of the parvovirus capsid with a portion of a capsid(s) from a different (i.e., another or foreign) parvovirus(es). Alternatively, a portion of a different parvovirus capsid(s) may be inserted (i.e., rather than substituted) into the parvovirus capsid to create a chimeric parvovirus capsid. Also disclosed are vectors, packaging cells, and methods for constructing chimeric parvovirus particles. The chimeric parvoviruses disclosed herein may possess new antigenic properties, packaging capabilities, and/or cellular tropisms. The chimeric capsids and virus particles of the invention are also useful for raising chimera-specific antibodies against the novel capsid structures.

Parvoviruses, AAV, and rAAV genomes are as described above with respect to hybrid parvoviruses.

As used herein, a "chimeric" parvovirus is a parvovirus in which a foreign (i.e., exogenous) capsid region(s) from a different parvovirus(s) is inserted or substituted into the parvovirus capsid. Preferably the foreign capsid region is substituted for one of the native parvovirus capsid regions. In particular embodiments, the foreign capsid region is swapped for the homologous capsid region within the parvovirus capsid. It is also preferred that the parvovirus capsid is an AAV capsid. According to this embodiment, the AAV capsid may be of any AAV serotype (e.g., type 1, type 2, type 3, type 4, type 5, type 6, etc., as described above). More preferably, the AAV capsid is an AAV type 2, type 3, type 4, or type 5 capsid, most preferably an AAV type 2 capsid.

Those skilled in the art will appreciate that the chimeric parvovirus may additionally be a hybrid parvovirus (as described above) or may be a targeted, or otherwise modified, parvovirus (as described below). Those skilled in the art will further appreciate that due to the overlap in the sequences encoding the parvovirus capsid proteins, a single insertion or substitution may affect more than one capsid subunit.

The foreign parvovirus capsid region may be from any parvovirus (i.e., an autonomous parvovirus or dependovirus) as described above. Preferably, the foreign capsid region is from the human B19 parvovirus or from AAV type 3, type 4, or type 5.

The foreign parvovirus capsid region may constitute all or substantially all of a capsid subunit(s) (i.e., domain, for example the Vp1, Vp2 and Vp3 subunits of AAV or the Vp1 and Vp2 subunits of B 19 virus) or a portion of a capsid subunit. Conversely, more than one foreign capsid subunit may be inserted or substituted into the parvovirus capsid. Likewise, a portion of a parvovirus capsid subunit or one or more parvovirus capsid subunits may be replaced with one or more foreign capsid subunits, or a portion thereof. Furthermore, the chimeric parvovirus capsid may contain insertions and/or substitutions at more than one site within the capsid. According to this embodiment, the multiple insertions/substitutions may be derived from more than one parvovirus (e.g., two, three, four, five or more). Generally, it is preferred that at least one subunit from the parvovirus capsid is retained in the chimeric capsid, although this is not required.

In particular embodiments of the invention, the foreign parvovirus capsid region that is inserted or substituted into the native parvovirus capsid is at least about 2, 5, 10, 12, 15, 20, 30, 50, or 100 amino acids in length.

The inventive chimeric parvoviruses may contain any parvovirus genome, preferably an AAV genome, more preferably a recombinant AAV genome. Embodiments wherein the AAV genome is packaged within a chimeric AAV capsid of the same serotype is also preferred. AAV type 2 genomes are most preferred regardless of the composition of the chimeric parvovirus capsid.

In preferred embodiments of the invention, the chimeric parvovirus comprises an AAV capsid, more preferably an AAV type 2 capsid, in which a capsid region from a B19 parvovirus has been substituted for one of the AAV capsid domains. In other preferred embodiments, the chimeric parvovirus comprises an AAV capsid (more preferably, an AAV type 2 capsid) in which the Vp3 subunit of the AAV capsid has been replaced by the B19 Vp2 subunit.

In alternative preferred embodiments, the chimeric parvovirus comprises an AAV capsid (preferably type 2) in which the Vp1 and Vp2 subunits are replaced by the Vp1 subunit of a B19 parvovirus.

In other preferred embodiments, the chimeric parvovirus comprises an AAV type 2 capsid in which the type 2 Vp1 subunit has been replaced by the Vp1 subunit from an AAV type 1, 3, 4, 5, or 6 capsid, preferably a type 3, 4, or 5 capsid. Alternatively, the chimeric parvovirus has an AAV type 2 capsid in which the type 2 Vp2 subunit has been replaced by the Vp2 subunit from an AAV type 1, 3, 4, 5, or 6 capsid, preferably a type 3, 4, or 5 capsid. Likewise, chimeric parvoviruses in which the Vp3 subunit from an AAV type 1, 3, 4, 5 or 6 (more preferably, type 3, 4 or 5) is substituted for the Vp3 subunit of an AAV type 2 capsid are preferred. As a further alternative, chimeric parvoviruses in which two of the AAV type 2 subunits are replaced by the subunits from an AAV of a different serotype (e.g., AAV type 1, 3, 4, 5 or 6) are preferred. In exemplary chimeric parvoviruses according to this embodiment, the Vp1 and Vp2, or Vp1 and Vp3, or Vp2 and Vp3 subunits of an AAV type 2 capsid are replaced by the corresponding subunits of an AAV of a different serotype (e.g., AAV type 1, 3, 4, 5 or 6). Likewise, in other preferred embodiments, the chimeric parvovirus has an AAV type 1, 3, 4, 5 or 6 capsid (preferably the type 2, 3 or 5 capsid) in which one or two subunits have been replaced with those from an AAV of a different serotype, as described above for AAV type 2.

In still other preferred embodiments, the minor subunit of one parvovirus may be substituted with any minor subunit of another parvovirus (e.g., Vp2 of AAV type 2 may be replaced with Vp1 from AAV type 3; Vp1 of B19 may substitute for Vp1 and/or VP2 of AAV). Likewise, the major capsid subunit of one parvovirus may be replaced with the major capsid subunit of another parvovirus.

The nucleotide sequences encoding specific chimeric capsids include the sequence given as nucleotides 2133 to 4315 of SEQ ID NO:2. This sequence contains the AAV2 rep coding sequences, most of the AAV2 Vp1 and Vp3 coding sequences, and the entire AAV4 Vp2 coding sequences and some of the AAV4 Vp1 and Vp3 coding sequences in a pBluescript backbone. Preferably, the chimeric parvoviruses having the capsid encoded by the helper given in SEQ ID NO:2 carry an AAV2 genome.

Alternatively, the nucleotide sequence of the chimeric capsid is substantially homologous to the capsid coding sequence given as nucleotides 2133 to 4315 of SEQ ID NO:2. As a further alternative, the nucleotide sequence of the chimeric capsid encodes the same amino acid sequence as nucleotides 2133 to 4315 of SEQ ID NO:2. The term "substantially homologous" is as defined hereinbelow.

The present invention also provides the discovery that chimeric parvoviruses may generate unique capsid structures that do not resemble the constituent parvovirus capsids. For example, the present investigations have discovered that B19/AAV type 2 chimeras, in which the Vp3 subunit of AAV type 2 has been replaced by the Vp2 subunit of a human B19 virus, results in the expected 23–28 nm particle (typical for wt AAV) and a novel 33–38 nm particle. The larger particles were present at the same density as the 23–28 nm particles in a cesium isopycnic gradient.

While not wishing to be held to any particular theory of the invention, these results suggest that this particle is formed by changing the triangulation number from T=1 to T=3, to yield a larger particle containing 180 copies of the major capsid component instead of 60. This novel particle may package larger than wild-type genomes due to its increased size. In particular preferred embodiments, the B19/AAV type 2 chimeric parvovirus capsid (B19 Vp2 swapped for AAV2 Vp3) has the amino acid sequence given as SEQ ID NO. 4.

The present invention further provides B19/AAV chimeric capsids and parvoviruses having larger than wild-type capsid structures (e.g., larger than about 28 nm, 30 nm, 32 nm, 34 nm, 36 nm, 38 nm, 40 nm or more in diameter). Alternatively stated, the present invention provides B19/AAV chimeric capsids and parvoviruses with capsid structures containing more than the wild-type number of capsid subunits (e.g., greater than about 60 capsid subunits, greater than about 90 capsid subunits, greater than about 120 capsid subunits, greater than about 180 capsid subunits). As a further alternative statement, the present invention provides B19/AAV capsids and parvoviruses that efficiently package greater than wild-type genomes (e.g., greater than about 4.8 kb, 5.0 kb, 5.2 kb, 5.4 kb, 5.6 kb, 5.8 kb, 6.0 kb, 6.2 kb, 6.4 kb, 6.6 kb, 6.8 kb or more). Preferably, the larger genomes are efficiently packaged to produce viral stocks having the titers described hereinabove.

It is also preferred that the B19/AAV chimeras have altered antigenic properties. In particular, it is preferred that the B19/AAV chimeras may be administered to a subject that has antibodies against the serotype of the AAV without immune clearance, i.e., the chimera is not recognized by the AAV serotype-specific antibodies.

In other preferred embodiment of the invention, the nucleotide sequence of the B19/AAV chimeric capsid is substantially homologous to the sequence given as SEQ ID NO:3 and encodes a chimeric parvovirus capsid. This definition is intended to include AAV of other serotypes and non-human B19 viruses. As used herein, sequences that are "substantially homologous" are at least 75%, and more preferably are 80%, 85%, 90%, 95%, or even 99% homologous or more.

High stringency hybridization conditions that permit homologous nucleotide sequences to hybridize are well known in the art. For example, hybridization of homologous nucleotide sequences to hybridize to the sequence given SEQ ID NO:3 may be carried out in 25% formamide, 5×SSC, 5× Denhardt's solution, with 100 µg/ml of single stranded DNA and 5% dextran sulfate at 42° C., with wash conditions of 25% formamide, 5×SSC, 0.1% SDS at 42° C. for 15 minutes, to allow hybridization of sequences of about 60% homology. More stringent conditions are represented by a wash stringency of 0.3M NaCl, 0.03 M sodium citrate, 0.1% SDS at 60° or even 70° C. using a standard in situ hybridization assay. (See SAMBROOK ET AL., MOLECULAR CLONING, A LABORATORY MANUAL (2d ed. 1989)).

In other preferred embodiments, the chimeric B19/AAV capsid has the amino acid sequence encoded by the sequence given in SEQ ID NO:3 (SEQ ID NO:4).

In other particular preferred embodiments, a non-conserved region(s) of a parvovirus capsid is inserted or substituted, preferably substituted, into another parvovirus capsid. Preferably a non-conserved region(s) is substituted for the same (i.e., homologous) region from a different parvovirus. Parvovirus specific (including AAV serotype specific) characteristics are likely associated with such non-conserved regions. It is also likely that non-conserved regions can best tolerate alterations. In particular embodiments, the looped-out regions of the parvovirus major capsid subunits are swapped between two parvoviruses, more preferably an AAV and a parvovirus, still more preferably between two AAV of different serotypes.

With particular respect to AAV type 2, although the crystal structure of this virus has not been solved, structural correlations have been made based on sequence information. The structural correlations suggest that the Vp3 subunit of AAV type 2 has eight β-barrel motifs, and that these motifs are separated by looped out regions (Chapman et al., *Virology* 194:419). Recently, the sequence of AAV type 3 has been determined by Muramatsu et al., (1996) *Virology* 221:208. The amino acid homology between Vp3 of AAV type 2 and AAV type 3 is 89%, with the region defined as loop 3/4 having 70% homology (Id.). Additionally, AAV type 3 does not bind to the same receptor as AAV type 2 (Mizukami et al., *Virology* 217:124). The divergent amino acid sequences in loops 3 and 4 may explain the differences in cellular receptors used by AAV type 2 and AAV type 3, and the resulting disparities in cellular tropism. Accordingly, in preferred embodiments of the instant invention, chimeric AAV particles are constructed in which loop 3/4, or a portion thereof, of AAV type 2 is swapped for the AAV type 3 loop 3/4, or vice versa.

In other embodiments, the chimeric parvovirus comprises an AAV type 2 capsid in which loop 1, 2, 3, and/or 4 of the Vp3 subunit have been replaced by the corresponding loop region(s) of an AAV of a different serotype (e.g., type 1, 3, 4, 5 or 6). In illustrative embodiments, the loop 2–4 region of the AAV type 2 Vp3 subunit is replaced by the loop 2–4 region of a type 3 or type 4 virus.

Likewise, in other preferred embodiments, the chimeric parvovirus comprises an AAV type 1, 3, 4, 5 or 6 capsid in which the loop 1, 2, 3 and/or 4 region of the Vp3 subunit is replaced by the corresponding region of a different AAV serotype. Exemplary embodiments include, but are not limited to, a chimeric parvovirus comprising an AAV type 3 or type 4 capsid in which the loop 2–4 region of the Vp3 subunit is replaced by the AAV type 2 loop 2–4 region.

The present invention further provides chimeric parvoviruses comprising an AAV capsid in which a loop region(s) in the major Vp3 subunit is replaced by a loop region (s) (preferably, a corresponding loop region(s)) from the major subunit of an autonomous parvovirus. In particular, the loop region 1, 2, 3 and/or 4 from an AAV type 1, 2, 3, 4, 5, or 6 Vp3 subunit is replaced with a loop region from the major subunit of an autonomous parvovirus.

The nucleotide sequence of specific chimeric capsids include the sequence give as nucleotides 2133 to 4342 of SEQ ID NO:5. This sequence contains the AAV2 rep coding sequences, most of the AAV2 capsid coding sequences, with the exception that loops 2–4 from the AAV2 Vp3 subunit were replaced with the corresponding region from AAV3, in a pBluescript backbone.

Alternatively, the nucleotide sequence of the chimeric capsid is substantially homologous to the sequence given as nucleotides 2133 to 4342 of SEQ ID NO:5. As a further alternative, the nucleotide sequence of the chimeric capsid has the same amino acid sequence as the capsid encoded by nucleotides 2133 to 4342 of SEQ ID NO:5. The term "substantially homologous" is as defined hereinabove.

Chimeric parvoviruses may be constructed as taught herein or by other standard methods known in the art. Likewise, those skilled in the art may evaluate the chimeric parvoviruses thus generated for assembly, packaging, cellular tropism, and the like, as described herein or by other standard methods known in the art, without undue experimentation.

Another aspect of the present invention is a chimeric parvovirus capsid protein (preferably an AAV Vp1, Vp2 or Vp3 capsid protein) with at least one capsid region from another parvovirus(es) inserted or substituted therein (preferably, substituted). The introduction of the foreign capsid protein into a parvovirus capsid provides altered characteristics (e.g., immunogenic, tropism, etc.) to a virus capsid or particle (preferably a parvovirus capsid or particle) incorporating the chimeric parvovirus capsid protein. Alternatively, the chimeric parvovirus capsid protein may facilitate detection or purification of a virus capsid or particle (preferably parvovirus capsid or particle) incorporating the chimeric parvovirus capsid protein. In particular preferred embodiments, the antigenic properties of an AAV capsid or particle of a particular serotype may be altered (e.g., changed or modified) or diminished (e.g., reduced or mitigated) by incorporation of the chimeric parvovirus capsid region for the native capsid region. According to this embodiment, chimeric capsid proteins may be used to obviate or reduce immune clearance in subjects that have immunity against the serotype of the AAV capsid or particle (e.g., to permit multiple virus administrations). Changes or reductions in antigenic properties may be assessed, e.g., in comparison to an AAV capsid or particle that is identical except for the presence of the chimeric parvovirus capsid protein.

The present invention also encompasses empty chimeric parvovirus capsid structures. Empty capsids may be used for presentation or delivery of peptides or proteins (e.g., antigens to produce an immune response), nucleic acids, or other compounds (see, e.g., Miyamura et al., (1994) *Proc. Nat. Acad. Sci USA* 91:8507; U.S. Pat. No. 5,916,563 to Young et al., U.S. Pat. No. 5,905,040 to Mazzara et al., U.S. Pat. Nos. 5,882,652, 5,863,541 to Samulski et al.; the disclosures of which are incorporated herein in their entirety by reference). Empty capsids may be produced by any method known in the art. (see, e.g., id.).

The chimeric parvoviruses and capsids of the invention further find use in raising antibodies against the novel capsid structures. Antibodies may be produced by methods that are known to those skilled in the art.

The present invention also provides cloning vectors, transcomplementing packaging vectors, packaging cells, and methods for producing the inventive chimeric parvovirus particles disclosed herein. In general, vectors, packaging cells, and methods for producing chimeric parvoviruses are as described above with respect to hybrid parvoviruses. In addition, at least one of the cap genes (encoded by the rAAV genome, a packaging vector(s), or the packaging cell) has inserted therein at least one nucleic acid sequence encoding a foreign amino acid sequence from a non-homolgous parvovirus (as described above).

III. Targeted Parvoviruses.

A further aspect of the present invention are parvovirus vectors comprising a parvovirus capsid and a recombinant AAV genome, wherein an exogenous targeting sequence has been inserted or substituted into the parvovirus capsid. The parvovirus vector is preferably targeted (i.e., directed to a particular cell type or types) by the substitution or insertion of the exogenous targeting sequence into the parvovirus capsid. Alternatively stated, the exogenous targeting sequence preferably confers an altered tropism upon the parvovirus. As yet a further alternative statement, the targeting sequence increases the efficiency of delivery of the targeted vector to a cell.

As, is described in more detail below, the exogenous targeting sequence may be a virus capsid sequence (e.g., an autonomous parvovirus capsid sequence, AAV capsid sequence, or any other viral capsid sequence) that directs infection of the parvovirus to a particular cell type(s). As an alternative, the exogenous amino acid sequence may encode any peptide or protein that directs entry of the parvovirus vectors into a cell(s). In preferred embodiments, the parvovirus capsid is an AAV capsid, more preferably, an AAV type 2 capsid.

An "altered" tropism, as used herein, includes reductions or enhancements in infectivity with respect to a particular cell type(s) as compared with the native parvovirus lacking the targeting sequence(s). An "altered" tropism also encompasses the creation of a new tropism (i.e., the parvovirus would not infect a particular cell type(s) to a significant or, alternatively, a detectable extent in the absence of the exogenous amino acid sequence). Alternatively, an "altered" tropism" may refer to a more directed targeting of the parvovirus vector to a particular cell type(s) as compared with the native parvovirus, but the target cells may typically be infected by the native parvovirus as well (e.g., a narrowed tropism). As a further alternative, an "altered" tropism refers to a more efficient delivery of a targeted parvovirus as compared with the native parvovirus (e.g., a reduced Multiplicity of Infection, "MOI").

The term "reduction in infectivity", as used herein, is intended to encompass both an abolishment of the wild-type tropism as well as a diminishment in the wild-type tropism or infectivity toward a particular cell type(s). The diminished infectivity may be a 25%, 50%, 75%, 90%, 95%, 99%, or more decrease in infectivity with respect to the wild-type level of infectivity. By "enhancement in infectivity", it is meant that the infectivity with respect to a particular cell type(s) is increased above that observed with the wild-type parvovirus, e.g., by at least 25%, 50%, 75%, 100%, 150%, 200%, 300%, or 500%, or more.

The exogenous targeting sequence(s) may replace or substitute part or all of a capsid subunit, alternatively, more than one capsid subunit. As a further alternative, more than one exogenous targeting sequence (e.g., two, three, four, five or more sequences) may be introduced into the parvovirus capsid. In alternative embodiments, insertions and substitutions within the minor capsid subunits (e.g., Vp1 and Vp2 of AAV) are preferred. For AAV capsids, insertions or substitutions in Vp2 or Vp3 are also preferred.

Those skilled in the art will appreciate that due to the overlap in the sequences encoding the parvovirus capsid proteins, a single insertion or substitution may affect more than one capsid subunit.

As described above, in particular embodiments, the present invention provides chimeric parvovirus particles with unique structures and properties. The substitution and/or insertion of one or more parvovirus capsid region(s) for another to create a chimeric parvovirus capsid may result in the loss of the wild-type parvovirus tropism and/or the development of a new tropism associated with the exogenous capsid region(s). Accordingly, targeted parvoviruses may also be chimeric parvoviruses as is described in more detail hereinabove. In particular, targeted chimeric parvoviruses are provided in which a capsid subunit(s) or a loop region(s) from the major capsid subunit has been replaced with a capsid subunit(s) or loop region from another parvovirus.

Accordingly, in particular embodiments of the instant invention, chimeric parvovirus particles are constructed in which the capsid domains that encode the wild-type parvovirus tropism are swapped with capsid regions or subunits from a different parvovirus sequence, thereby diminishing or even completely abolishing the wild-type tropism. These infection-negative parvoviruses find use as templates for creating parvoviruses with targeted tropisms. In this manner, a parvovirus with a new or directed tropism, but lacking the wild-type tropism, may be generated.

In another preferred embodiment, a parvovirus capsid region that directs the native or wild-type tropism is swapped with a capsid domain that directs the tropism of another parvovirus, thereby diminishing or ablating the native tropism and concurrently conferring a new tropism to the chimeric parvovirus. In other embodiments, the foreign capsid region is substituted or inserted into the parvovirus capsid without reducing or extinguishing the wild-type tropism. As a further alternative, more than one foreign parvovirus capsid region (e.g., two, three, four, five, or more) is swapped into the parvovirus capsid. For example, a first foreign capsid region may replace the native capsid region directing the wild-type tropism. Additional foreign capsid regions provide the chimeric capsid with a new tropism(s).

Heparan sulfate (HS) has recently been identified as a primary receptor for AAV (Summerford and Samulski, (1998) *J. Virology* 72:1438). Thus, the capsid structure may be modified to facilitate or enhance binding of AAV to the cellular receptor or to inhibit or prevent binding thereto. To illustrate, the tropism of the AAV may be altered by swapping out the HS binding domain for the AAV capsid, for example, with sequences from other parvoviruses that do contain this HS binding domain or any other sequences.

Several consensus sequences have been identified among ligands that bind to HS receptors. In general, HS appears to bind to sequences including clusters of basic amino acids. Illustrative consensus sequences include but are not limited to BBXB, BBBXXB, and $RX_7FRXKKXXXK$, where B is a basic amino acid, and X is any amino acid. Three sequences containing clusters of basic amino acids are present in the first 170 amino acid residues of the VP1 capsid protein of AAV type 2 as follows: $RX_5KKR$ at amino acids 116 to 124, $KX_4KKR$ at amino acids 137 to 144, and $KX_6RKR$ at amino acids 161 to 170 (AAV type 2 sequence and numbering as described by Srivastava et al., (1983) *J. Virology* 45:555, as modified by Ruffing et al., (1994) *J. Gen. Virology* 75:3385, Muzyczka, (1992) *Curr. Topics Microbiol. Immunol.* 158:97, and Cassinofti et al., (1988) *Virology* 167:176). In addition, the consensus sequence ($RX_7FRPKRLNFK$) is found in the VP1 capsid subunit of AAV type 2 at amino acids 299 to 315.

It appears that AAV serotypes 4 and 5 do not bind to cellular HS receptors, or do so with a low efficiency. Accordingly, in particular embodiments, the HS binding domain of AAV serotypes 1, 2, 3, or 6 may be replaced with the corresponding region of AAV serotype 4 or 5 to reduce or abolish HS binding. Likewise, HS binding may be conferred upon AAV serotype 4 or 5 by inserting or substituting in the HS binding domain from AAV 1, 2, 3 or 6.

The HS consensus sequences are marked by an abundance of basic amino acids. There is a high density of positively charged amino acids within the first 170 residues of the AAV type 2 Vp1 Cap protein, including three strings of basic amino acids, which may be involved in an ionic interaction with the cell surface. Accordingly, in one particular embodiment of the invention, the affinity of an AAV capsid for HS receptors is reduced or eliminated by creating a targeted parvovirus in which some or all of the basic sequences are substituted by other sequences, e.g., from another parvovirus that does not contain the HS binding domain.

Alternatively, the respiratory syncytial virus heparin binding domain may be inserted or substituted into a virus that does not typically bind HS receptors (e.g., AAV 4, AAV5, B19) to confer heparin binding to the resulting mutant.

B19 infects primary erythroid progenitor cells using globoside as its receptor(Brown et al., (1993) *Science* 262:114). The structure of B19 has been determined to 8 Å resolution (Agbandje-McKenna et al., (1994) *Virology* 203:106). The region of the B19 capsid that binds to globoside has been mapped between amino acids 399–406 (Chapman et al., (1993) *Virology* 194:419), a looped out region between β-barrel structures E and F (Chipman et al., (1996) *Proc. Nat Acad. Sci. USA* 93:7502). Accordingly, the globoside receptor binding domain of the B19 capsid may be inserted/substituted into other parvovirus capsids (preferably an AAV capsid, more preferably, the AAV type 2 capsid) to target the resulting chimeric parvovirus to erythroid cells.

In more preferred embodiments, the exogenous targeting sequence may be any amino acid sequence encoding a peptide or protein, which is inserted or substituted into the parvovirus capsid to alter the tropism of the parvovirus. The native parvovirus tropism may be reduced or abolished by insertion or substitution of the amino acid sequence. Alternatively, the insertion or substitution of the exogenous amino acid sequence may target the parvovirus to a particular cell type(s). In yet further preferred embodiments, an exogenous targeting sequence is substituted or inserted into the parvovirus capsid to concurrently ablate the wild type tropism and to introduce a new tropism. For example, a targeting peptide may be inserted directly into a targeting region of the AAV capsid to simultaneously disrupt the native tropism (e.g., by interfering with binding to-cellular heparan sulfate receptors) and to direct the targeted AAV vector to particular cells.

Those skilled in the art will appreciate that the native tropism of a parvovirus may be reduced or abolished without substituting or inserting an exogenous targeting sequence directly into those regions of the parvovirus capsid responsible for the receptor binding. Mutants that have lost the wild-type tropism are useful as templates for the creation of parvoviruses with novel tropisms as taught herein. It is preferred that substitutions or insertions that result in the loss of wild-type tropism act at the level of receptor binding and/or entry into the cell. In other words, it is preferred that the altered parvovirus is otherwise capable of infecting a cell if entry into the cell is provided by other means, e.g., by a bispecific antibody, by targeting peptide or protein as disclosed herein, or by any other means known in the art.

The exogenous targeting sequence may be any amino acid sequence encoding a protein or peptide that alters the tropism of the parvovirus. In particular embodiments, the targeting peptide or protein may be naturally occurring or, alternately, completely or partially synthetic. Exemplary peptides and proteins include ligands and other peptides that bind to cell surface receptors and glycoproteins, such as RGD peptide sequences, bradykinin, hormones, peptide growth factors (e.g., epidermal growth factor, nerve growth factor, fibroblast growth factor, platelet-derived growth factor, insulin-like growth factors I and II, etc.), cytokines, melanocyte stimulating hormone (e.g., α, β or γ), neuropeptides and endorphins, and the like, and fragments thereof that retain the ability to target cells to their cognate receptors. Other illustrative peptides and proteins include substance P, keratinocyte growth factor, neuropeptide Y, gastrin releasing peptide, interleukin 2, hen egg white lysozyme, erythropoietin, gonadoliberin, corticostatin, β-endorphin, leu-enkephalin rimorphin, α-neo-enkephalin, angiotensin, pneumadin, vasoactive intestinal peptide, neurotensin, motilin, and fragments thereof as described above. As a further alternative, the targeting peptide or protein may be an antibody or Fab fragment that recognizes, e.g., a cell-surface epitope, such as an anti-receptor antibody. As yet a further alternative, the binding domain from a toxin (e.g., tetanus toxin or snake toxins, such as α-bungarotoxin, and the like) can be used to target the inventive parvovirus vectors to particular target cells of interest. In a yet further preferred embodiment the parvovirus vectors may be delivered to a cell using a "nonclassical" importexport signal peptide (e.g., fibroblast growth factor-1 and -2, interleukin 1, HIV-1 Tat protein, herpes virus VP22 protein, and the like) as described by Cleves, (1997) *Current Biology* 7:R318. Also encompassed are peptide motifs that direct uptake by specific cells, e.g., a FVFLP peptide motif triggers uptake by liver cells. Phage display techniques, as well as other techniques known in the art, may be used to identify peptides that recognize, preferably specifically, any cell type of interest.

The term "antibody" as used herein refers to all types of immunoglobulins, including IgG, IgM, IgA, IgD, and IgE. The antibodies may be monoclonal or polyclonal and may be of any species of origin, including (for example) mouse, rat, rabbit, horse, or human, or may be chimeric antibodies. Also encompassed by the term "antibody" are bispecific or "bridging" antibodies as known by those skilled in the art.

Antibody fragments within the scope of the present invention include, for example, Fab, F(ab)2, and Fc fragments, and the corresponding fragments obtained from antibodies other than IgG. Such fragments may be produced by known techniques.

The targeting sequence may alternatively encode any peptide or protein that targets the parvovirus particle to a cell surface binding site, including receptors (e.g., protein, carbohydrate, glycoprotein or proteoglycan), as well as any oppositely charged molecule (as compared with the targeting sequence or the parvovirus capsid), or other molecule with which the targeting sequence or targeted parvovirus interact to bind to the cell, and thereby promote cell entry. Examples of cell surface binding sites include, but are not limited to, heparan sulfate, chondroitin sulfate, and other glycosaminoglycans, sialic acid moieties found on mucins, glycoproteins, and gangliosides, MHCl glycoproteins, carbohydrate components found on membrane glycoproteins, including, mannose, N-acetyl-galactosamine, N-acetyl-glucosamine, fucose, galactose, and the like.

As yet a further alternative, the targeting sequence may be a peptide or protein that may be used for chemical coupling (e.g., through amino acid side groups of arginine or lysine residues) to another molecule that directs entry of the parvovirus into a cell.

In other embodiments, the exogenous targeting sequence is substituted or inserted into the capsid to disrupt binding to cellular receptors (e.g., HS receptor) and/or entry into the cell. For example, the exogenous amino acid sequence may be substituted or inserted into the region(s) of the AAV capsid that binds to cellular receptors and/or otherwise mediates entry of the virus into the cell. Preferably, the exogenous targeting sequence is inserted into the capsid region(s) that interact with cellular HS receptors (as described above). One illustrative insertion mutant that forms intact AAV virions yet fails to bind heparin agarose or infect Hela cells is an AAV type 2 mutant generated by insertion of an amino acid sequence at bp 3761 of the AAV type 2 genome (within the Vp3 cap gene region).

In a further alternative embodiment, the exogenous amino acid sequence inserted into the parvovirus capsid may be one that facilitates purification of the parvovirus. According to this aspect of the invention, it is not necessary that the exogenous amino acid sequence also alters the tropism of the modified parvovirus. For example, the exogenous amino acid sequence may include a poly-histidine sequence that is useful for purifying the parvovirus over a nickel column, as is known to those skilled in the art. Alternatively, the region of the AAV capsid that interacts with heparin and/or heparan sulfate may be substituted or inserted into a parvovirus capsid so that the parvovirus may be purified by binding to heparin, e.g., as described by Zolotukhin et al., (1999) *Gene Therapy* 6:973, the disclosure of which is incorporated herein in its entirety by reference.

In other embodiments, the amino acid sequence encodes an antigenic peptide or protein that may be employed to purify the AAV by standard immunopurification techniques. Alternatively, the amino acid sequence may encode a receptor ligand or any other peptide or protein that may be used to purify the modified parvovirus by affinity purification or any other techniques known in the art (e.g., purification techniques based on differential size, density, charge, or isoelectric point, ion-exchange chromatography, or peptide chromatography).

In yet other embodiments of the invention, an amino acid sequence may be inserted or substituted into a parvovirus particle to facilitate detection thereof (e.g., with a antibody or any other detection reagent, as is known in the art). For example, the "flag" epitope may be inserted into the parvovirus capsid and detected using commercially-available antibodies (Eastman-Kodak, Rochester, N.Y.). Detectable viruses find use, e.g., for tracing the presence and/or persistence of virus in a cell, tissue or subject.

In still a further embodiment, an exogenous amino acid sequence encoding any antigenic protein may be expressed in the modified capsid (e.g., for use in a vaccine).

As described below and in Table 1, the present investigations have used insertional mutagenesis of the capsid coding sequence of AAV serotype 2 in order to determine positions within the capsid that tolerate peptide insertions. Viable mutants were identified with insertions throughout each of the capsid subunits. These insertion mutants find use for any purpose in which it is desirable to insert a peptide or protein sequence into an AAV capsid, e.g., for purifying and/or detecting virus, or for inserting an antigenic peptide or protein into the capsid. The nucleotide positions indicated in Table 1 (see Examples) are the positions at which the restriction sites were made, e.g., the new sequences start at the next nucleotide. For example, for an insertion mutant indicated in Table 1 as having an insertion at nucleotide 2285, the new insertion sequence would begin at nucleotide 2286.

It is preferred to insert the exogenous amino acid sequence within the parvovirus minor Cap subunits, e.g., within the AAV Vp1 and Vp2 subunits. Alternately, insertions in Vp2 or Vp3 are preferred. Also preferred are insertion mutations at nucleotide 2285, 2356, 2364, 2416, 2591, 2634, 2690, 2747, 2944, 3317, 3391, 3561, 3595, 3761, 4046, 4047, and/or 4160 within the AAV type 2 cap genes, preferably, to generate an AAV type 2 vector with an altered tropism as described herein (AAV type 2 numbering used herein is as described by Srivastava et al., (1983) *J. Virology* 45:555, as modified by Ruffing et al., (1994) *J. Gen. Virology* 75:3385, Muzyczka, (1992) *Curr. Topics Microbiol. Immunol.* 158:97, and Cassinofti et al., (1988) *Virology* 167:176).

Insertions at these nucleotide positions for AAV2 will give rise to amino acid insertions following amino acid 28 (nu 2285), 51 (nu 2356), 54 (nu 2364), 71 (nu 2416), 130 (nu 2591), 144 (nu 2634), 163 (nu 2690), 182 (nu 2747), 247 (nu 2944), 372 (nu 3317), 396 (nu 3391), 452 (nu 3561), 464 (nu 3595), 520 (nu 3761), 521 (nu 3766), 615 (nu 4046 and 4047), and 653 (nu 4160) within the AAV2 capsid coding region (using the starting methionine residue for Vp1 as amino acid 1), or the corresponding regions of AAV of other serotypes as known by those skilled in the art. Those skilled in the art will appreciate that due to the overlap in the AAV capsid coding regions, these insertions may give rise to insertions within more than one of the capsid proteins (Table 2).

TABLE 2

Insertion Positions in AAV2 CaDsid[1, 2]

| Insertion site (nucleotide) | Vp1 (amino acid) | Vp2 (amino acid) | Vp3 (amino acid) |
|---|---|---|---|
| 2285 | 28 | — | — |
| 2356 | 51 | — | — |
| 2364 | 54 | — | — |
| 2416 | 71 | — | — |
| 2591 | 130 | — | — |
| 2634 | 144 | 7 | — |
| 2690 | 163 | 26 | — |
| 2747 | 182 | 45 | — |
| 2944 | 247 | 110 | 45 |
| 3317 | 372 | 235 | 170 |
| 3391 | 396 | 259 | 194 |
| 3561 | 452 | 315 | 250 |
| 3595 | 464 | 327 | 262 |
| 3753 | 517 | 380 | 315 |
| 3761 | 520 | 383 | 318 |
| 3766 | 521 | 384 | 319 |
| 3789 | 529 | 392 | 327 |
| 3858 | 552 | 415 | 350 |
| 3960 | 586 | 449 | 384 |
| 3961 | 586 | 449 | 384 |
| 3987 | 595 | 458 | 393 |
| 4046 | 615 | 478 | 413 |
| 4047 | 615 | 478 | 413 |
| 4160 | 653 | 516 | 451 |

[1]The indicated nucleotide or amino acid refers to the nucleotide or amino acid immediately preceding the inserted sequence.
[2]Vp1 start at nucleotide 2203

Alternatively, the exogenous amino acid sequence is inserted at the homologous sites to those described above in AAV capsids of other serotypes as known by those skilled in the art (see, e.g., Chiorini et al., (1999) *J. Virology* 73:1309). The amino acid positions within the AAV capsid appear to be highly, or even completely, conserved among AAV serotypes. Accordingly, in particular embodiments, the exogenous amino acid sequence is substituted at the amino acid positions indicated in Table 2 (new sequence starting at the next amino acid) in AAV other than serotype 2 (e.g., serotype 1, 3, 4, 5 or 6).

As further alternatives, an exogenous amino acid sequence may be inserted into the AAV capsid at the positions described above to facilitate purification and/or detection of the modified parvovirus or for the purposes of antigen presentation, as described above.

One particular AAV type 2 mutant is produced by inserting an amino acid sequence at nucleotide position 2634 of the genome (within the Vp2 cap gene region; AAV2 numbering as described above). This mutant forms AAV type 2 virions with normal morphology by electron microscopy analysis in the absence of detectable expression of the Vp1 and Vp2 subunits. Moreover, this mutant protects the viral genome and retains binding to a heparin-agarose matrix, although it does not demonstrate infectivity in HeLa cells. This mutant is useful for administration to subjects to avoid an immune response against the Vp1 and Vp2 subunits. It further finds use for insertion of large peptides or proteins into the AAV capsid structure. As one illustrative example, the adenovirus knob protein is inserted into this mutant to target the virus to the Coxsackie adenovirus receptor (CAR).

Another particular AAV type 2 insertion mutant is produced by insertion of an exogenous amino acid sequence at bp 3761 of the genome (within the Vp3 capsid coding region). This mutant protects the viral genome and forms morphologically normal capsid structures, but does not bind heparin-agarose and fails to infect HeLa cells. This mutant is particularly useful as a reagent for creating AAV vectors lacking the native tropism. For example, a new targeting region may be introduced into this mutant at bp 3761 or at another site. As shown in Table 1, the present investigations have discovered a variety of positions within the AAV capsid that tolerate insertion of exogenous peptides and retain infectivity (e.g., at bp 2356, 2591, 2690, 2944, 3595, and/or 4160 of the AAV type 2 genome).

In other preferred embodiments, AAV vectors with multiple insertions and/or substitutions are created to provide AAV vectors exhibiting a desired pattern of infectivity, e.g., a non-infectious insertion/substitution mutation and an infectious mutation (e.g., as shown in Table 1) may be combined in a single AAV vector. As one illustrative example, a peptide insertion may be made at bp 3761 of the AAV type 2 genome (within the Vp3 subunit) to create a non-infectious heparin binding negative mutant. A second peptide insertion may be made at bp 2356 (alternatively, bp 2591, 2690, 2944, 3595 or 4160) to target the vector. The inserted peptide may be one that directs the AAV type 2 vector to target cells of interests. In particular embodiments, bradykinin may be inserted at any of the foregoing sites to target the vector to lung epithelial cells (e.g., for the treatment of cystic fibrosis or other lung disorders) or the adenovirus knob protein may be inserted at the foregoing sites to target the vector to cells expressing CAR receptors. Alternatively, this vector may be employed for antigen presentation to produce an immune response.

In other embodiments, the substitution or insertion (preferably insertion) is made at nucleotides 3789 or 3961 of the AAV2 genome (e.g., new sequence would start at nu 3790 and 3962, respectively), or the corresponding site of other AAV serotypes as known by those skilled in the art. These positions correspond to insertions following amino acid 529 and 586, respectively, of the AAV2 capsid (Met #1 of Vp1 as amino acid 1; Table 2). In particular embodiments, there will be missense mutation at nucleotides 3790–3792 (Glu→Ile) or at nucleotides 3960–3961 (Gly→Val), respectively, due to the creation of a restriction site as part of the cloning strategy. In preferred embodiments of the invention, a targeting insertion at nu 3789 or 3961 is combined with the 3761 mutation, which results in loss of heparin binding, to create a targeted capsid or parvovirus.

In other preferred embodiments an insertion or substitution (preferably, insertion) is made in the AAV2 capsid at nucleotides 3753, 3858, 3960, or 3987 (new sequence beginning at the next nucleotide), or the corresponding sites in AAV of other serotypes. These sites correspond to insertions or substitutions following amino acids 517, 552, 586, or 595, respectively, of the AAV2 capsid (Met #1 of Vp1 as amino acid 1; Table 2), or the corresponding sites in AAV capsids of other serotypes as known by those skilled in the art.

In other preferred embodiments, the insertion or substitution is made following amino acid 517, 529, 552, 586 or 595 of AAV capsids of other serotypes, e.g. (1, 2, 3, 5 or 6).

There is no particular lower or upper limit to the length of the amino acid sequence that may be inserted or substituted into the virus capsid, as long as the targeted or modified parvovirus capsid retains the desired properties (e.g., assembly, packaging, infectivity). The exogenous amino acid sequence may be as short as 100, 50, 20,16, 12, 8, 4 or 2 amino acids in length. Similarly, the exogenous amino acid sequence to be inserted/substituted into the parvovirus capsid may be as long as 2, 5, 10, 12, 15, 20, 50, 100, 200, 300 or more amino acids. In particular embodiments, the exogenous amino acid sequence encodes an entire protein. Preferably, the exogenous amino acid sequence that is inserted/substituted into the parvovirus capsid is expressed on the outside surface of the modified parvovirus capsid.

The present invention further provides targeted parvovirus capsid proteins, whereby a targeting sequence(s) is inserted or substituted into a parvovirus capsid protein, as described above. The targeted parvovirus capsid protein confers an altered tropism upon a virus vector or virus capsid (preferably, a parvovirus vector or capsid) incorporating the targeted parvovirus capsid protein therein as compared with the tropism of the native virus vector or virus capsid in the absence of the targeted parvovirus capsid protein. Likewise, modified capsid proteins (modifications as described above for parvoviruses) are another aspect of the invention. The modified capsid protein may be incorporated into a parvovirus capsid or particle, e.g., to facilitate purification and/or detection thereof or for the purposes of antigen presentation.

Further provided are targeted and/or modified parvovirus capsids as described in more detail above in connection with chimeric parvovirus capsids. In particular embodiments, the present invention provides targeted parvovirus "capsid vehicles", as has been described for AAV capsids, e.g., U.S. Pat. No. 5,863,541.

Molecules that may be packaged by the inventive parvovirus capsids and transferred into a cell include recombinant AAV genomes, which may advantageously may then integrate into the target cell genome, and other heterologous DNA molecules. RNA, proteins and peptides, or small organic molecules, or combinations of the same. Heterologous molecules are defined as those that are not naturally found in an parvovirus infection, i.e., those not encoded by the parvovirus genome. In a preferred embodiment of the present invention, a DNA sequence to be encapsidated may be linked to an AAV ITR sequence that contains the viral packaging signals, which may increase the efficiency of encapsidation and/or targeted integration into the genome.

The invention is further directed to the association of therapeutically useful molecules with the outside of the inventive parvovirus capsids for transfer of the molecules into host target cells. Such associated molecules may include DNA, RNA, carbohydrates, lipids, proteins or peptides. In one embodiment of the invention the therapeutically useful molecules is covalently linked (i.e., conjugated or chemically coupled) to the capsid proteins. Methods of covalently linking molecules are known by those skilled in the art.

The targeted and/or modified parvovirus capsid proteins, capsids, and virus particles of the invention find use for raising antibodies against these novel capsid structures. Alternatively, an exogenous amino acid sequence may be inserted into the parvovirus capsid for antigen presentation to a cell, e.g. for administration to a subject to produce an immune response to the exogenous amino acid sequence. According to this latter embodiment, it is not necessary that the exogenous amino acid sequence also alter the tropism of the parvovirus.

It will be appreciated by those skilled in the art that modified/targeted viruses and capsids as described above may also be chimeric and/or hybrid parvoviruses as described in the preceding sections. Those skilled in the art will further appreciate that the insertion mutants described herein include parvoviruses with other modifications, e.g., deletion, insertion or missense mutations. In addition, the mutations may incidentally be introduced into the parvovirus capsid or rAAV genome as a result of the particular cloning strategy employed.

Parvoviruses, AAV, and rAAV genomes are as described above with respect to hybrid parvoviruses. The present invention also provides cloning vectors, transcomplementing packaging vectors, packaging cells, and methods for producing the modified and/or targeted rAAV particles described above. In general, helpers, packaging cells, and methods for producing the targeted or modified parvoviruses are as described above with respect to hybrid and chimeric viruses. In addition, at least one of the cap genes (encoded by the rAAV genome, a packaging vector, or the packaging cell) has inserted or substituted therein at least one nucleic acid sequence encoding an exogenous targeting sequence (as described above) or an exogenous amino acid sequence (as described above, e.g., for purification, detection or antigen presentation).

IV. Gene Transfer Technology.

The methods of the present invention provide a means for delivering heterologous nucleic acid sequences into a broad range of host cells, including both dividing and non-dividing cells. The vectors and other reagents, methods and pharmaceutical formulations of the present invention are additionally useful in a method of administering a protein or peptide to a subject in need thereof, as a method of treatment or otherwise. In this manner, the protein or peptide may thus be produced in vivo in the subject. The subject may be in need of the protein or peptide because the subject has a deficiency of the protein or peptide, or because the production of the protein or peptide in the subject may impart some therapeutic effect, as a method of treatment or otherwise, and as explained further below.

In general, the present invention may be employed to deliver any foreign nucleic acid with a biological effect to treat or ameliorate the symptoms associated with any disorder related to gene expression. Illustrative disease states include, but are not limited to: cystic fibrosis (and other diseases of the lung), hemophilia A, hemophilia B, thalassemia, anemia and other blood disorders, AIDs, Alzheimer's disease, Parkinson's disease, Huntington's disease, amyotrophic lateral sclerosis, epilepsy, and other neurological disorders, cancer, diabetes mellitus, muscular dystrophies (e.g., Duchenne, Becker), Gaucher's disease, Hurler's disease, adenosine deaminase deficiency, glycogen storage diseases and other metabolic defects, retinal degenerative diseases (and other diseases of the eye), diseases of solid organs (e.g., brain, liver, kidney, heart), and the like.

Gene transfer has substantial potential use in understanding and providing therapy for disease states. There are a number of inherited diseases in which defective genes are known and have been cloned. In some cases, the function of these cloned genes is known. In general, the above disease states fall into two classes: deficiency states, usually of enzymes, which are generally inherited in a recessive manner, and unbalanced states, at least sometimes involving regulatory or structural proteins, which are inherited in a dominant manner. For deficiency state diseases, gene transfer could be used to bring a normal gene into affected tissues for replacement therapy, as well as to create animal models for the disease using antisense mutations. For unbalanced disease states, gene transfer could be used to create a disease state in a model system, which could then be used in efforts to counteract the disease state. Thus the methods of the present invention permit the treatment of genetic diseases. As used herein, a disease state is treated by partially or wholly remedying the deficiency or imbalance that causes the disease or makes it more severe. The use of site-specific integration of nucleic sequences to cause mutations or to correct defects is also possible.

The instant invention may also be employed to provide an antisense nucleic acid to a cell in vitro or in vivo. Expression of the antisense nucleic acid in the target cell diminishes expression of a particular protein by the cell. Accordingly, antisense nucleic acids may be administered to decrease expression of a particular protein in a subject in need thereof. Antisense nucleic acids may also be administered to cells in vitro to regulate cell physiology, e.g., to optimize cell or tissue culture systems. The present invention is also useful to deliver other non-translated RNAs, e.g., ribozymes (e.g., as described in U.S. Pat. No. 5,877,022), RNAs that effect spliceosome-mediated trans-splicing (Puttaraju et al., (1999) *Nature Biotech.* 17:246), or "guide" RNAs (see, e.g., Gorman et al., (1998) *Proc. Nat. Acad. Sci. USA* 95:4929; U.S. Pat. No. 5,869,248 to Yuan et al.) to a target cell.

Finally, the instant invention finds further use in diagnostic and screening methods, whereby a gene of interest is transiently or stably expressed in a cell culture system, or alternatively, a transgenic animal model.

V. Subjects, Pharmaceutical Formulations, Vaccines, and Modes of Administration.

The present invention finds use in both veterinary and medical applications. Suitable subjects include both avians and mammals, with mammals being preferred. The term "avian" as used herein includes, but is not limited to, chickens, ducks, geese, quail, turkeys and pheasants. The term "mammal" as used herein includes, but is not limited to, humans, bovines, ovines, caprines, equines, felines, canines, lagomorphs, etc. Human subjects are the most preferred. Human subjects include fetal, neonatal, infant, juvenile and adult subjects.

In particular embodiments, the present invention provides a pharmaceutical composition comprising a virus particle of the invention in a pharmaceutically-acceptable carrier or other medicinal agents, pharmaceutical agents, carriers, adjuvants, diluents, etc. For injection, the carrier will typically be a liquid. For other methods of administration, the carrier may be either solid or liquid, such as sterile, pyrogen-free water or sterile pyrogen-free phosphate-buffered saline solution. For inhalation administration, the carrier will be respirable, and will preferably be in solid or liquid particulate form. As an injection medium, it is preferred to use water that contains the additives usual for injection solutions, such as stabilizing agents, salts or saline, and/or buffers.

In other embodiments, the present invention provides a pharmaceutical composition comprising a cell in which an AAV provirus is integrated into the genome in a pharmaceutically-acceptable carrier or other medicinal agents, pharmaceutical agents, carriers, adjuvants, diluents, etc.

By "pharmaceutically acceptable" it is meant a material that is not biologically or otherwise undesirable, e.g., the material may be administered to a subject without causing any undesirable biological effects. Thus, such a pharmaceutical composition may be used, for example, in transfection of a cell ex vivo or in administering a viral particle or cell directly to a subject.

The parvovirus vectors of the invention maybe administered to elicit an immunogenic response (e.g., as a vaccine). Typically, vaccines of the present invention comprise an immunogenic amount of infectious virus particles as disclosed herein in combination with a pharmaceutically-acceptable carrier. An "immunogenic amount" is an amount of the infectious virus particles that is sufficient to evoke an immune response in the subject to which the pharmaceutical formulation is administered. Typically, an amount of about $10^3$ to about $10^{15}$ virus particles, preferably about $10^4$ to about $10^{10}$, and more preferably about $10^4$ to $10^6$ virus particles per dose is suitable, depending upon the age and species of the subject being treated, and the immunogen against which the immune response is desired. Subjects and immunogens are as described above.

The present invention further provides a method of delivering a nucleic acid to a cell. For in vitro methods, the virus -may be administered to the cell by standard viral transduction methods, as are known in the art. Preferably, the virus particles are added to the cells at the appropriate multiplicity of infection according to standard transduction methods appropriate for the particular target cells. Titers of virus to administer can vary, depending upon the target cell type and the particular virus vector, and may be determined by those of skill in the art without undue experimentation. Alternatively, administration of a parvovirus vector of the present invention can be accomplished by any other means known in the art.

Recombinant virus vectors are preferably administered to the cell in a biologically-effective amount. A "biologically-effective" amount of the virus vector is an amount that is sufficient to result in infection (or transduction) and expression of the heterologous nucleic acid sequence in the cell. If the virus is administered to a cell in vivo (e.g., the virus is administered to a subject as described below), a "biologically-effective" amount of the virus vector is an amount that is sufficient to result in transduction and expression of the heterologous nucleic acid sequence in a target cell.

The cell to be administered the inventive virus vector may be of any type, including but not limited to neural cells (including cells of the peripheral and central nervous systems, in particular, brain cells), lung cells, retinal cells, epithelial cells (e.g., gut and respiratory epithelial cells), muscle cells, pancreatic cells (including islet cells), hepatic cells, myocardial cells, bone cells (e.g., bone marrow stem cells), hematopoietic stem cells, spleen cells, keratinocytes, fibroblasts, endothelial cells, prostate cells, germ cells, and the like. Alternatively, the cell may be any progenitor cell. As a further alternative, the cell can be a stem cell (e.g., neural stem cell, liver stem cell). Moreover, the cells can be from any species of origin, as indicated above.

In particular embodiments of the invention, cells are removed from a subject, the parvovirus vector is introduced therein, and the cells are then replaced back into the subject. Methods of removing cells from subject for treatment ex vivo, followed by introduction back into the subject are known in the art. Alternatively, the rAAV vector is introduced into cells from another subject, into cultured cells, or into cells from any other suitable source, and the cells are administered to a subject in need thereof.

Suitable cells for ex vivo gene therapy include, but are not limited to, liver cells, neural cells (including cells of the central and peripheral nervous systems, in particular, brain cells), pancreas cells, spleen cells, fibroblasts (e.g., skin fibroblasts), keratinocytes, endothelial cells, epithelial cells, myoblasts, hematopoietic cells, bone marrow stromal cells, progenitor cells, and stem cells.

Dosages of the cells to administer to a subject will vary upon the age, condition and species of the subject, the type of cell, the nucleic acid being expressed by the cell, the mode of administration, and the like. Typically, at least about $10^2$ to about $10^8$, preferably about $10^3$ to about $10^6$ cells, will be administered per dose. Preferably, the cells will be administered in a "therapeutically-effective amount".

A "therapeutically-effective" amount as used herein is an amount of that is sufficient to alleviate (e.g., mitigate, decrease, reduce) at least one of the symptoms associated with a disease state. Alternatively stated, a "therapeutically-effective" amount is an amount that is sufficient to provide some improvement in the condition of the subject.

A further aspect of the invention is a method of treating subjects in vivo with the inventive virus particles. Administration of the parvovirus particles of the present invention to a human subject or an animal in need thereof can be by any means known in the art for administering virus vectors.

Exemplary modes of administration include oral, rectal, transmucosal, topical, transdermal, inhalation, parenteral (e.g., intravenous, subcutaneous, intradermal, intramuscular, and intraarticular) administration, and the like, as well as direct tissue or organ injection, alternatively, intrathecal, direct intramuscular, intraventricular, intravenous, intraperitoneal, intranasal, or intraocular injections. Injectables can be prepared in conventional forms, either as liquid solutions or supenisions, soild forms suitable for solution or suspenions in liquid prior to injection, or as emulsions. Alternatively, one may administer the virus in a local rather than systemic manner, for example in a depot or sustained-release formation.

In particularly preformed embodiments of the invention, the nucleotide sequence of interest is delivered to the liver of the subject. Administration to the liver may be achieved by any method known in art, including, but not limited to intravenous administration, intraportal administration, intrabilary administration, intra-arterial administration, and direct injection into the liver paraenchyma.

Preferably, the cells (e.g., liver cells) are infected by a recombiant parvovirus vector encoding a peptide or protein, the cells express the encoded peptide or protein and secrete it into the circulatory system in a therapeutically-effective amount (as defined above). Alternatively, the vector is delivered to and expressed by another cell or tissue, including but not limited to, brain, pancreas, spleen or muscle.

In other preferred embodiments, the inventive parvovirus particles are administered intramuscularly, more preferably by intramuscular injection or by local administration (as defined above). In other preferred embodiments, the parovirus particles of the present invention are administered to the lungs.

The parovirus vector disclosed herein may be administered to the lungs of a subject by any suitable means, but are preferably administered by adminsitering an aresol suspension of respirable particles comprised of the inventive parovirus vectors, which the subject inhales. The respirable particles may be liquid or solid. Aerosols of liquid particles comprising the inventive parovirus vectors may be produced by any suitable means, such as with a pressure-driven aerosol nebulizer or an ultrasonic nebulizer, as is known to those of skill in art. See, e.g. U.S. Pat. No. 4,501,729. Aerosols of solid particles comprising the inventive virus vectors may likewise be produced with any solid particulate medicament aerosol generator, by techniques known in the pharmaceutical art.

Dosages of the inventive parvovirus particles will depend upon the mode of administration, the disease or condition to be treated, the individual subject's condition, the particular virus vector, and the gene to be delivered and can be determined in a routine manner. Exemplary doses for achieving therapeutic effects are virus titers of at least about $10^5$, $10^6$, $10^7$, $10^8$, $10^9$, $10^{10}$, $10^{11}$, $10^{12}$, $10^{13}$, $10^{14}$, $10^{15}$ transducting units or more, preferably about $10^8$–$10^{13}$ transducting units, yet more preferably $10^{12}$ transducing units.

In particular embodiments of the invention, more than one administration (e.g., two, three, four, or more administrations) may be employed to achieve therapeutic levels of gene expression. According to this embodiment and as described above, it is preferred to use parvovirus vectors having different entigenic properties for each administration to obviate the effects of neutralizing antibodies. As described above, in particular embodiments of the invention, the hybrid and chimeric parvoviruses of the present invention are administered to circumvent neutralizing antibodies in the subject to be treated or to prevent the development of an immune response in the subject. The subject may be presented with seemingly new virus vectors by packaging the rAAV genome within an array of hybrid or chimeric parvovirus capsids.

The foregoing discussion also pertains to pharmaceutical formulations containing parvovirus capsids and other reagents of the invention as well as methods of administering the same.

In summary, the parvovirus vectors, reagents, and methods of the present invention can be used to direct a nucleic acid to either dividing or non-dividing cells, and to stably express the heterologous nucleic acid therein. Using this vector system, it is now possible to introduce into cells, in vitro or in vivo, genes that encode proteins that affect cell physiology. The vectors of the present invention can thus be useful in gene therapy for disease states or for experimental modification of cell physiology.

Having now described the invention, the same will be illustrated with reference to certain examples, which are included herein for illustration purposes only, and which are not intended to be limiting of the invention.

EXAMPLE 1

AAV Vectors

All production of AAV vectors used in these investigations utilized the vector production scheme as described in Ferrari et al., (1997) *Nature Med.* 3:1295 and Xiao et al., (1998) *J. Virology* 72:2224. Utilizing a transient transfection procedure, rAAV devoid of adenovirus has been generated. Id. This protocol utilizes an adenovirus DNA genome that has been incapacitated for viral replication and late gene expression. The mini Ad plasmid while unable to replicate and produce progeny, is still viable for adenovirus gene expression in 293 cells. Using this construct, the AAV packaging strategy involving new AAV helper plasmid (pAAV/Ad ACG) and AAV vector DNA (sub 201) has been successfully complemented (Samulski et al., (1989) *J of Virology* 63:3822). This new construct typically generates rAAV of $10^7$–$10^9$/10 cm dish of 293 cells (Xiao et al., (1998) *J. Virology*, 72:2224). Efficient gene delivery is observed in muscle, brain and liver with these vectors in the complete absence of Ad.

EXAMPLE 2

Cells and Viruses

Human 293 and HeLa cells were maintained at 37° C. with 5% $CO_2$ saturation in 10% fetal bovine serum (Hyclone) in Dulbecco's modified Eagles medium (Gibco BRL), with streptomycin and penicillin (Lineberger Comprehensive Cancer Center, Chapel Hill, N.C.) Four×$10^6$ 293 cells were plated the day before transfection onto a 10 cm plate. Cells were transfected by both calcium phosphate (Gibco BRL) or Superfection (Qiagene) according to manufacturers specifications. The insertional mutant packaging plasmids, described below, were transfected along with pAB11 containing the CMV driven Lac Z gene with a nuclear localization signal. For each transfection the same amount of packaging plasmid (12 µg) and pAB11 (8 µg) were used for each 10 cm plate. For each transfection an additional plate was used containing the transgene plasmid only to assess transformation efficiencies. After transfection the cells were infected with helper virus Ad5 dl309 at an MOI of 5, and 48 hours later the cells were lysed and the virus purified.

Recombinant virus was purified using cesium chloride isopycnic or iodixanol gradients. In both cases cells were centrifuged at 1500 rpms (Sorvall RT 6000B) for ten minutes at 4° C. Proteins were precipitated from the supernatant using ammonium sulfate (30% w/v) and resuspended in 1× Phosphate-buffered saline (PBS) (137 mM NaCl, 2.7 mM KCl, 4.3 mM $Na_2HPO_4 7H_2O$, 1.4 mM $KH_2PO_4$). The cell pellet was resuspended in 1×PBS containing 0.1 mg/ml DNase I (Boehringer Mannheim) lysed by three freeze-thaw cycles, combined with the protein portion of the supernatant, and incubated at 37° C. for 30 minutes. This material was subjected to sonication (Branson Sonifer 250, VWR Scientific), 25 bursts at 50% duty, output control 2. Cell debris was removed by centrifugation (Sorvall RT 6000B). To each milliliter of supernatant 0.6 g of cesium chloride (CsCl) was added and the solution was centrifuged for 12–18 hours (Beckman Optima TLX ultracentrifuge) in a TLS 55 rotor at 55,000 rpms. Alternatively, the supernatant was layered on top of an Iodixanol (OptiPrep—Nycomed Pharma As, Oslo, Norway) gradient of 60%, 45%, 30% and 15%. This gradient was centrifuged in a Beckman Optima TLX ultracentrifuge using a TLN 100 rotor at 100,000 rpm for one hour. Fractions were recovered from these gradients and 10 µl from each fraction were utilized for dot blot hybridization to determine which fraction contained the peack protected viron (see Example 5).

EXAMPLE 3

Construction of AAV Packaging Plasmids

The capsid domain of pAAV/Ad was cloned into pBS+ (Stratagene) using Hind III, resulting in pAV2Cap. Partial digestion of pAV2Cap using the restriction enzymes Hae III, Nla IV, and Rsa I and gel purification of the unit length DNA fragment resulted in the isolation of the starting material for cloning. The aminoglycoside 3'-phosphotranferase gene, conferring kanamycin resistance ($kan^r$), from pUC4K (Pharmacia) digested with Sal I was flanked by linkers containing Nae I and Eco RV sites, a Sal I overhang at one end and an Eco RI overhang at the other end (top 5'-AATTCGCCG-GCGATATC-3', SEQ ID NO:6, bottom 5'-TC-GAGATATCGCCGGC-3'SEQ ID NO:7). This fragment was cloned into the Eco RI site of pBluescript SK+ (Stratagene). Digestion with Nae I released the $kan^r$ gene, and this fragment was ligated into the pAV2Cap partials. The resulting plasmids were screened for insertion into the capsid domain and, then digested with Eco RV to remove the $kan^r$ gene leaving the twelve base pair insertion 5'-GGC-GATATCGCC-3'(SEQ ID NO: 8) within the capsid domain. Multiple enzyme digests and DNA sequencing were used to determine the position of the 12 bp insertion within the capsid coding domain. The enzyme digests include Eco RV/Ban II, Eco RV/Bst NI, Eco RV/Pst II and Eco RV/Hind III. The capsid domain of the resulting plasmids were digested with Asp718 and subcloned into the pACG2 packaging plasmid (Li et al., 1997 *J. Virology* 71:5236), with the exception of one NlaIV clone that overlapped the 3'-Asp718 site. This insertion mutant was cloned into pAAV/Ad using a Hind III/Nsi I digestion.

EXAMPLE 4

Western Blotting

Cell lysates after freeze thaw lysis and sonication was centrifuged to remove large cell debris. Twenty microliters of supernatant was immediately added to 20 µl of 2×SDS gel-loading buffer containing dithiothreitol and boiled for five minutes. Proteins were analyzed by SDS polyacrylamide gel electrophoresis and transferred to nitrocellulose electrophoretically. The nitrocellulose membranes were immunoblotted using the anti-Vp3 monoclonal antibody B1 (a generous gift from Jurgen A. Kleinschmidt). Each of the insertion mutants was tested at least twice by Western blot analysis. The secondary anti-mouse Horseradish Peroxidase IgG was used to indirectly visualize the protein by enhanced chemiluminescence (ECL-Amersham). The Western blots were scanning from enhanced chemiluminescence exposed BioMax film (Kodak) into Adobe PhotoShop and analyzed by ImageQuaNT software (Molecular Dynamics Inc.).

Viral proteins were visualized by Western blotting followed by immunoblotting as described above. Between $1.0 \times 10^9$ and $2.5 \times 10^9$ viral particles were used for each sample. The virus was isolated from the peak cesium gradient fraction as determined by dot blot, and dialysed against 0.5× PBS containing 0.5 mM $MgCl_2$ prior to polyacrylamide gel electrophoresis.

EXAMPLE 5

Titration of Recombinant Virus

Fractions from CsCl gradients were obtained by needle aspiration. The refractive index was obtained using a refractometer (Leica Mark II), and the index was used to determine the density of fractions. Aliquots of 10 µl from fractions between 1.36 g/ml and 1.45 g/ml were tested for the presence of protected particles by dot blot hybridization. The aliquots were diluted 1:40 in viral dilution buffer (50 mM Tris HCl, 1 mM $MgCl_2$, 1 mM $CaCl_2$ 10 µg/ml RNase, 10 µg/ml DNase) and incubated at 37° C. for 30 minutes. To the samples Sarcosine (final concentration 0.5%) and EDTA (final 10 mM) were added and incubated at 70° C. for 10 minutes. Proteinase K (Boehringer Mannheim) was added to a final concentration of 1 mg/ml and the samples were incubated at 37° C. for two hours. Following this incubation the samples were denatured in NaOH (350 mM final) and EDTA (25 mM final). The samples were applied to equilibrated nytran (Gene Screen Plus, NEN Life Science Products) using a dot blot manifold (Minifold I, Schleicher and Schuell). The membrane was probed with a random primed (Boehringer Mannheim) $^{32}$P-dCTP labeled Lac Z DNA fragment. The membranes were exposed to film (BioMax MR, Kodak) or to phosphor imagining screens (Molecular Dynamics) and intensity estimates were done using ImageQuant software (Molecular Dynamics). Peak fraction of virus were then dialysed in 1×PBS for transducing filter.

Transductions titers were determined by histochemical staining for Lac Z activity. HeLa cells had been infected with Ad dl309 at a multiplicity of infection of five for one hour. The cells were then washed with 1×PBS and fresh medium was added. Aliquots of virus from peak fractions, equivalent to $1.75 \times 10^8$ particles were used to infect Hela cells. Twenty to twenty-four hours later cells were washed with 1×PBS, fixed (2% formaldehyde 0.2% gluteraldehyde in 1×PBS), washed, and stained with 5'-Bromo-4-chloro-3-indoly-β-D-galactophyranoside (Gold Bio Technology) dissolved in N,N-dimethylformamide (Sigma) diluted to 1 mg/ml in 1×PBS pH7.8, 5 mM potassium ferricyanide, 5 mM potassium ferrocyanide, 2 mM $MgCl_2$ at 37° C. for 12–24 hours. Stained HeLa cells were counted in ten 400× microscope fields. The transducing number was determined by averaging the number of stained cells in ten fields and multiplying by the number of fields on the plate and dividing that number by the number of nanograms of protected template.

EXAMPLE 6

Electron Microscopy

Peak fractions of rAAV with wildtype viron or mutagenized virions were dialysed in 0.5×PBS containing 0.5 mM $MgCl_2$. The virus was placed on a 400 mesh glow discharged carbon grid by inverting on a 10 µl drop of virus for ten minutes at room temperature. Followed by three 1×PBS washes for one minute each. The virus was stained in 1% Phosphotungstic acid for one minute. Specimens were visualized using a Zeiss EM 910 electron microscope.

EXAMPLE 7

Heparin Agarose Binding Assay

Recombinant virus containing wild-type capsids or insertion in the capsids were dialysed against 0.5×PBS containing 0.5 mM $MgCl_2$. One hundred microliters of each virus was bound to 100 µl of heparin agarose type 1 (H-6508 Sigma, preequilibrated in twenty volumes of 0.5×PBS containing 0.5 mM $MgCl_2$) at room temperature for one hour in a 1.5 ml microfuge tube. After each step, binding washes and elutions samples were centrifuged at 2000 rpm (Sorvall MC 12V) for two minutes to collect supernatant. Samples were washed six times with 0.5 ml of 0.5×PBS containing 0.5 mM $MgCl_2$, and the supernatant collected. Samples were eluted in three steps of 100 µl volumes containing 0.5, 1.0 and 1.5 M NaCl in 0.5×PBS containing 0.5 mM $MgCl_2$ and the supernatant collected. For each sample 20 µl of supernatant from each step was used for dot blot hybridization. The 100% bound control was an internal standard equivalent to one fifth of each input virus used in the dot blot. The heparin agarose viral mixtures were washed six times with 0.5×PBS 0.5 mM $MgCl_2$ in volumes that resulted in a 1:15625 dilution.

EXAMPLE 8

Construction of Insertional Mutations in rAAV2

Figure 1:
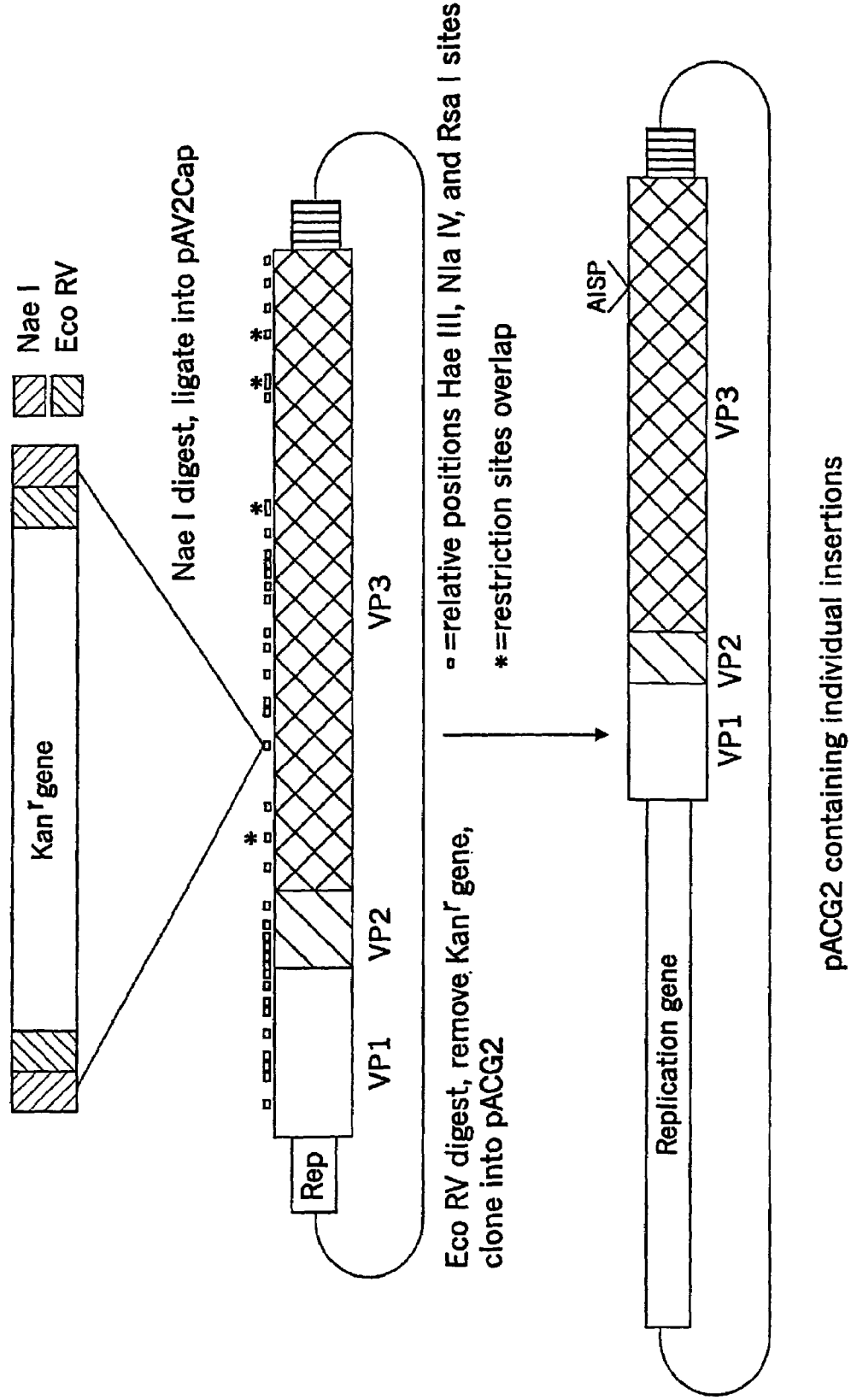

In order to evaluate the role of AAV structural proteins in assembly and infectivity, we generated a collection of capsid linker insertion mutants. A 2.8 kb Hind III fragment of pAAV/Ad (Samulski et al., (1989) *J. Virology* 63:3822) containing the sequences coding for the capsid domain of AAV2 was subcloned into pBS+. This plasmid, pAV2Cap, was used for partial digestion with Hae III, Nla IV, and Rsa I to generate a substrate for capsid specific insertions (FIG. 1). These three DNA restriction enzymes constitute 43 sites that span across the AAV-2 capsid coding sequence of which only 4 overlap. To efficiently identify clones that contain insertions, a kanamycin resistance gene (Kan$^r$) flanked by a novel oligo (Nae I/EcoR V) was ligated with partially digested, full-length, linearized pAV2Cap (see Example 3 and FIG. 1). Using ampicillin and kanamycin selection in *E. coli*, insertion mutants were identified and the Kan$^r$ gene was shuttled out of the capsid coding region by digesting and religation with the nested pair of Eco RV sites (see Example 3). This resulted in a specific linker insertion of 12 base pair (bp) carrying a single copy of the unique Eco RV site in the capsid coding sequences. The exact positions of the linker insertion were further refined by restriction enzyme digestions, and in six cases sequencing (data not shown). The position of insertion mutants are identified by the first letter of the enzyme used in the partial digestion followed by the nucleotide position of the restriction site in the AAV2 genome, for example Nla IV 4160 would be N4160.

The capsid coding sequence from these mapped insertion mutants were subcloned into the helper vectors pACG2 or pAAV/Ad for biological characterization in vivo (FIG. 1) (Li et al., (1997) *J. Virology* 71:5236; Samulski et al., (1989) *J. Virology* 63:3822). Sequence analysis predicts that this 12 base pair insertion cannot result in a termination codon for any of the 43 insertion sites (Table 1). Owing to the random nature of the cut site for the enzymes (Hae III, Nla IV, and Rsa I) with respect to codon frame usage and the degeneracy of the Nla IV recognition sequence, the 12 bp linker resulted in the insertion of the amino acids GDIA in frame 1 and AISP in frame 3 for all three enzymes, while insertions in frame 2 resulted in WRYRH for Rsa I, GRYRP for Hae III, and both GRYRP and GRYRH for Nla IV. The bolded amino acid in these examples represents missense mutation (Table 1). The mutant helper constructs, pACG2$^{IN}$, were individually transfected into 293 cells along with an AAV reporter vector, containing the β-galactosidase gene in Adenovirus dl309 (MOI=5) infected cells (Li et al., (1997) *J. Virology* 71:5236). The transfected cells were then assayed for capsid expression and recombinant virus production (see Example 5; Li et al., (1997) *J. Virology* 71:5236).

TABLE 1

Physical Structure and Phenotype of AAV2 Capsid Insertion Mutants

| Position[1] inserted | Capsid subunit | Frame[2] | Dot blot[3] | Infectious[4] | Heparin Agarose[5] | Electron Microscope | Phenotype | Amino Acid[6] |
|---|---|---|---|---|---|---|---|---|
| H2285 | VP1 | 3 | 2.8 × 10$^7$ | – | + | normal | Class II | AISP |
| R2356 | VP1 | 2 | 1.4 × 10$^8$ | + | + | N.D. | Class III | WRYRH |
| N2364 | VP1 | 1 | — | – | N.D. | N.D. | Class I | GDIA |
| H2416 | VP1 | 2 | 1.4 × 10$^7$ | – | + | N.D. | Class II | GRYRP |
| H2591 | VP1 | 3 | 1.4 × 10$^7$ | + | + | normal | Class III | AISP |
| H2634 | VP2 | 1 | 2.8 × 10$^7$ | – | + | normal | Class II | GDIA |
| H2690 | VP2 | 3 | 7.0 × 10$^6$ | + | + | normal | Class III | AISP |
| R2747 | VP2 | 3 | — | – | N.D. | N.D. | Class I | AISP |
| H/N2944 | VP3 | 2 | 1.4 × 10$^6$ | +* | N.D. | N.D. | Class II/III | GRYRP |
| N3317 | VP3 | 3 | 1.4 × 10$^5$ | – | N.D. | N.D. | Class II | AISP |
| R3391 | VP3 | 2 | — | – | N.D. | N.D. | Class I | WRYRH |
| N3561 | VP3 | 1 | — | – | N.D. | N.D. | Class I | GDIA |
| H3595 | VP3 | 2 | 1.4 × 10$^6$ | +* | N.D. | abnormal | Class II/III | GRYRP |
| H/N3761 | VP3 | 3 | 1.4 × 10$^7$ | – | – | normal | Class II | AISP |
| H3766 | VP3 | 2 | 2.8 × 10$^7$ | – | N.D. | N.D. | Class II | GRYRP |
| N4046 | VP3 | 3 | — | – | N.D. | N.D. | Class I | AISP |
| H/N4047 | VP3 | 1 | — | – | N.D. | N.D. | Class I | GDIA |
| N/R4160 | VP3 | 3 | 1.4 × 10$^7$ | + | + | normal | Class III | AISP |

[1]The letter refers to the restriction enzyme used in the partial digestion and the number refers to nucleotide of the restriction site in the AAV2 sequence.
[2]Reading frame of the restriction site.
[3]The particle number per microliter of sample. (–) = < 10$^5$ genomes.
[4]Infections were done using 1.75 × 10$^8$ particles of rAAV insertion mutants in adenovirus infected HeLa cells.
[5]By batch binding and assayed by infection of HeLa cells (Class III) or by dot blot (Class II).
[6]Amino acids differ depending on the frame of the insertion. The bolded amino acid is a missense mutation.

EXAMPLE 9

Analysis of Capsid Proteins

Figure 2:
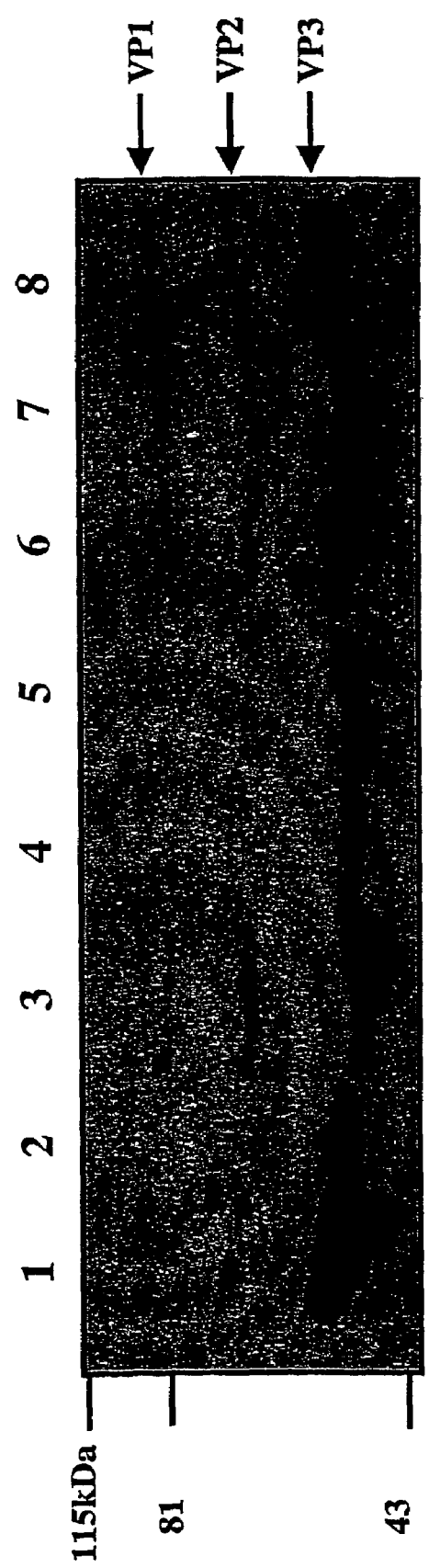

Before assaying for vector production using mutant capsid constructs in complementation assays, each insertion mutant was tested for expression of capsid subunits in 293 cells after transfection. The ability to produce Vp1, Vp2, and Vp3 at normal stoichiometry would suggest that linker insertions did not alter capsid protein expression, or stability. Since the linker did not introduce stop codons, it was expected that each insert would produce all three capsids. Forty-eight hours after transfection, cell lysates were analyzed by Western blot for AAV capsids. The Western blot analysis in FIG. 2 is a representation of insertion mutant capsid expression in cell lysates. With the exception of H2634 (FIG. 2 lane 2), the stoichiometry of the three capsid subunits does not appear significantly different than that of wild-type controls (FIG. 2 compare lanes 1,3–7 to lane 8). By this assay, insertion mutant H2634 appears to only produce Vp3 subunits (FIG. 2; lane 2). In longer exposures, the minor capsid subunits in FIG. 4 lanes 4 and 5 were apparent (data not shown).

EXAMPLE 10

Mutant Capsid Ability to Produce Stable Virions

Figure 3:
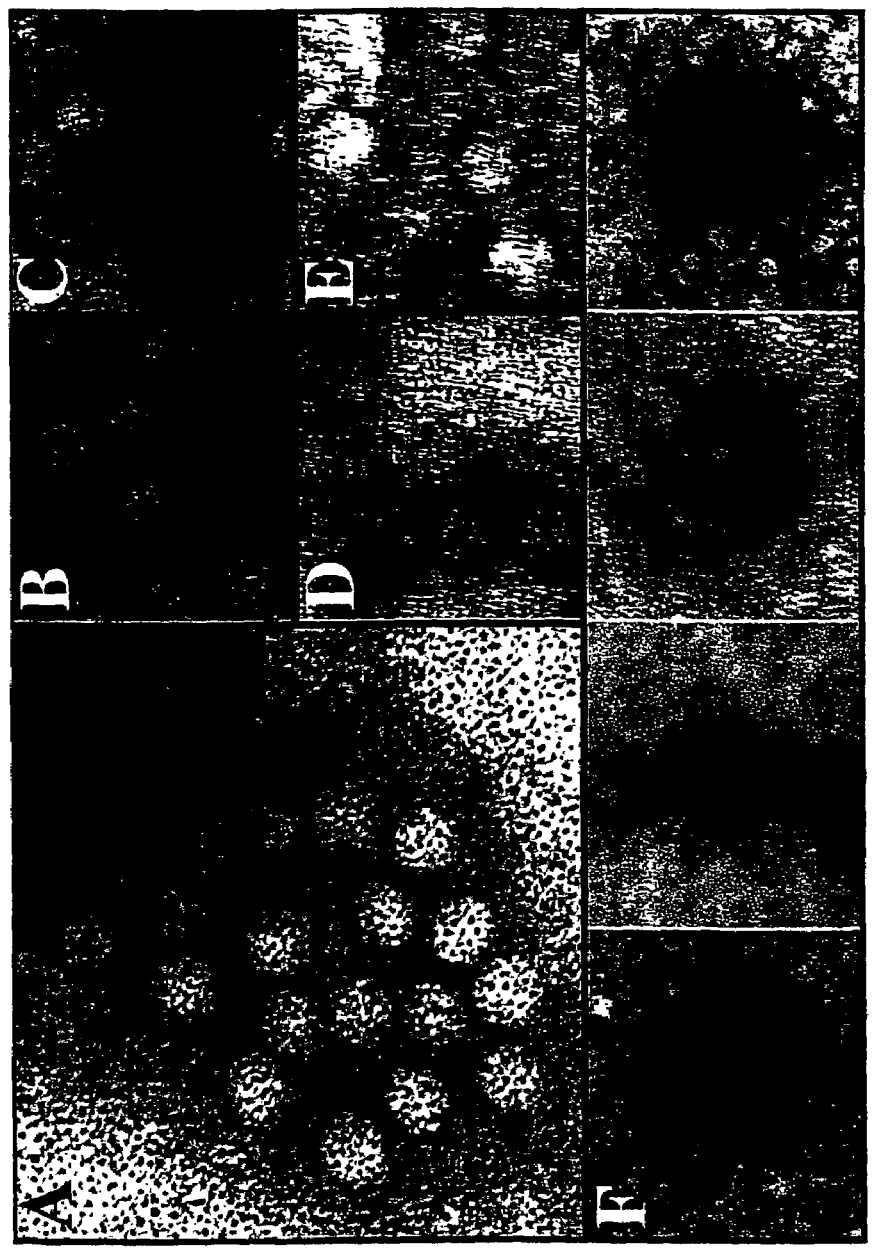

To test for the production of stable virions that protect a vector genome from DNase digestion, we subjected the cell lysates to cesium chloride (CsCl) gradient centrifugation. Virus densities were measured by refractometry, and aliquots from appropriate fractions were subjected to dot blot hybridization (FIG. 3a). Based on this analysis, particles that package intact recombinant genomes should display a buoyant density similar to wild-type and be resistant to DNase treatment, with the exception of H2944 which has a buoyant density slightly higher than wild type. Results for this assay separated insertion mutants into two classes. Class I mutants were negative for protecting the viral genome, while class II mutants appeared normal for packaging and protecting the vector substrate (Table I).

All class II mutants had a buoyant density within the range of wild-type AAV2 capsids (FIG. 3a). By dot blot analysis, N2944 packaged the recombinant genome but migrated to a position of slightly greater density than wild type in isopycnic gradients (FIG. 3a, N2944 lane 3). A number of insertion mutants (7) did not package DNA by this assay which had a sensitivity of <1×10$^5$ particles/µl (see methods for quantitation) (Table 1). Whether these mutants were defective in packaging or unstable during purification remains to be determined.

EXAMPLE 11

Infectivity of Class II Insertion Mutants

Virions generated by insertion mutants in the complementation assay were tested for infectivity by monitoring transduction of LacZ reporter gene in human cells. Using viral titers derived from dot blot hybridization, HeLa cells were infected with mutant virus stocks at equivalent particle numbers.

Twenty-four hour post infection, expression of the transgene was detected by X-gal staining. A representative figure of this analysis is shown (FIG. 3b) and all mutanta assayed are presented in Table 1. In this assay, wild-type virions transduced 5.6×10$^5$ HeLa cells/1.75×10$^8$ protected particles (FIG. 3b). Based on the sensivity of this assay, the range of infection efficiency for class II insertion mutant viruses was from 0 to 1.6×10$^6$ transducing units/1.75×10$^8$ protected particles. Results from this analysis further subdivided the capsid insertion mutants from class II (normal for packaging and protecting the vector substrate) into a class III phenotype (normal for packaging and protecting the vector substrate and infectious virions). Two insertion mutants negative for infectivity and initially identified as class II mutants (N2944, H3595) based on CsCl purification and DNase protection, tested positive for viral transduction after purification using an iodixanol step gradient (Table 1). This virus purification technique is not as harsh as CsCl and has been shown to increase virus recovery by ten-fold (Zolotukhin et al., (1999) *Gene Therapy* 6:973). However, other class II mutants remained non-infectious after purification using an iodixanol step gradient (data not shown). Although we determined that insertion mutant viruses N2944 and H3595 were infectious using the Lac Z transduction assay, it should be noted that these mutants resulted in low infectious titers (1×10$^2$ transducing units/ng) similar to previously published lip mutants (Hermonat et al., (1984) *J. Virology* 51:329).

EXAMPLE 12

Electron Microscopy of Class II and Class III Mutants

Figure 4:
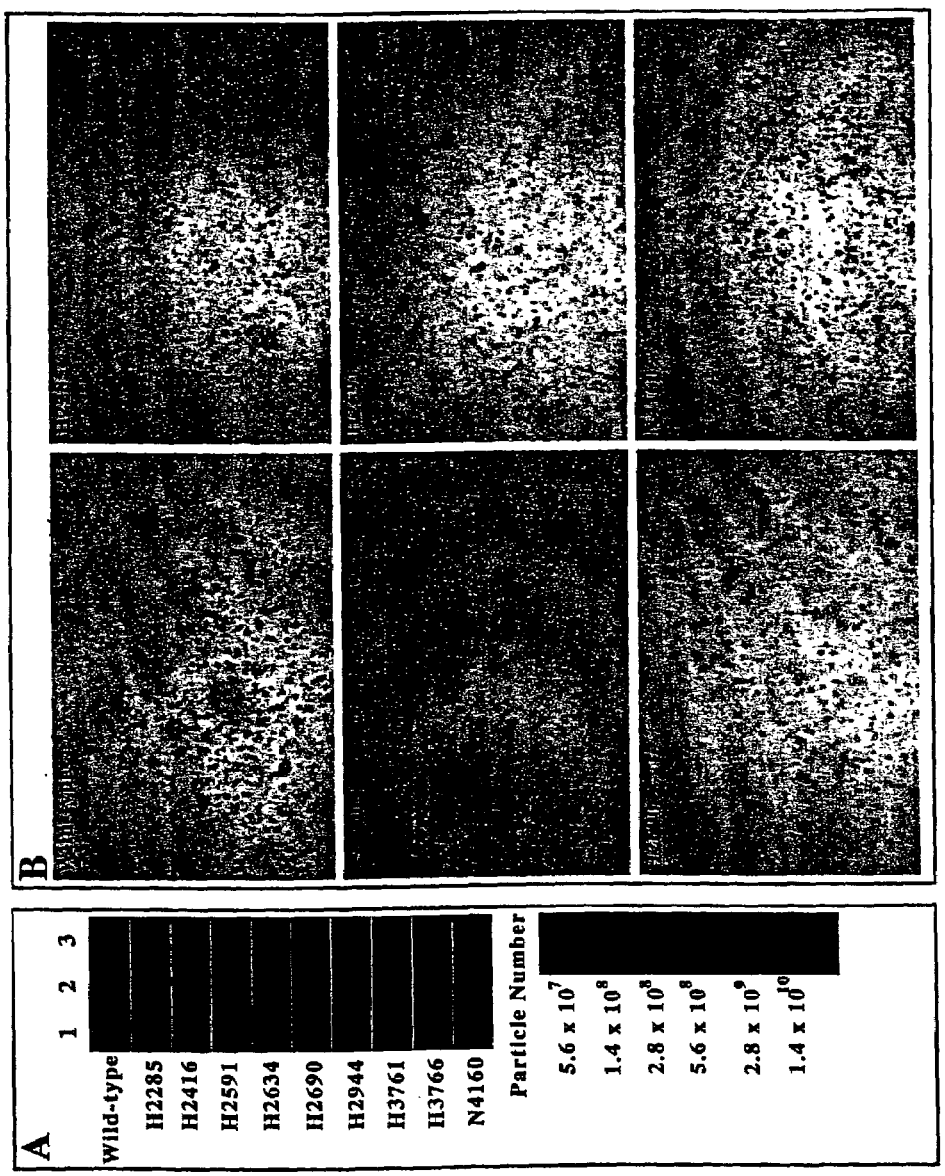

To further characterize class II and III rAAV2 insertion mutants for biological differences, we visualized mutant particles by electron microscopy (EM). The EM analysis revealed only gross morphology of the infectious class III viruses, which were indistinguishable from wild-type virions (Compare FIG. 4a, and 4b,c). Whereas distinct differences were observed between class II/III mutant virus H3595 when compared to wild-type virions (FIG. 4a, and 4f-bottom four panels). EM images of H3595 revealed a slightly larger roughly pentagonal outline, while wild-type virus appeared uniformed in size and was hexagonal. Interestingly, class II mutant H2634, which was negative for Vp1 or Vp2 by Western blot (FIG. 2 lane 2), appeared normal in morphology by EM analysis (FIG. 4d). Based on this analysis, virion morphology alone is not sufficient to distinguish class II mutants from class III since small insertions within the capsids can result in either non-detectable (FIG. 4b,c,d,e) or noticeable alterations in virion structure (FIG. 4f-bottom four panels). However, this approach was able to provide additional data to our characterization of these linker insertion mutants (FIG. 4, compare a to f).

EXAMPLE 13

Capsid Ratio of Class II and Class III Virions

Figure 5:
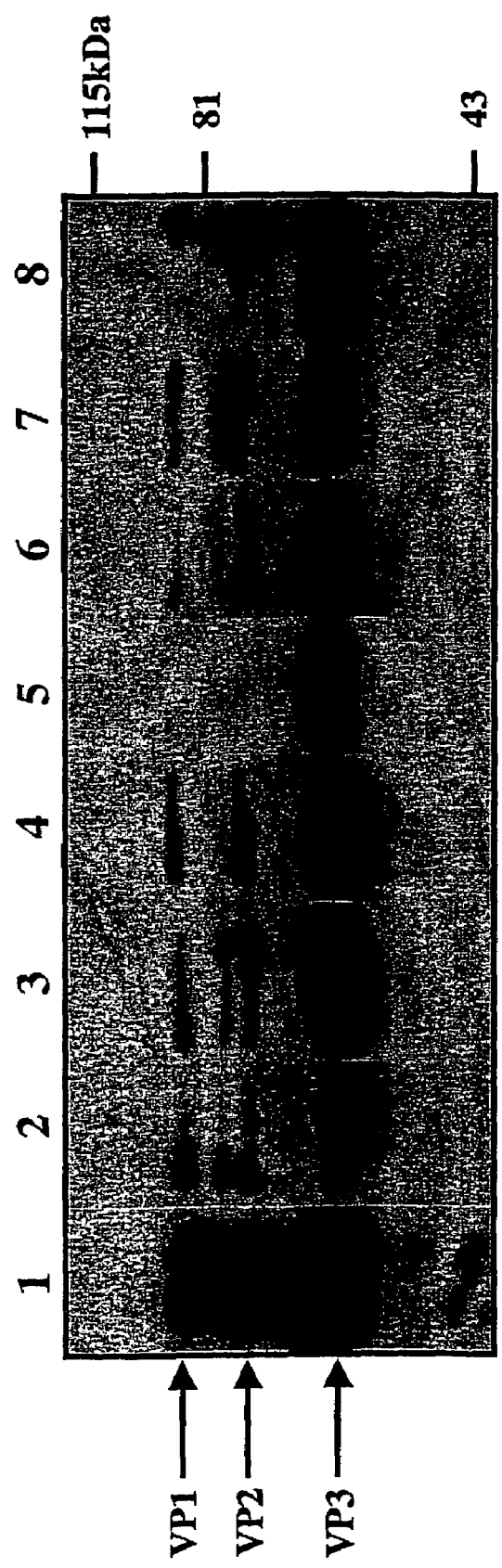

Rose et al., (1971) established that AAV2 particles are composed of Vp1, Vp2, and Vp3 at a 1:1:20 ratio (Rose et al., (1971) *J. Virology* 8:766). In an effort to determine if class II and class III mutant virions maintained this ratio, Western blots were performed on the cesium chloride purified virus. Purified viruses analyzed by Western blot showed similar amounts of Vp3 in all mutants sampled (FIG. 5, Vp3 arrow), between 1×10$^9$ and 2.5×10$^9$ viral particles were used for each sample. The amounts of Vp2 and Vp1 are also nearly equivalent in all test samples except H2634 where no minor capsid components were observed (FIG. 5, lane 5). The lack of minor capsid components for H2634 is consistent with the Western results from cell lysate (FIG. 2). At the limit of detection in this assay, the class II insertion mutant H2634 appears to assemble AAV virions without Vp1 and Vp2, even though EM analysis suggest this mutant has normal morphology (FIG. 4d).

EXAMPLE 14

Heparin Binding of Class II and Class III Mutants

Figure 6:
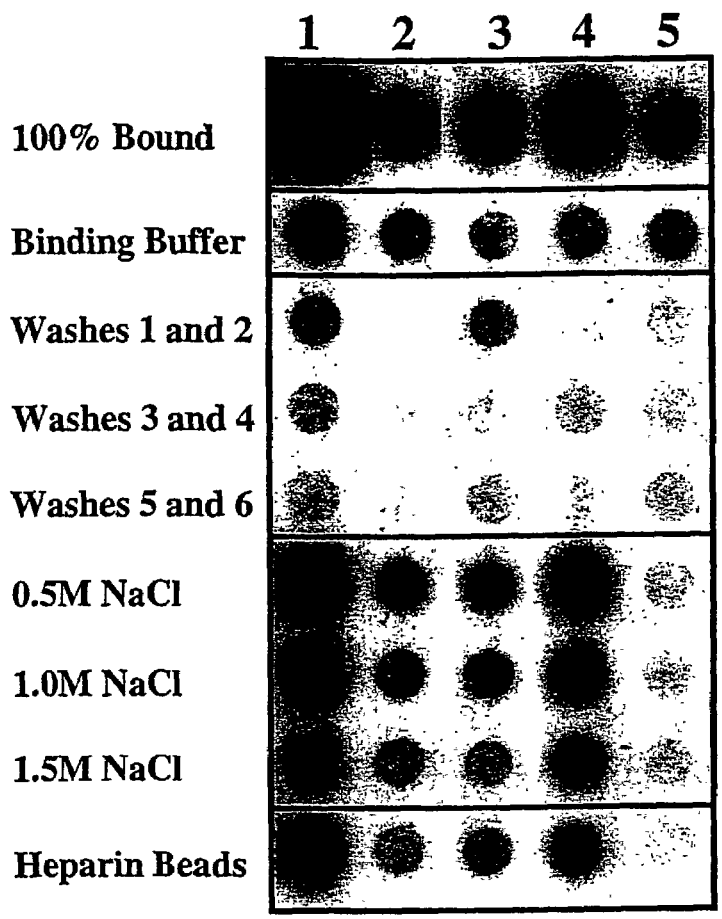

Recently our lab established that AAV-2 uses a heparan sulfate proteoglycan as a primary receptor for infectivity (Summerford and Samulski, (1998) *J. Virology* 72:1438). To determine what role heparin binding may have in class II particles inability to infect cells as well as the ability of class III virus to bind heparin agarose, heparin batch binding experiments were performed. Not surprisingly, all class III mutants were positive for heparin binding, with the majority of virus eluting in the 1M NaCl$_2$ step (data not shown). To determine if loss of infectivity of class II mutant viruses was related to a lack of heparin binding, batch binding experiments were analyzed by dot blot hybridization (FIG. 6). For each of the viral samples tested, an internal control to determine 100% bound was spotted on the filter independent of heparin binding (FIG. 6; 100% bound). This allowed us to determine percent virus retained, at each step of heparin purification. After binding to heparin agarose, samples were washed then eluted using increasing salt concentrations (see Example 7). Recombinant AAV2 with wild-type virion shells demonstrated 90% binding with 10% released in the wash followed by 60% recovered in the elution buffer, and 20% remaining bound to heparin agarose (FIG. 6, lane 1). Class II mutants H2285, H2416, and H2634 demonstrated similar binding and elution profiles (FIG. 6, lanes 2–4). However, class II mutant H3761 was distinct in its heparin agarose binding profile with the majority of the virion in the binding buffer and the washes (FIG. 6, lane 5). Further analysis is required to determine the reason for lack of Heparin binding in this batch assay.

Interestingly, H2634 binds heparin agarose under these conditions, which by Western blot does not carry detectable Vp1 or Vp2 subunits (FIG. 5, lane 4). The lack of Vp1 and Vp2 in H2634 along with its ability to bind heparin agarose suggest that the heparin binding domain may be located in Vp3 capsid proteins.

EXAMPLE 15

Linker Insertion Mutants

Insertion sequences encoding poly-lysine, poly-histidine, an RGD motif, or bradykinin were inserted into the linker mutants described in Table 1. We developed a PCR-based method of identifying insertions of different linkers into the coding domain of AAV2 capsid gene. Briefly, one primer was used outside of the capsid coding region and one that corresponds exactly to the linker. If the linker is in the correct orientation, then the PCR product is of a size that is dependent on the insertion mutant's position.

After transformation of the ligation reactions, bacterial colonies were picked with a pipet tip and dipped 4–5 times into a well of a 96-well plate containing LB-medium with antibiotic. The pipet tip was then placed in a well of a 96-well plate containing PCR reaction buffer. The PCR products were run out on an agarose gel, and positive clones were identified. This information indicated the orientation and the position of the insertion mutant with respect to the outside primer.

The LB-medium that is in the corresponding well was used as the PCR positives, and this material was grown in a larger (5 mL) volume. After an overnight growth phase, the plasmid DNA was islolated and digested with an enzyme that restricts the DNA 15 times (Bst NI). These digestion products were separated on a 5–6% acrylamide gel. Depending upon the size of the linker insertion and the size of the corresponding uninserted fragment, the number of inserts is determined. This, within two days of ligating the linker into the insertion site, we know the orientation and number of linker insertion, and we have sufficient DNA to transfect a 10 cm plate for virus production.

pACG2 (Li et al., 1997 *J. Virology* 71:5236) without any insertion when digested with Bst N1 yields fragments of:

3900 bp
1121 bp
1112 bp
445 bp-H2944 shifts
347 bp-H2634, H2690 shifts
253 bp-H3595 shifts
215 bp-R2356, H2416 shifts
121 bp
111 bp
64 bp
63 bp-H2285 shifts
33 bp-H2591 shifts
13 bp
9 bp The band shifts with the different insertion mutants are also indicated.

pACG2 without any insertion when digested with Ban I yields fragments of:

2009 bp
1421 bp
168 bp
843 bp-H4047 shifts
835 bp
734 bp-H2634 shifts
464 bp
223 bp
218 bp
211 bp
50 bp Each of the inserts contains the original 12 base pairs of the Eco RV site. In addition, each of the linkers adds additional base pairs:

RGD=36 bp+12=48 bp for a single insertion.

Bradykinin (BRDY)=69 bp+12=81 bp for a single insertion.
Note: The BRDY insert contains a BstNI site.

Histidine (8HIS)=51 bp+12=63 bp for a single insertion.

Poly Lysine (PLY)=63 bp+12=75 bp for a single insertion.

The outside primer is near the Hind III site and is called AAV2/4 5'. This primer can be used to amplify AAV serotypes 2 and 4.

Primer sequences used to produce epitope linkers into the original insertion mutants are given below. Note: Because there are three frames for the insertion mutants there are three primer pairs for each primer set.

Histidine primer pairs:

```
Frame 1:
Top primer a 48mer:
5'-GCT AGC GGC GGA CAC CAT CAC CAC      (SEQ ID NO:9)
CAC CAT CAC CAC GGC GGA AGC GCT-3'

Bottom primer a 48mer:
5'-AGC GCT TCC GCC GTG GTG ATG GTG     (SEQ ID NO:10)
GTG GTG ATG GTG TCC GCC GCT AGC-3'

Frame 2:
Top primer a 51mer:
5'-AC GCT AGC GGC GGA CAC CAT CAC      (SEQ ID NO:11)
CAC CAC CAT CAC CAC GGC GGA AGC
                           GCT T-3'

Bottom primer a 51mer:
5'-A AGC GCT TCC GCC GTG GTG ATG (SEQ ID NO:12)
  GTG GTG GTG ATG GTG TCC GCC GCT
                          AGC GT-3'

Frame 3:
                Top primer a 51mer:
5'-G GGT TCC GGA GGG CAC CAC CAT (SEQ ID NO:13)
  CAC CAC CAC CAT CAC GGA GGC GCC
                          AGC GA-3'

Bottom primer a 51mer:
5'-TC GCT GGC GCC TCC GTG ATG GTG (SEQ ID NO:14)
  GTG GTG ATG GTG GTG CCC TCC GGA
                           ACC C-3'

Bradykinin primer pairs:
                           Frame 1:
                Top primer a 60mer:
5'-GCC GGA TCC GGC GGC GGC TCC AGA (SEQ ID NO:15)
   CCC CCC GGC TTC AGC CCC TTC AGA
                   TCC GGC GGC GCC-3'
```

-continued

```
        Bottom primer a 60mer:
5'-GGC GCC GCC GGA TCT GAA GGG GCT    (SEQ ID NO:16)
   GAA GCC GGG GGG TCT GGA GCC GCC
              GCC GGA TCC GGC-3'

Frame 2:
         Top primer a 69mer:
5'-GA GGT TCA TGT GAC TGC GGG GGA     (SEQ ID NO:17)
   AGA CCC CCT GGC TTC AGC CCA TTC
   AGA GGT GGC TGC TTC TGT GGC G-3'

Bottom primer a 69mer:
5'-C GCC ACA GAA GCA GCC ACC TCT      (SEQ ID NO:18)
   GAA TGG GCT GAA GCC AGG GGG TCT
   TCC CCC GCA GTC ACA TGA ACC TC-3'

Frame 3:
         Top primer a 60mer:
5'-A GGT TCA TGT GAC TGC GGG GGA      (SEQ ID NO:19)
   AGA CCC CCT GGC TTC AGC CCA TTC
   AGA GGT GGC TGC TTC TGT GGC GG-3'

Bottom primer a 60mer:
5'-CC GCC AGA GAA GCA GCC ACC TCT     (SEQ ID NO:20)
   GAA TGG GCT GAA GCC AGG GGG TCT
   TCC CCC GCA GTC ACA TGA ACC T-3'

RGD primer pairs:
                  Frame 1:
          Top primer a 36mer:
5'-GGA TCC TGC GAC TGC AGG GGC GAT    (SEQ ID NO:21)
              TGT TTC TGC GGC-3'

Bottom primer a 36mer:
5'-GCC GCA GAA ACA ATC GCC CCT GCA    (SEQ ID NO:22)
              GTC GCA GGA TCC-3'

Frame 2:
          Top primer a 36mer:
5'-GA TCC TCG GAC TGC AGG GGC GAT     (SEQ ID NO:23)
              TGT TTC TGC GGC G-3'

Bottom primer a 36mer:
5'-C GCC GCA GAA ACA ATC GCC CCT      (SEQ ID NO:24)
              GCA GTC GCA GGA TC-3'

Frame 3:
          Top primer a 36mer:
5'-A GGA TCC TGC GAC TGC AGG GGC      (SEQ ID NO:25)
              GAT TGT TTC TGC GG-3'

Bottom primer a 36mer:
5'-CC GCA GAA ACA ATC GCC CCT GCA     (SEQ ID NO:26)
              GTC GCA GGA TCC T-3'

Polylysine primer pair:
Note: only the frame three primer pair was made.
Frame 3:
Top primer a 63mer:
5'-A GGT TCA TGT GAC TGC GGG GGA      (SEQ ID NO:27)
   AAG AAG AAG AAG AAG AAG AAG GGC
              GGC TGC TTC TGT GGC GG-3'

Bottom primer a 63mer:
5'-CC GCC ACA GAA GCA GCC GCC CTT     (SEQ ID NO:28)
   CTT CTT CTT CTT CTT TCC CCC
              GCA GTC ACA TGA ACC T-3'

Outside primer AAV 2/4 5' top primer:
5'-TGC CGA GCC ATC GAC GTC AGA        (SEQ ID NO:29)
                   CGC G-3'
```

The RGD linker was inserted into the H2285, R2356, H2591, H2634, H2690, H/N3761, and H/N4047 mutants from Table 1.

The bradykinin linker was inserted into the H2285, H2416, H2591, H2634, H2690, H/N2944, and H/N3761 mutants from Table 1.

The poly-Lys linker was inserted into the H2285, H2591, H2690, and H/N3761 mutants from Table 1.

The poly-His linker was inserted into the H2285, H2416, H2591, H2634, H2690, H/N2944, H3561, H3766, and H/N4047 mutants from Table 1.

EXAMPLE 16

Characterization of Insertion Mutants

The insertion mutants at site H2690 all have titers similar to the original 12 bp insert. Using the ELISA assay and the anti-histidine antibody polyHis insertions into this site were shown to be displayed on the surface of the virion.

The polyHis epitope was also shown to be on the surface when inserted into site H2634. Interestingly, the Western blot analysis of the 12 bp insertion at H2634 did not show any VP1 or VP2 subunits being formed. It has been determined that this insertion in VP2 is near the nuclear localization signal for the VP1 And VP2 subunits. It is possible that this domain was disrupted by the original insertion, and with the addition of the 8-histidines the domain was repaired. Although the dot blot of this 8His virus showed the presence of viral particles, these particles were not infectious.

The insertion site H2591 is in VP1. Insertion of linker epitopes into this site do not affect the titer any more than did the original 12 bp insertion at this site (Table 1).

The insertion at site N4160 is in VP3 near the carboxy terminus. This insertion mutant is of interest because the original 12 bp insertion infects cell at an equivalent level as wild-type (Table 1).

Mutant R3317, which as been previously described in Table 1, appeared not to protect virions by dot blot analysis. Repeating this experiment with a LacZ transgene, the same results were observed, i.e., no protected particles. However, when using an independent clone and the GFP transgene (~1000 bp smaller than LacZ) protected particles were observed. In addition, the GFP-expression virion transduced HeLa cells at high levels, equivalent to wild-type. It is unclear why disparate results were observed with different transgenes.

In addition, a linker encoding the respiratory syncitial virus heparin binding domain is inserted into the H2690 mutant at a site that tolerates inserts without loss of viability (Table 1) to restore heparin binding to this mutant.

EXAMPLE 17

Unique Restriction Site Mutants

Unique restriction sites within the capsid of AAV type 2 were made to facilitate the generation of insertional mutants. The sites were chosen so that the mutations introduced into the nucleotide sequence of the capsid were conservative, i.e., were not missense mutations or result in stop codons. Amino acid positions 586, 529, 595, 552, and 517 (VP1 methionine as amino acid #1) were chosen. For all of these positions, except 529, unique Hpa I sites were engineered. For the site at amino acid 529, a unique Eco RV site was engineered. Each of these unique restriction sites results in an in-frame blunt ended digestion product. So frame 1 linkers were used to insert into these sites. Overlapping primers were used to generate the unique sites, and outside primers were used to generate the right and left fragments of the insertion.

The right fragment was then digested with Nsi I and either Eco RV or Hpa I, and the left fragment with Hind III and either Eco RV or Hpa I. We cloned these digestion products into the pACG vector that had already digested with Hind III and Nsi I. The resulting plasmid was then digested with Xcm I and Bsi WI. These enzymes result in an ~750 bp fragment around the engineered unique restriction site. This strategy will result in the accumulation of fewer errors because the PCR generated sequences are smaller.

The primers:

```
595 top primer
5'-GCA GAT GTT AAC ACA CAA GGC GTT    (SEQ ID NO:30)
                           CTT CCA-3':

595 bottom primer
5'-TTG TGT GTT AAC ATC TGC GGT AGC     (SEQ ID NO:31)
                           TGC TTG-3':

586 top primer
5'-CAG AGA GTT AAC AGA CAA GCA GCT     (SEQ ID NO:32)
                           ACC GC-3':

586 bottom primer
5'-GTC TGT TAA CTC TCT GGA GGT TGG     (SEQ ID NO:33)
                           TAG ATA-3':

Note: This construct results in a missense
mutation Glycine to Valine
552 top primer
5'-ACA AAT GTT AAC ATT GAA AAG GTC     (SEQ ID NO:34)
                           ATG ATT-3':

552 bottom primer
5'-TTC AAT GTT AAC ATT TGT TTT CTC     (SEQ ID NO:35)
                           TGA GCC-3':

529 top primer
5'-GGA CGA TAT CGA AAA GTT TTT TCC     (SEQ ID NO:36)
                           TCA G-3':

529 bottom primer
5'-ACT TTT CGA TAT CGT CCT TGT GGC     (SEQ ID NO:37)
                           TTG C-3':

Note: This construct results in a missense
mutation Glutamic acid to Isoleucine
517 top primer
5'-TCT CTG GTT AAC CCG GGC CCG GGC     (SEQ ID NO:38)
                           ATG GCA-3':

517 bottom primer
5'-GGC CGG GTT AAC CAG AGA GTC TCT     (SEQ ID NO:39)
                           GCC ATT-3':

The outside primers were:
                    5'primer
    5'-TGC GCA GCC ATC GAC GTC AGA     (SEQ ID NO:40)
                           CGC G-3':

3'primer
    5'-CAT GAT GCA TCA AAG TTC AAC TGA (SEQ ID NO:41)
                           AAC GAA T-3':
```

Four clones were also generated with the RGD and 8His linkers (Example 15) inserted into the 529 Eco RV site. Five 8His linkers and one RGD linker insertion mutants were generated into the 586 Hpa I site.

The unique restriction site messense mutations at 3790–3792 (amino acid 529; EcoRV) did infect HeLa cells, although at relatively low efficiency (~1/100 to ~1/1000 of wild-type). When the 8His epitome insert was inserted at this site, the resulting virus had a lip phenotype (i.e., a low infectious particle).

Insertions into the unique missense restriction site at 3690–3961 (amino acid 586; Hpa I) both 8His and RGD were both very infectious, transducing HeLa cells at least as well as wild-type virus.

EXAMPLE 18

Double Mutants

Double mutants were generated using the single mutant H3761 (Table 1) as a template. The H3761 insertion mutant does not bind heparin sulfate as assessed by both batch and column binding experiments. This mutant is interesting because it does not infect any of the cell lines so far tested, although electron microscopy analysis suggests that this virus forms normal parvovirus shells, and by dot blot hybridization this virus packages the viral genome efficiently.

The region of the capsid coding the sequence that contains the H3761 insertion was subcloned into other insertion mutants to create double-mutants. The H2690 (AA# 163) insertion mutant was chosen because it has been shown to display a poly-His insertion epitopes on the viral surface (as assessed by using the conformational specific antibody to bind the virus to an ELISA plate and an anti-histidine antibody preconjugated to horse radish peroxidase to detect the virus containing histidines).

the H2690 insertion mutant helper plasmid (pACG H2690 BRDY) containing the bradykinin insertion (Example 15) and the pACG H3761 insertion mutant were both digested with Hind III and Bsi WI. The Hind III site is in the rep gene, while the Bsi WI site is between 2690 and 3761. The small fragment contains pACG H2690 BRDY while the large fragment contains pACG H3761.

A double mutant H2690 BRDY H3761, with the bradykinin insert inserted at the H2690 site, demonstrated a five-fold increase in infectivity of A9 cells expressing the bradykinin receptor as compared with the parental A9 cells alone. These results indicate (1) the defect in binding of the H3761 is likely at the point of binding to cellular HS receptors, but this virus retains infectivity if directed into cells by another route, and (2) the bradykinin double-mutant targeted entry of the virus into bradykinin-receptor expressing cells.

The H3761 insertion mutant has also been cloned into the unique restriction site missense mutations (Example 17), AA# 586 (Hpa I) and AA# 529 (EcoRV). The restriction enzyme NcoI lies between the H3761 and the 529 (Glu→Ile) and 586 (Gly→Val) missense mutations, and this enzyme cuts within the rep gene. By digesting the pACG2 helper plasmid contain the H3761 and the 586 and 529 unique sites with Nco I, the small Nco I fragment (3142 bps) containing the H3761 insertion mutation and the large Nco I fragment (5034 bps) containing the 586 and 529 unique sites were isolated. After ligation, the constructs with the correct orientation were established, and these clones were used to make virus.

the unique restriction site missense mutations that containing the RGD motif (Example 15) were also used in this cloning strategy. Thus, there are double mutants containing no inserts at the unique sites and double mutants containing RGD epitopes at those sites.

The H3761 mutant does not transduce HeLa or CHO-K1 cells. In contrast, the 586-RGD double mutants exhibited transduction of both of these cell types. These results strongly suggest that the transduction was mediated by the RGD motif introduced into the 586 unique restriction site.

The double mutants with the unique restriction sites, but no inserts, and the 529-RGD double mutant did not exhibit efficient transduction of HeLa or CHO-K1 cells.

EXAMPLE 19

MSH-Targeted AAV Vector

In one embodiment of the invention, melanocyte stimulating hormone (MSH) is used for targeting of AAV vectors to cells expressing MSH receptors. Studies have shown that this peptide will direct ligand-associated complexes specifically into melanocyte NEL-M1 cells (Murphy et al., (1986) *Proc. Nat. Acad. Sci USA* 83:8258), providing a convenient test system. For example, diphtheria toxin tethered to a 12-residue peptide encoding the MSH ligand was efficient in killing only MSH receptor expressing cells (Morandini et al., (1994) *Internat. J. Ca*. 56: 129) Cell death was attributed to receptor mediated endocylosis of the specific ligand delivery.

MSH is inserted into loop 3 of the AAV type 2 capsid. In the first step, an AAV type 2 deletion mutant is made with a 12-amino acid deletion when the Bgl II—SpH I fragment is removed from the sequence encoding loop 3. The sequence encoding the MSH peptide is then inserted into the deleted region.

The primer sequences to make the loop3 and loop4 insertion mutations are as follows:

Loop 3 5' top primer (SEQ ID NO:42):

5-'GATACCTTAAGATCTAGTGGAACCAC-CACGCACTCAAGGCTT-3'

The cttaag is an Afl II site, the agatct is a Bgl II site. These two sites overlap by two base pairs. The homology with the AAV sequence starts at position 3556 and ends at 3583.

Loop 3 3' bottom primer (SEQ ID NO:43):

5'CTAGCTTAAGCATGCATACAGGTACTG-GTCGATGAGAGGATT-3'

The gcatgc is a SphI site, and the cttaag is an Afl II site. These two sites overlap by one base pair. The homology with the AAV sequence starts at position 3505 and ends at 3531 (note that this is the bottom strand).

These primers remove 24 bp (i.e., 8 amino acids) of AAV type 2 sequences from 3532 to 3555. The deleted amino acid sequence is Tyr Leu Ser Arg Thr Asn Thr Pro from at amino acid 444 to 451 (VP1-Met being amino acid #1).

The 5'Sph I Afl II Bgl II 3' sites in the sequence: 5'-GCATGCTTAAGATCT-3' result in the addition of 5 amino acids Ala Cys Leu Arg Ser.

Virus is produced by standard packaging methods. The MSH-tagged AAV type 2 vector is evaluated for transduction in HeLa cells and cells with MSH receptors (e.g., melanocytes).

EXAMPLE 20

Chimeric AAV2/4 Virus—Capsid Protein Substitutions

The virions of the AAV serotypes are made up of three protein subunits VP1 VP2 and VP3. VP3 is the most abundant subunit, it represents between 80–90% of the 60 subunits that make up the virion, with VP1 and VP2 making up 5–10% each of the virion. The subunits are translated from an overlapping transcript, so that VP3 sequences are within both VP2 and VP1, and VP2 sequences are within VP1.

We have designed primers that enabled us to substitute entire subunits and unique domains of subunits between AAV2 and AAV4. AAV4 has properties that are significantly different from AAV2. Thus, defining the domains that account for these distinct properties would be of value, e.g., for designing gene therapy vectors.

We have chosen a seamless cloning strategy to clone the subunits or unique domains of subunits between these two serotypes.

```
AAV2 and AAV4 top primer
5'-TGC CGA GCC ATC GAC GTC AGA CGC    (SEQ ID NO:44)
                             G-3':

AAV2 and AAV4 bottom primer
 5'-CAT GAT GCA TCA AAG TTC AAC TGA (SEQ ID NO:45)
                        AAC GAA T-3':

AAV2 VP3 top primer
 5'-CGA GCT CTT CGA TGG CTA GAG GCA (SEQ ID NO:46)
                    GTG GCG GAC-3':

AAV2 VP3 bottom primer
 5'-AGC GCT CTT CCC ATC GTA TTA GTT (SEQ ID NO:47)
                    CCC AGA CCA GAG-3':

AAV2 VP2 top primer
 5'-CGA GCT CTT CGA CGG CTC CGG GAA (SEQ ID NO:48)
                    AAA AGA GGC-3':

AAV2 VP2 bottom primer
 5'-AGC GCT CTT CCC GTC TTA ACA GGT (SEQ ID NO:49)
                    TCC TCA ACC AGG-3':

AAV4 VP3 top primer
 5'-CGA GCT CTT CGA TGC GTG CAG CAG (SEQ ID NO:50)
                    CTG GAG GAG CTG-3':

AAV4 VP3 bottom primer
 5'-AGC GCT CTT CGC ATC TCA CTG TCA (SEQ ID NO:51)
                    TCA GAC GAG TCG-3':

AAV4 VP2 top primer
 5'-CGA GCT CTT CGA CGG CTC CTG GAA (SEQ ID NO:52)
                    AGA AGA GAC-3':

AAV4 VP2 bottom primer
 5'-AGC GCT CTT CCC GTC TCA CCC GCT (SEQ ID NO:53)
                 TGC TCA ACC AGA- 3':
```

These primers will result in the subunit swaps that are shown in FIG. 7. A representative coding sequence of a chimeric AAV2 capsid in which the AAV4 Vp2 was substituted is shown in SEQ ID NO:2. This sequence contains the AAV2 rep coding sequences, most of the AAV2 Vp1 and Vp3 coding sequences, and the entire AAV4 Vp2 coding sequences and some of the AAV4 Vp1 and Vp3 coding sequences in a pBluescript backbone.

The Rep68/78 coding sequence begins at nu 251 of SEQ ID NO:2, and the Rep52/40 coding sequence begins at nu 923. The Rep78/52 stop signal ends at nu 2114, and the stop for Rep68/40 is at nu 2180. The capsid coding sequence starts at nu 2133 and the end at nu 4315 (Vp1 start at nu 2133, Vp2 start at nu 2544, Vp3 start at 2724).

The AAV2 sequences from the second XhoI site at bp 2420 in Vp1 to the Bsi WI site at bp 3255 in Vp3 in the AAV2 cap genes was replaced with the corresponding region from AAV4 (corresponding to nu 2350–3149 in the plasmid sequence). Briefly, the AAV2 helper plasmid pACG2 was partially digested with XhoI and Bsi WI releasing the 835 bp fragment. The same digest in AAV4 resulted in a 799 bp fragment that was ligated into the deleted AAV2 sequence to produce the helper virus encoding the chimeric AAV2/4 capsid.

Virions are produced carrying a recombinant AAV genome, preferably a recombinant AAV2 genome, typically expressing a reporter gene (e.g., GFP). These mutant viral vectors are characterized for virion formation, morphology, genome protection, heparin binding, and infectivity as described in Example 15.

EXAMPLE 21

Construction of B19/AAV-2 Chimeric Vectors

Studies by Dong et al., (1996) *Human Gene Therapy* 7:2101, have determined the packaging limitations using rAAV vectors. Using recombinant AAV DNA templates with increasing insertions of stuffer DNA, Dong et al. determined that the packaging capacity of rAAV vectors declined dramatically between 104% and 108% of wt (4883 vs. 5083 nucleotides, respectively). This packaging restriction precludes the use of important genes, including mini muscular dystrophy genes as well as promoter regulated cystic fibrosis sequences.

Accordingly, the present investigations set out to develop a B19/AAV-2 derived gene therapy vector that maintains the packaging capacity of B19, the tropism of AAV-2, as well as function as a substrate for targeting vectors. The human parvovirus B19 (packaging capacity of 5.6 kb) was chosen to utilize the major structural protein Vp2 in the generation of a chimeric AAV vector for packaging larger vector genomes. B19 is composed of only two overlapping structural proteins (Vp1 & 2). B19 infects primary erythroid progenitor cells using globoside as its receptor (Brown et al., (1993) *Science* 262:114). The structure of B19 has been determined to 8Δ resolution (Agbandje-McKenna et al., (1994) *Virology* 203:106).

A chimeric AAV particle was constructed by swapping the AAV major structural protein Vp3 for B19's Vp2. Seamless cloning (Stratagene USA) was utilized to generate an AAV helper construct that would express all of the AAV proteins (Rep 78, 68, 52, 40 and Vp 1 and Vp2) with B19 substituted for the Vp3 major Cap protein (FIG. 8; nucleotide sequence in SEQ ID NO:3; amino acid sequence in SEQ ID NO:4).

The starting material for the chimeric vector was pAAV-Ad and pYT103c. pYT103c contains the entire B19 coding domain without terminal repeats. HindIII digestion of pAAV-Ad released a 2727 bp fragment which contained the entire AAV2 capsid coding region and some flanking regions. This fragment was subcloned into Hind III digested pBS+(Stratagene), resulting in pBS+AAVCap. Polymerase chain reaction was used to amplify the Vp2 coding region from pYT103c. The primers were 5'-AGTTACTCTTCCATGACTTCAGTTAATTCTGCAGAA 3'(SEQ ID NO:54) in the 5' direction and 5'-AGTTACTCTTCTTTACMTGGGTGCACACGGCTTTT 3' (SEQ ID NO:55) in the 3' direction. Primers to pBS+AAVCap were used to amplify around Vp3 of AAV2. The primers were 5'AGTTACTCTTCTTMTCGTGGACTTACCGTGGATAC 3' (SEQ ID NO:56) in the 5' direction and 5'-AGTTACTCTTCCCATCGTATTAGTTCCCAGACCAGA 3 (SEQ ID NO:57), in the 3' direction. Six nucleotides from the 5' end of each primer is an Eam 1104 I site, this site digests downstream from its recognition site in this case the overlap is an ATG and its compliment and a TAA and its compliment. This site is utilized during the seamless cloning strategy (Stratagene). Digestion of B19-Vp2 and AAV2 PCR products with Eam 1104-I and cloning resulted in a subclone of pBS+AAVCap with Vp2 of B19 substituted for AAV2 Vp3. This vector was digested with Hind III and cloned back into pAAV-Ad and orientation determined resulting in pAAV/B19-Ad (SEQ ID NO:3). This sequence encodes the AAV2 Vp1 region (start at nt 1), followed by the AAV2 Vp2 region (start at nt 412), and then the B19 Vp2 region (start at nt 607).

EXAMPLE 22

Production of Chimeric Virus

The pAAV/B19 helper construct was used in a transient packaging system as described in Example 1. Briefly, the helper plasmids pAAV/B19-Ad and pAB11 (which contains AAV2 terminal repeats and the β-galactosidase gene under the control of the CMV early promoter) were co-transfected into 293 cells by calcium phosphate. Twelve hours after transfection the medium was changed and adenovirus dl309 (MOI-5) was added. Forty-eight hours later the cells were centrifuged and the supernatant was discarded. A fraction of the cell pellet was used in a HIRT assay. The cell pellet was lysed in cesium chloride (1.39 g/ml), sonicated and centrifuged at 41,000 rpm for 72 hours. Fractions from the cesium gradient were recovered and samples from each were used in dot blot hybridization to test particle number of virus. The dot blots were probed with β-galactosidase gene, and particle numbers were determined by control amounts of the β-galactosidase gene. Peak fractions containing virus were dialysed against PBS, 20% glycerol.

EXAMPLE 23

Infection of Cells with Chimeric Virus

Forty-eight hours post-transfection, cell lysates were generated and tested for transduction into various target cells. A transducing titer of $2\times10^6$ was generated. Various volumes of virus were added to 293, RT-2 rat glioma, U-87 glioma, as well as to two primary human glioblastoma cell lines in small volumes of medium. Virus was also added to UT7 megakaryoctye cells that had been incubated in the presence of erythropoeitin (EPO) for several weeks. Exposure of UT7 cells to EPO is known to render these cells permissive for B19 infection.

Adenovirus was also added to the cells at an MOI of 5. Two hours after infection the virus was washed off and fresh medium was added. Twenty-four hours post infection the cells were washed with PBS, fixed in formaldehyde/gluteraldehyde, and stained with X-gal. Twelve to twenty-four hours later the number of blue cells was determined by counting ten fields.

Transduction was obtained in the glioma and primary human glioblastoma cells. Efficient transduction was not observed in 293 cells (a cell type typically infected with AAV). Interestingly, transduction was seen with the UT7 cells. These results suggest that the chimera has lost the native AAV tropism and has acquired the B19 tropism for erythroid cells. This virus is characterized to determine whether it has retained the antigenic properties associated with the AAV2 serotype.

The B19 globoside binding region (loop 4 between amino acids 399–406 of the Vp2 subunit; Brown et al. (1993) *Science* 262:114 virus of this is chimeric virus is deleted, modified or swapped out to reduce or completely eliminate the B19 tropism for erythroid cells.

EXAMPLE 24

Characterization of B19/AAV Chimera

The results from Example 23 indicate that a transducing chimeric virus was successfully generated. The chimeric virus was further evaluated for total particle yield and integrity. The remainder of the vector preparation was gradient purified, and the chimeric virus was analyzed by dot blot analysis to determine a particle titer of $1\times10^8$ and EM analysis (see Example 6) to determine if a correct icosahedral structure was formed (FIG. 9). From this analysis, it was confirmed that the chimeric virion that was generated retained the typical parvovirus structure and was stable to physical purification step such as sonication and $CsCl_2$ gradient centrifugation. This is an important observation since most parvovirus are heat stable (resistant up to 65 degrees), resistant to detergents (0.5% SDS) and can tolerate extreme pH changes (viable between pH 2.0–11).

In addition, EM analysis yielded unexpected results (FIG. 9). Virion particles of two different sizes were observed (a 23–28 nm particle, typical for wt AAV, and a 33–38 nm particle, never before identified). Further analysis suggested that the AAV 33–38 nm particle was formed by changing the triangulation number from T=1 to T=3, resulting in larger particles containing 180 copies of the major capsid component instead of 60. These surprising results indicate that a virion structure larger than wt AAV has been generated. This virion may have the potential for carrying larger than wt vector templates. The larger 33–38 nm particle will be useful in increasing packaging limits above the 6 kb range (the B19 25 nm particle packages 6 kb of DNA).

EXAMPLE 25

Packaging Capacity of B19/AAV-2 Chimera

To quantitate the packaging capacity of the chimeric virus from Example 21, a series of vectors developed by Dong and coworkers, (1996) *Human Gene Therapy* 7:2101, is utilized with genomes of progressively increased sizes having inserts between 745 and 1811 bases (for a maximum total genome size of 6.4 kb). Small-scale production of chimeric recombinant virus is used to assay packaging efficiency by testing the DNA content of the virus using Hirt assay, and by chloramphenicol acetyltransferase (CAT) reporter assay.

EXAMPLE 26

Construction of Other B19/AAV Chimeras

Other chimeric B19/AAV capsids are generated as in Example 21 (e.g., swapping AAV Vp1 or Vp2 with B19 Vp1) and are characterized as described in Examples 22–25 above. In particular, both B19 Vp1 and Vp2 are substituted into an AAV Vp1 chimera to generate a novel chimeric capsid containing AAV Vp1 and B19 Vp1 and Vp2.

These chimeras are assayed in 293 (typically infected by AAV) and erythroid cells (the cell type typically infected by B19) for transduction efficiency and are assayed for packaging recombinant AAV vectors with increasing sized inserts as described above.

If desired, the B19 globoside binding region (loop 4 of Vp2 between amino acids 399–406; Brown et al. (1993) *Science* 262:114) of these vectors can be deleted, modified or swapped out to remove the B19 tropism.

EXAMPLE 27

Loop Swaps Between AAV Serotypes

The capsid gene of AAV2, in the helper vector pACG2, was digested with the enzymes Asp718 and Bsi WI. Bsi WI has a unique site in the AAV2 genome at position 3254 bp, and Asp718 digests the genome twice at 1906 and 4158 bps (AAV2 sequence numbers). The capsid coding domain of AAV2 was partially digested with Asp718 and the full length (single cut) fragment was isolated. This fragment was then digested with Bsi WI and the 7272 bp fragment isolated. This fragment removed the 904 bp fragment the contains the coding region of the VP3 loop 2, 3, and 4 domains.

The capsid gene of AAV4 was digested with Asp718 and Bsi WI to completion and a 928 bp fragment from 3284 bp (BsiWI) to 4212 bps (Asp718) was isolated (AAV4 sequence numbers). This AAV4 fragment codes for a region in VP3 that contains loops 2, 3 and 4. The 928 bp AAV4 fragment and the 7272 bp fragment from pACG2 were ligated and clones were identified.

These clones were used to make a chimeric virus that contained mostly AAV2 and part of the VP3 domain of AAV4. This virus did not infect HeLa cells as determined by blue stained cells (viral infected cells expressing the LacZ marker gene). However, like AAV4 these cells infected COS7 cells at a low titer of $1\times10^5$ transducing units/mL. These virions are not recognized by the AAV2 monoclonal antibody B1

Chimeric virus was also made in which Vp3 Loops 2–4 from AAV2 were substituted into the homologous region of the AAV4 capsid.

The AAV3 capsid coding region containing the VP3 loops 2–4 domains were cloned into pACG2 in the same manner as described above for AAV2/4 loop swaps. These chimeric AAV2/3 virions bind heparin agarose and infect HeLa and 293 cells. Furthermore, these virions are recognized by the B1 monoclonal antibody.

Likewise, using the techniques taught above, Vp3 loops 2–4 from AAV5 are substituted for loops 2–4 of AAV2.

Furthermore, single loops (e.g., loop 2, 3 or 4, or loops 2–3 or 3–4) are substituted from AAV3, 4 or 5 into AAV2 or vice versa.

These mutant viral vectors are characterized for virion formation, morphology, genome protection, heparin binding, and infectivity as described in Example 4–7.

A representative helper plasmid encoding a chimeric AAV2/3 capsid is given in SEQ ID:5. This sequence contains the AAV2 rep coding sequences, most of the AAV2 capsid coding sequences, with the exception that loops 2–4 from the AAV2 Vp3 subunit were replaced with the corresponding region from AAV3, in a pBluescript backbone. The Rep 68/78 coding sequence starts at nu 251, and the Rep52/40 coding sequence starts at nu 923. The rep coding sequences end at nu 2114 for Rep78/52 and at nu 2180 for Rep68/40. The cap coding region starts at nu 2133 and ends at nu 4342 (Vp1 start at nu 2133, Vp2 start at nu 2544, Vp3 start at nu 2739).

Briefly, both AAV2 (pACG2) and AAV3 helper plasmids were digested with Bsi WI and Asp 718. This removes a 904 bp fragment in the AAV2 genome from nu 3255 to 4159. In the AAV3 genome, the same digestion removed 907 bp from nu 3261–4168. This 904 bp fragment was ligated into the deleted AAV2 helper to result in the helper given in SEQ ID NO:5 (AAV3 sequences at nu 3184–4092 of the plasmid).

EXAMPLE 28

Hybrid Viruses

Primers were made to create a unique Hind III site in the AAV4 rep gene that overlapped the Hind III site in AAV2. In addition, at the 3' end of the rep coding sequence, a unique Not I site was created 3' of the polyadenylation site. A virus purchased from American Type Culture Collection (ATCC) as the template for the PCR.

The 5' portion of the AAV2 rep gene from the Xba I site to the Hind III site was subcloned into pBluescript. The Hind III-Not I PCR digestion product was then cloned into the pBluescript containing the 5' rep gene digested with Not I and Hind III.

```
Primers:
AAV4 3'Not I primer
5'-AAG CGC CGC GGC CGC TGC TTA TGT    (SEQ ID NO:58):
                            ACG CA-3'

AAV4 5'Hind III primer
5'-GAC GCG GAA GCT TCG GTG GAC TAC (SEQ ID NO:59):
                            GCG-3'
```

This cloning strategy resulted in a helper plasmid that is a hybrid for AAV2 and AAV4 rep genes and contains the AAV4 cap genes. This helper contains the AAV2 rep gene up to the Hind III site and from this past the polyadenylation site the sequences are derived from AAV4.

This virus packaged a recombinant AAV2 genome with AAV2 ITRs. This hybrid AAV2/4 virus exhibits the binding characteristics of AAV4, e.g., it does not bind HS and transduces AAV4 target cells that are not typically permissive to AAV2 transduction.

The hybrid AAV 2/4 helper plasmid is as given in SEQ ID NO:1. This sequence encodes the AAV2 rep genes and AAV4 capsid in a pBluescript backbone. The Rep 68/78 coding sequence starts at nu 251, and the Rep52/40 coding sequence starts at nu 923. The rep coding sequences end at nu 2120 for Rep78/52 and at nu 2183 for Rep68/40. The cap coding region starts at nu 2123 and ends at nu 4341 (Vp1 start at nu 2123, Vp2 start at nu 2547, Vp3 start at nu 2727).

Using the same techniques, a hybrid AAV2/3 virus in which a recombinant AAV2 genome (with AAV2 ITRs) is packaged. The resulting hybrid virus is viable and efficiently transduces AAV3 permissive cells.

In addition, in contrast to a recent report (Chiorini et al., 1999) *J. Virology* 73:1309), the techniques described above have been used to produce a hybrid AAV2/5 virus in which a recombinant AAV2 genome (with AAV2 ITRs) is packaged within a AAV Type 5 capsid. This virus is packaged relatively inefficiently, but the resulting particles demonstrated transduction of cells.

Although the foregoing invention has been described in some detail by way of illustration and example for purposes of clarity and understanding, it will be apparent that certain changes and modifications may be practiced within the scope of the appended claims and equivalents thereof.

---

That which is claimed is:

1. A hybrid virus particle comprising:
    a parvovirus capsid; and
    a nucleic acid comprising at least one adeno-associated virus (AAV) serotype 2 inverted terminal repeat packaged within said parvovirus capsid, subject to the proviso that if said parvovirus capsid is an AAV capsid, the serotypes of said AAV capsid and said at least one AAV inverted terminal repeat are different.

2. The hybrid virus particle of claim 1, wherein said nucleic acid comprises at least one heterologous nucleotide sequence.

3. The hybrid virus particle of claim 2 comprising two AAV inverted terminal repeats that flank said at least one heterologous nucleotide sequence.

4. The hybrid virus particle of claim 2, wherein said at least one heterologous nucleotide sequence encodes a protein or peptide.

5. The hybrid virus particle of claim 4, wherein said protein or peptide is a therapeutic protein or peptide.

6. The hybrid virus particle of claim 4, wherein said protein or peptide is an immunogenic protein or peptide.

7. The hybrid virus particle of claim 4, wherein said at least one heterologous nucleotide sequence encodes dystrophin, a mini-dystrophin, a clotting factor, β-glucocerebrosidase, erythropoietin, cystic fibrosis transmembrane regulator protein, a cytokine, β-globin, a hormone, α-globin or a growth factor.

8. The hybrid virus particle of claim 2, wherein said at least one heterologous nucleotide sequence encodes an untranslated RNA.

9. The hybrid virus particle of claim 1, wherein said parvovirus capsid is an autonomous parvovirus capsid.

10. The hybrid virus particle of claim 1, wherein said parvovirus capsid is a B19 capsid.

11. The hybrid virus particle of claim 1, wherein said parvovirus capsid is an AAV capsid.

12. The hybrid virus particle of claim 11, wherein:
said AAV capsid is of a serotype selected from the group consisting of AAV serotypes 1, 3, 4, 5 and 6.

13. The hybrid virus particle of claim 12 selected from the group consisting of:
(a) a hybrid virus particle comprising an AAV serotype-1 capsid and at least one AAV serotype-2 inverted terminal repeat.
(b) a hybrid virus particle comprising an AAV serotype-3 capsid and at least one AAV serotype-2 inverted terminal repeat,
(c) a hybrid virus particle comprising an AAV serotype-4 capsid and at least one AAV serotype-2 inverted terminal repeat,
(d) a hybrid virus particle comprising an AAV serotype-5 capsid and at least one AAV serotype-2 inverted terminal repeat, and
(e) a hybrid virus particle comprising an AAV serotype-6 capsid and at least one AAV serotype-2 inverted terminal repeat.

14. The hybrid virus particle of claim 1, wherein said nucleic acid does not comprise AAV cap genes or AAV rep genes.

15. A pharmaceutical formulation comprising the hybrid virus particle of claim 1 in a pharmaceutically-acceptable carrier.

16. An isolated nucleic acid for producing the hybrid virus particle of claim 1, wherein said isolated nucleic acid comprises parvovirus cap genes and adeno-associated virus (AAV) rep genes, subject to the proviso that if said parvovirus cap genes are AAV cap genes, the serotypes of said AAV cap genes and said AAV rep genes are different.

17. The isolated nucleic acid of claim 16, wherein said parvovirus cap genes are operably associated with an authentic parvovirus promoter.

18. The isolated nucleic acid of claim 16, wherein said parvovirus cap genes are B19 cap genes.

19. The isolated nucleic acid of claim 18, wherein said AAV rep genes are AAV serotype-2 rep genes.

20. The isolated nucleic acid of claim 16, wherein said cap genes are AAV cap genes.

21. The isolated nucleic acid of claim 20, wherein said AAV cap genes are operably associated with an authentic AAV promoter.

22. The isolated nucleic acid of claim 21, wherein said authentic AAV promoter is an AAV p40 promoter.

23. The isolated nucleic acid of claim 20, wherein:
said AAV cap genes are of a serotype selected from the group consisting of AAV serotypes 1, 3, 4, 5 and 6; and
said AAV rep genes are of a serotype selected from the group consisting of AAV serotypes 1, 2, 3, 4, 5 and 6.

24. The isolated nucleic acid of claim 23 selected from the group consisting of:
(a) an isolated nucleic acid comprising AAV serotype-1 cap genes and AAV serotype-2 rep genes,
(b) an isolated nucleic acid comprising AAV serotype-3 cap genes and AAV serotype-2 rep genes,
(c) an isolated nucleic acid comprising AAV serotype-4 cap genes and AAV serotype-2 rep genes,
(d) an isolated nucleic acid comprising AAV serotype-5 cap genes and AAV serotype-2 rep genes, and
(e) an isolated nucleic acid comprising AAV serotype-6 cap genes and AAV serotype-2 rep genes.

25. A vector comprising the isolated nucleic acid of claim 16.

26. The vector of claim 25, wherein said vector is selected from the group consisting of plasmids, naked DNA vectors, bacterial artificial chromosomes, yeast artificial chromosomes, and viral vectors.

27. The vector of claim 26, wherein said vector is a plasmid.

28. A cell comprising the vector of claim 25.

29. The cell of claim 28, wherein said cell is selected from the group consisting of bacterial, protozoan, yeast, fungus, plant, and animal cells.

30. A method of delivering a nucleotide sequence to a cell, in vitro comprising introducing into a cell the hybrid virus particle according to claim 2.

31. The method of claim 30, wherein the heterologous nucleotide sequence is expressed in the cell.

32. The method of claim 31, wherein the protein or peptide is an immunogenic protein or peptide.

33. The method of claim 30, wherein the parvovirus capsid is a B19 capsid.

34. The method of claim 30, wherein the at least one heterologous nucleotide sequence encodes a protein or peptide.

35. The method of claim 34, wherein the protein or peptide is a therapeutic protein or peptide.

36. The method of claim 34, wherein the at least one heterologous nucleotide sequence encodes dystrophin, a mini-dystrophin, a clotting factor, β-glucocerebrosidase, or a growth factor.

37. The method of claim 30, wherein the heterologous nucleotide sequence encodes an untranslated RNA.

38. The method of claim 30, wherein the cell is selected from the group consisting of a neural cell, lung cell, retinal cell, epithelial cell, muscle cell, pancreatic cell, hepatic cell, myocardial cell, bone cell, spleen cell, keratinocyte, fibroblast, endothelial cell, prostate cell, germ cell, progenitor cell, and a stem cell.

39. The method of claim 30, wherein the parvovirus capsid is an AAV capsid.

40. The method of claim 39, wherein:
the AAV capsid is of a serotype selected from the group consisting of AAV serotypes 1, 3, 4, 5 and 6.

41. The method of claim 40, wherein the hybrid virus particle is selected from the group consisting of:
(a) a hybrid virus particle comprising an AAV serotype-1 capsid and at least one AAV serotype-2 inverted terminal repeat, (b) a hybrid virus particle comprising an AAV serotype-3 capsid and at least one AAV serotype-2 inverted terminal repeat,
(c) a hybrid virus particle comprising an AAV serotype-4 capsid and at least one AAV serotype-2 inverted terminal repeat,
(d) a hybrid virus particle comprising an AAV serotype-5 capsid and at least one AAV serotype-2 inverted terminal repeat,
(e) a hybrid virus particle comprising an AAV serotype-6 capsid and at least one AAV serotype-2 inverted terminal repeat.

42. A cell comprising a vector comprising:
parvovirus cap genes,
adeno-associated virus (AAV) rep genes, and
a nucleic acid comprising at least one AAV serotype 2 inverted terminal repeat,
subject to the proviso that if said parvovirus cap genes are AAV cap genes, said at least one AAV inverted terminal repeat is of a different AAV serotype than said cap genes.

43. The cell of claim 42, wherein said cell is a mammalian cell.

44. A cell comprising parvovirus cap genes and adeno-associated virus (AAV) rep genes stably integrated into the genome of the cell, subject to the proviso that if said parvovirus cap genes are AAV cap genes, the serotypes of said AAV cap genes and said AAV rep genes are different.

45. The cell of claim 44 further comprising a nucleic acid comprising at least one AAV serotype 2 inverted terminal repeat, subject to the proviso that if said parvovirus cap genes are AAV cap genes, the serotypes of said AAV cap genes and said at least one AAV inverted terminal repeat are different.

46. A method of producing a hybrid virus particle, comprising:
providing a cell with adeno-associated virus (AAV) rep genes, parvovirus cap genes, a nucleic acid comprising at least one AAV serotype 2 inverted terminal repeat, and helper functions for generating a productive AAV infection; subject to the proviso that if the parvovirus cap genes are AAV cap genes, the serotypes of the AAV cap genes and the at least one AAV inverted terminal repeat are different, and
allowing assembly of the hybrid virus particles.

47. The method of claim 46, further comprising collecting the hybrid virus particles.

48. The method of claim 46, wherein the nucleic acid comprises at least one heterologous nucleotide sequence.

49. The method of claim 46, wherein the parvovirus cap genes and AAV rep genes are provided by one or more transcomplementing packaging vectors.

50. The method of claim 46, wherein the parvovirus cap genes and AAV rep genes are provided by a plasmid.

51. The method of claim 46, wherein the parvovirus cap genes and AAV rep genes are provided by an adenovirus vector.

52. The method of claim 46, wherein the parvovirus cap genes and AAV rep genes are stably integrated into the genome of the cell.

53. The method of claim 46, wherein the parvovirus cap genes are AAV cap genes.

54. A hybrid virus particle produced by the method of claim 46.

* * * * *

UNITED STATES PATENT AND TRADEMARK OFFICE
CERTIFICATE OF CORRECTION

PATENT NO. : 7,172,893 B2  
APPLICATION NO. : 10/205942  
DATED : February 6, 2007  
INVENTOR(S) : Rabinowitz et al.

It is certified that error appears in the above-identified patent and that said Letters Patent is hereby corrected as shown below:

Column 19, Line 40: Please correct "give"
To read -- given --

Column 102, Lines 32-33:
Please correct "a cell, in vitro"
To read -- a cell in vitro, --

Signed and Sealed this

Eighteenth Day of March, 2008

JON W. DUDAS
*Director of the United States Patent and Trademark Office*

SEQUENCE LISTING

```
<160> NUMBER OF SEQ ID NOS: 59

<210> SEQ ID NO 1
<211> LENGTH: 7214
<212> TYPE: DNA
<213> ORGANISM: Adeno-associated virus
<220> FEATURE:
<221> NAME/KEY: misc_feature
<222> LOCATION: (1)..(7214)
<223> OTHER INFORMATION: AAV2/4 helper plasmid

<400> SEQUENCE: 1
ctgacgcgcc ctgtagcggc gcattaagcg cggcgggtgt ggtggttacg cgcagcgtga     60
ccgctacact tgccagcgcc ctagcgcccg ctcctttcgc tttcttccct tcctttctcg    120
ccacgttcgc cggctttccc cgtcaagctc taaatcgggg gctcccttta gggttccgat    180
ttagtgcttt acggcacctc gaccccaaaa aacttgatta gggtgatggt tcacgtagtg    240
ggccatcgcc ctgatagacg gtttttcgcc ctttgacgtt ggagtccacg ttctttaata    300
gtggactctt gttccaaact ggaacaacac tcaaccctat ctcggtctat tcttttgatt    360
tataagggat tttgccgatt tcggcctatt ggttaaaaaa tgagctgatt taacaaaaat    420
ttaacgcgaa ttttaacaaa atattaacgc ttacaatttc cattcgccat tcaggctgcg    480
caactgttgg gaagggcgat cggtgcgggc ctcttcgcta ttacgccagc tggcgaaagg    540
gggatgtgct gcaaggcgat taagttgggt aacgccaggg ttttcccagt cacgacgttg    600
taaaacgacg gccagtgagc gcgcgtaata cgactcacta tagggcgaat tggagctcca    660
ccgcggtggc ggccgctgct tatgtacgca gtagccatgg aaacgagata agataagaag    720
gacacggaga ccaaagttca actgaaacga ataaaccggt ttattgatta acaggttatt    780
```

```
acaggtggtg ggtgaggtag cgggtaccga tagccctagg ctcagtgtat ttcccagccg      840
catcgggagc ccacaacaga gagttttgct gtccgtagtt ggaggtaaac tggacctcgg      900
ggttccagcg tttggaccgc tccttctgga tctcccagtc aatctgcacc gacacctggc      960
cagtgctgta ctgagtaatg aaggagttta ccggagtaga gctgaaggtc gttgcaggat     1020
tcgcaggtac cggggtgttc ttgataaaaa tttgaggagg cgggtgtttc agcccaaacc     1080
caccaatcag cggtgagggg tgaaagtgtc catcggtatg aggaatcttg cccaaatgg      1140
gaccctggta gtaaatgtct ctgttttgcc agaccattcc aggcacggct cccaaggctg     1200
tcagtctgtc cacggtcggc aggttgctgt tgctctggtc accgccaggt aggttgcccc     1260
acatgtccgt atcggtggcg ttggtggctg ccagctcctc ctcagaggtg aagatcagag     1320
tcccgggtac ggtggccgtg ttgccgttct gtttaggccc cgcaaagatg agctggctgt     1380
tgctgaactt gctgtccgca ggtccagccg tggccattgg aggtccgggg gtcagggcac     1440
tccatcttcc gtccagagtg ctgtgcgtct cgtatttgat gagactgtct gacccggtgg     1500
cagggatctt gtagttttga ttggcagtct ttgagaagcc ctgctgcttg attgaaggcc     1560
cgggcagcca gttcttttta aagttggaaa agttggtagg ccgcagcttg gtaaagttgg     1620
tggtggcagt cccggcattc agggtggttc cggtggtggt cgattgcagt ccccacaggt     1680
actggtcgat gagagggttc atcagccggt ccaggctctg gctgtgcgcg tacatcgagt     1740
ggaaaggcac cttctcaaaa ctgtacgtaa tttcaaagtt gttgccagtc cgcagcatct     1800
gcgaaggaaa gtactccagg cagtagaagg catttctgtc agtctgttgc tgcgaagtgt     1860
tgccggtcac cagtccacag tagccgtact ggggcaccat aaagacgtcg ttgggaaaag     1920
gaggcaggct gccctcttga cccgcatcca tcacgtacgg cagttcgtac gacgagtccg     1980
caaagatctg aaccgtgctg gtaaggttat tagccaccgt tgtctcgccg ttcgacgtcg     2040
tgacctcctt gacctggatg ttgaagattt tgacccgcat ggctttggt cgcatgcccc      2100
agttgttgtt gatgagtcgc tgccagtcac gtggtgagaa gtggcagtgg aagcggttga     2160
agtcaaagta tccccagggg gtggagaatc cgttgtaggt gttggactgc aggctctctc     2220
cgagtcgctt gtagaggtgg ttgttgtagg tgggcaagac ccaggttctg gtgctggtgg     2280
tcgtgacgtg gccctcagac caggtggaat cgcaatgcca atcacccgag gcattaccca     2340
ctccatcggc accttgtccg ccctcgactg cagctccgcc agctgctgca cgcatctcac     2400
tgtcatcaga catggctccg gaagttgatc cctcaggggg tccgtcgcct gctccagttt     2460
cgtcttcgaa aacgagcttc ttttttagccg gctgcttgcc ttttttgccg ataccgtgg     2520
aggagtcggg ctgctggggg gattcaatca acggtctctt ctttccagga gccgtctcac     2580
ccgcttgctc aaccagacca agaggttcaa gaaccctctt tttggcctgg aagactgctc     2640
tgccgaggtt gccccaaac gatgtgtcgc cctgaagccg ctgctggaac tccgcgtcgg      2700
cgtggttgta cttgaggtag gggttgtcac cggccttgag ctgctggtcg taggccttgt     2760
cgtgctcgag ggctgccgcg tccgctgcgt tgacgggttc ccccttgtcg agtccgttgc     2820
cgggtccgag gtatttgtaa cccggaagca caagaccccg agcgttgtcc tgatgttgtt     2880
gatttgcctt gggtttaggg gctccaggtt gcagcgccca ccactctcga acgccttcag     2940
agaggttgtc ctctagccaa tctggaaggt aaccgtcagt catatctggt ttgagtcatt     3000
tattgttcca tgtcacagtc atccaagtcc acattggcca gttcgcaggc cgagcaggcc     3060
acctcgggcg ccctccccat gatgtgatga atcggacaca gtttctgata cgtccgcttt     3120
ctgacgacag acacggggttg agattctgac acggggaagc actcggcaca gtccatgacc     3180
```

```
ccgtgcgtga agcaaatgtc cacattctga ttcattctct cgcattgccg gcagggaaaa    3240
agcatcagat tcatacccac gtgacgagaa catttgtttt ggtacctgtc cgcgtagtcc    3300
accgaagctt ccgcgtctga cgtcgatggc tgcgcaactg actcgcgcac ccgtttgggc    3360
tcacttatat ctgcgtcact gggggcgggt cttttcttgg ctccacccett tttgacgtag    3420
aattcatgct ccacctcaac cacgtgatcc tttgcccacc ggaaaaagtc tttgacttcc    3480
tgcttggtga ccttcccaaa gtcatgatcc agacggcggg tgagttcaaa tttgaacatc    3540
cggtcttgca acggctgctg gtgttcgaag gtcgttgagt tcccgtcaat cacggcgcac    3600
atgttggtgt tggaggtgac gatcacggga gtcgggtcta tctgggccga ggacttgcat    3660
ttctggtcca cgcgcacctt gcttcctccg agaatggctt tggccgactc cacgaccttg    3720
gcggtcatct tcccctcctc ccaccagatc accatcttgt cgacacagtc gttgaaggga    3780
aagttctcat tggtccagtt tacgcacccg tagaagggca cagtgtgggc tatggcctcc    3840
gcgatgttgg tcttcccggt agttgcaggc ccaaacagcc agatggtgtt cctcttgccg    3900
aacttttttcg tggcccatcc cagaaagacg gaagccgcat attggggatc gtacccgttt    3960
agttccaaaa ttttataaat ccgattgctg gaaatgtcct ccacgggctg ctggcccacc    4020
aggtagtcgg gggcggtttt agtcaggctc ataatctttc ccgcattgtc caaggcagcc    4080
ttgatttggg accgcgagtt ggaggccgca ttgaaggaga tgtatgaggc ctggtcctcc    4140
tggatccact gcttctccga ggtaatcccc ttgtccacga gccacccgac cagctccatg    4200
tacctggctg aagtttttga tctgatcacc ggcgcatcag aattgggatt ctgattctct    4260
ttgttctgct cctgcgtctg cgacacgtgc gtcagatgct cgccaccaa ccgtttacgc     4320
tccgtgagat tcaaacaggc gcttaaatac tgttccatat tagtccacgc ccactggagc    4380
tcaggctggg ttttggggag caagtaattg gggatgtagc actcatccac caccttgttc    4440
ccgcctccgg cgccatttct ggtctttgtg accgcgaacc agtttggcaa agtcggctcg    4500
atcccgcggt aaattctctg aatcagtttt tcgcgaatct gactcaggaa acgtcccaaa    4560
accatggatt tcaccccggt ggtttccacg agcacgtgca tgtggaagta gctctctccc    4620
ttctcaaatt gcacaaagaa aagggcctcc ggggccttac tcacacggcg ccattccgtc    4680
agaaagtcgc gctgcagctt ctcggccacg gtcaggggtg cctgctcaat cagattcaga    4740
tccatgtcag aatctggcgg caactcccat tccttctcgg ccacccagtt cacaaagctg    4800
tcagaaatgc cggcagatg cccgtcaagg tcgctgggga ccttaatcac aatctcgtaa     4860
aaccccggca tgcggctgc gcgttcaaac ctcccgcttc aaaatggaga ccctgcgtgc     4920
tcactcgggc ttaaataccc agcgtgacca catggtgtcg caaatgtcg caaaacactc      4980
acgtgacctc taatacagga ctctagcggt acccagcttt tgttccettt agtgagggtt    5040
aattgcgcgc ttggcgtaat catggtcata gctgtttcct gtgtgaaatt gttatccgct    5100
cacaattcca cacaacatac gagccggaag cataaagtgt aaagcctggg gtgcctaatg    5160
agtgagctaa ctcacattaa ttgcgttgcg ctcactgccc gctttccagt cgggaaacct    5220
gtcgtgccag ctgcattaat gaatcggcca acgcgcgggg agaggcggtt tgcgtattgg    5280
gcgctcttcc gcttcctcgc tcactgactc gctgcgctcg gtcgttcggc tgcggcgagc    5340
ggtatcagct cactcaaagg cggtaatacg gttatccaca gaatcagggg ataacgcagg    5400
aaagaacatg tgagcaaaag gccagcaaaa ggccaggaac cgtaaaaagg ccgcgttgct    5460
ggcgtttttc cataggctcc gccccccctga cgagcatcac aaaaatcgac gctcaagtca    5520
```

```
gaggtggcga aacccgacag gactataaag ataccaggcg tttccccctg gaagctccct      5580
cgtgcgctct cctgttccga ccctgccgct taccggatac ctgtccgcct ttctcccttc      5640
gggaagcgtg gcgctttctc atagctcacg ctgtaggtat ctcagttcgg tgtaggtcgt      5700
tcgctccaag ctgggctgtg tgcacgaacc ccccgttcag cccgaccgct gcgccttatc      5760
cggtaactat cgtcttgagt ccaacccggt aagacacgac ttatcgccac tggcagcagc      5820
cactggtaac aggattagca gagcgaggta tgtaggcggt gctacagagt tcttgaagtg      5880
gtggcctaac tacggctaca ctagaaggac agtatttggt atctgcgctc tgctgaagcc      5940
agttaccttc ggaaaaagag ttggtagctc ttgatccggc aaacaaacca ccgctggtag      6000
cggtggtttt tttgtttgca agcagcagat tacgcgcaga aaaaaggat ctcaagaaga       6060 tcctttgatc ttttctacgg ggtctgacgc tcagtggaac gaaaactcac gttaagggat      6120
tttggtcatg agattatcaa aaaggatctt cacctagatc cttttaaatt aaaaatgaag      6180
ttttaaatca atctaaagta tatatgagta aacttggtct gacagttacc aatgcttaat      6240
cagtgaggca cctatctcag cgatctgtct atttcgttca tccatagttg cctgactccc      6300
cgtcgtgtag ataactacga tacgggaggg cttaccatct ggccccagtg ctgcaatgat      6360
accgcgagac ccacgctcac cggctccaga tttatcagca ataaaccagc cagccggaag      6420
ggccgagcgc agaagtggtc ctgcaacttt atccgcctcc atccagtcta ttaattgttg      6480
ccgggaagct agagtaagta gttcgccagt taatagtttg cgcaacgttg ttgccattgc      6540
tacaggcatc gtggtgtcac gctcgtcgtt tggtatggct tcattcagct ccggttccca      6600
acgatcaagg cgagttacat gatcccccat gttgtgcaaa aaagcggtta gctccttcgg      6660
tcctccgatc gttgtcagaa gtaagttggc cgcagtgtta tcactcatgg ttatggcagc      6720
actgcataat tctcttactg tcatgccatc cgtaagatgc ttttctgtga ctggtgagta      6780
ctcaaccaag tcattctgag aatagtgtat gcggcgaccg agttgctctt gcccggcgtc      6840
aatacgggat aataccgcgc cacatagcag aactttaaaa gtgctcatca ttggaaaacg      6900
ttcttcgggg cgaaaactct caaggatctt accgctgttg agatccagtt cgatgtaacc      6960
cactcgtgca cccaactgat cttcagcatc ttttactttc accagcgttt ctgggtgagc      7020
aaaaacagga aggcaaaatg ccgcaaaaaa gggaataagg gcgacacgga aatgttgaat      7080
actcatactc ttcctttttc aatattattg aagcatttat cagggttatt gtctcatgag      7140
cggatacata tttgaatgta tttagaaaaa taaacaaata ggggttccgc gcacatttcc      7200
ccgaaaagtg ccac                                                        7214
```

<210> SEQ ID NO 2
<211> LENGTH: 8151
<212> TYPE: DNA
<213> ORGANISM: Adeno-associated virus
<220> FEATURE:
<221> NAME/KEY: misc_feature
<222> LOCATION: (1)..(8151)
<223> OTHER INFORMATION: AAV2/4 helper plasmid

<400> SEQUENCE: 2

```
aattcccatc atcaataata taccttatt tggattgaag ccaatatgat aatgagggg         60 tggagtttgt gacgtggcgc ggggcgtggg aacgggcgg gtgacgtagt agtctctaga       120
gtcctgtatt agaggtcacg tgagtgtttt gcgacatttt gcgacaccat gtggtcacgc      180 tgggtatttta agcccgagtg agcacgcagg gtctccattt tgaagcggga ggtttgaacg     240
cgcagccgcc atgccggggt tttacgagat tgtgattaag gtccccagcg accttgacgg      300
```

-continued

```
gcatctgccc ggcatttctg acagctttgt gaactgggtg gccgagaagg aatgggagtt    360
gccgccagat tctgacatgg atctgaatct gattgagcag gcacccctga ccgtggccga    420
gaagctgcag cgcgactttc tgacggaatg gcgccgtgtg agtaaggccc cggaggccct    480
tttctttgtg caatttgaga agggagagag ctacttccac atgcacgtgc tcgtggaaac    540 caccgggggtg aaatccatgg ttttgggacg tttcctgagt cagattcgcg aaaaactgat    600
tcagagaatt taccgcggga tcgagccgac tttgccaaac tggttcgcgg tcacaaagac    660
cagaaatggc gccggaggcg ggaacaaggt ggtggatgag tgctacatcc ccaattactt    720
gctccccaaa acccagcctg agctccagtg ggcgtggact aatatggaac agtatttaag    780
cgcctgtttg aatctcacgg agcgtaaacg gttggtggcg cagcatctga cgcacgtgtc    840
gcagacgcag gagcagaaca aagagaatca gaatcccaat tctgatgcgc cggtgatcag    900
atcaaaaact tcagccaggt acatggagct ggtcgggtgg ctcgtggaca agggattac    960 ctcggagaag cagtggatcc aggaggacca ggcctcatac atctccttca atgcggcctc   1020
caactcgcgg tcccaaatca aggctgcctt ggacaatgcg ggaaagatta tgagcctgac   1080
taaaaccgcc cccgactacc tggtgggcca gcagcccgtg gaggacattt ccagcaatcg   1140
gatttataaa attttggaac taaacgggta cgatccccaa tatgcggctt ccgtctttct   1200
gggatgggcc acgaaaaagt tcggcaagag gaacaccatc tggctgtttg ggcctgcaac   1260
taccgggaag accaacatcg cggaggccat agcccacact gtgcccttct acgggtgcgt   1320
aaactggacc aatgagaact ttcccttcaa cgactgtgtc gacaagatgg tgatctggtg   1380
ggaggagggg aagatgaccg ccaaggtcgt ggagtcggcc aaagccattc tcggaggaag   1440
caaggtgcgc gtgaccaga aatgcaagtc ctcggcccag atagacccga ctcccgtgat   1500
cgtcacctcc aacaccaaca tgtgcgccgt gattgacggg aactcaacga ccttcgaaca   1560
ccagcagccg ttgcaagacc ggatgttcaa atttgaactc acccgccgtc tggatcatga   1620
ctttgggaag gtcaccaagc aggaagtcaa agactttttc cggtgggcaa aggatcacgt   1680
ggttgaggtg gagcatgaat tctacgtcaa aaagggtgga gccaagaaaa gacccgcccc   1740
cagtgacgca gatataagtg agcccaaacg ggtgcgcgag tcagttgcgc agccatcgac   1800
gtcagacgcg gaagcttcga tcaactacgc agacaggtac caaaacaaat gttctcgtca   1860
cgtgggcatg aatctgatgc tgtttccctg cagacaatgc gagagaatga atcagaattc   1920
aaatatctgc ttcactcacg gacagaaaga ctgtttagag tgctttcccg tgtcagaatc   1980
tcaacccgtt tctgtcgtca aaaaggcgta tcagaaactg tgctacattc atcatatcat   2040
gggaaaggtg ccagacgctt gcactgcctg cgatctggtc aatgtggatt tggatgactg   2100
catctttgaa caataaatga tttaaatcag gtatggctgc cgatggttat cttccagatt   2160
ggctcgagga cactctctct gaaggaataa gacagtggtg gaagctcaaa cctgccccac   2220
caccaccaaa gcccgcagag cggcataagg acgacagcag gggtcttgtg cttcctgggt   2280
acaagtacct cggaccccttc aacgactcg caaggggaga gccggtcaac gaggcagacg   2340
ccgcggccct cgagcacgac aaggcctacg accagcagct caaggccggt gacaaccccct   2400 acctcaagta caaccacgcc gacgcggagt tccagcagcg gcttcagggc gacacatcgt   2460
ttgggggcaa cctcggcaga gcagtcttcc aggccaaaaa gaggggttctt gaacctcttg   2520 gtctggttga gcaagcgggt gagacggctc ctggaaagaa gagaccgttg attgaatccc   2580
cccagcagcc cgactcctcc acgggtatcg gcaaaaaagg caagcagccg gctaaaaaga   2640
```

```
agctcgtttt cgaagacgaa actggagcag gcgacggacc ccctgaggga tcaacttccg   2700
gagccatgtc tgatgacagt gagatgcgtg cagcagctgg cggagctgca gtcgagggcg   2760
gacaaggtgc cgatggagtg ggtaatgcct cgggtgattg gcattgcgat tccacctggt   2820
ctgagggcca cgtcacgacc accagcacca gaacctgggt cttgcccacc tacaacaacc   2880
acctctacaa gcgactcgga gagagcctgc agtccaacac ctacaacgga ttctccaccc   2940
cctggggata ctttgacttc aaccgcttcc actgccactt ctcaccacgt gactggcagc   3000
gactcatcaa caacaactgg ggcatgcgac ccaaagccat gcgggtcaaa atcttcaaca   3060
tccaggtcaa ggaggtcacg acgtcgaacg gcgagacaac ggtggctaat aaccttacca   3120
gcacggttca gatctttgcg gactcgtcgt acgaactgcc gtacgtcctc ggctcggcgc   3180
atcaaggatg cctcccgccg ttcccagcag acgtcttcat ggtgccacag tatggatacc   3240
tcaccctgaa caacgggagt caggcagtag gacgctcttc attttactgc ctggagtact   3300
ttccttctca gatgctgcgt accggaaaca actttacctt cagctacact tttgaggacg   3360
ttcctttcca cagcagctac gctcacagcc agagtctgga ccgtctcatg aatcctctca   3420
tcgaccagta cctgtattac ttgagcagaa caaacactcc aagtggaacc accacgcagt   3480
caaggcttca gttttctcag gccggagcga gtgacattcg ggaccagtct aggaactggc   3540
ttcctggacc ctgttaccgc cagcagcgag tatcaaagac atctgcggat aacaacaaca   3600
gtgaatactc gtggactgga gctaccaagt accacctcaa tggcagagac tctctggtga   3660
atccgggccc ggccatggca agccacaagg acgatgaaga aaagtttttt cctcagagcg   3720
gggttctcat ctttgggaag caaggctcag agaaaacaaa tgtgaacatt gaaaaggtca   3780
tgattacaga cgaagaggaa atcggaacaa ccaatcccgt ggctacggag cagtatggtt   3840
ctgtatctac caacctccag agaggcaaca gacaagcagc taccgcagat gtcaacacac   3900
aaggcgttct tccaggcatg gtctggcagg acagagatgt gtaccttcag ggcccatct   3960 gggcaaagat tccacacacg gacggacatt ttcaccccctc tccctcatg ggtggattcg   4020 gacttaaaca ccctcctcca cagattctca tcaagaacac cccggtacct gcgaatcctt   4080
cgaccacctt cagtgcggca aagtttgctt ccttcatcac acagtactcc acgggacagg   4140
tcagcgtgga gatcgagtgg gagctgcaga aggaaaacag caaacgctgg aatcccgaaa   4200
ttcagtacac ttccaactac aacaagtctg ttaatcgtgg acttaccgtg gatactaatg   4260
gcgtgtattc agagcctcgc cccattggca ccagatacct gactcgtaat ctgtaattgc   4320
ttgttaatca ataaaccgtt taattcgttt cagttgaact ttggtctctg cgtatttctt   4380
tcttatctag tttccatgct ctagactact acgtcacccg cccgttccc acgcccgcg   4440 ccacgtcaca aactccaccc cctcattatc atattggctt caatccaaaa taaggtatat   4500
tattgatgat gcatcgctgg cgtaatagcg aagaggcccg caccgatcgc ccttcccaac   4560
agttgcgcag cctgaatggc gaatggaatt ccagacgatt gagcgtcaaa atgtaggtat   4620
ttccatgagc gttttttcctg ttgcaatggc tggcggtaat attgttctgg atattaccag   4680
caaggccgat agtttgagtt cttctactca ggcaagtgat gttattacta atcaaagaag   4740
tattgcgaca acggttaatt tgcgtgatgg acagactctt ttactcggtg gcctcactga   4800
ttataaaaac acttctcagg attctggcgt accgttcctg tctaaaatcc ctttaatcgg   4860
cctcctgttt agctcccgct ctgattctaa cgaggaaagc acgttatacg tgctcgtcaa   4920
agcaaccata gtacgcgccc tgtagcgcgc cattaagcgc ggcgggtgtg gtggttacgc   4980
gcagcgtgac cgctacactt gccagcgccc tagcgcccgc tcctttcgct ttcttccctt   5040
```

```
cctttctcgc cacgttcgcc ggctttcccc gtcaagctct aaatcggggg ctcccttag    5100
ggttccgatt tagtgcttta cggcacctcg accccaaaaa acttgattag ggtgatggtt   5160
cacgtagtgg gccatcgccc tgatagacgg ttttcgccc tttgacgttg gagtccacgt    5220
tctttaatag tggactcttg ttccaaactg gaacaacact caaccctatc tcggtctatt   5280
cttttgattt ataagggatt ttgccgattt cggcctattg gttaaaaaat gagctgattt   5340
aacaaaaatt taacgcgaat tttaacaaaa tattaacgtt tacaatttaa atatttgctt   5400
atacaatctt cctgttttg gggcttttct gattatcaac cggggtacat atgattgaca    5460
tgctagtttt acgattaccg ttcatcgatt ctcttgtttg ctccagactc tcaggcaatg   5520
acctgatagc ctttgtagag acctctcaaa aatagctacc ctctccggca tgaatttatc   5580
agctagaacg gttaatatc atattgatgg tgatttgact gtctccggcc tttctcaccc    5640
gtttgaatct ttacctacac attactcagg cattgcattt aaaatatatg agggttctaa   5700
aaattttat ccttgcgttg aaataaaggc ttctcccgca aaagtattac agggtcataa    5760
tgttttggt acaaccgatt tagctttatg ctctgaggct ttattgctta attttgctaa    5820
ttctttgcct tgcctgtatg atttattgga tgttggaatt cctgatgcgg tattttctcc   5880
ttacgcatct gtgcggtatt tcacaccgca tatggtgcac tctcagtaca atctgctctg   5940
atgccgcata gttaagccag ccccgacacc cgccaacacc cgctgacgcg ccctgacggg   6000
cttgtctgct cccggcatcc gcttacagac aagctgtgac cgtctccggg agctgcatgt   6060
gtcagaggtt ttcaccgtca tcaccgaaac gcgcgagacg aaagggcctc gtgatacgcc   6120
tattttata ggttaatgtc atgataataa tggtttctta dacgtcaggt ggcacttttc    6180
ggggaaatgt gcgcggaacc cctatttgtt tatttttcta atacattca aatatgtatc    6240
cgctcatgag acaataaccc tgataaatgc ttcaataata ttgaaaaagg aagagtatga   6300
gtattcaaca tttccgtgtc gcccttattc ccttttttgc ggcattttgc cttcctgttt   6360
ttgctcaccc agaaacgctg gtgaaagtaa aagatgctga agatcagttg ggtgcacgag   6420
tgggttacat cgaactggat ctcaacagcg gtaagatcct tgagagtttt cgccccgaag   6480
aacgttttcc aatgatgagc acttttaaag ttctgctatg tggcgcggta ttatcccgta   6540
ttgacgccgg gcaagagcaa ctcggtcgcc gcatacacta ttctcagaat gacttggttg   6600
agtactcacc agtcacagaa aagcatctta cggatggcat gacagtaaga gaattatgca   6660
gtgctgccat aaccatgagt gataacactg cggccaactt acttctgaca acgatcggag   6720
gaccgaagga gctaaccgct tttttgcaca acatggggga tcatgtaact cgccttgatc   6780
gttgggaacc ggagctgaat gaagccatac caaacgacga gcgtgacacc acgatgcctg   6840
tagcaatggc aacaacgttg cgcaaactat taactggcga actacttact ctagcttccc   6900
ggcaacaatt aatagactgg atggaggcgg ataaagttgc aggaccactt ctgcgctcgg   6960
cccttccggc tggctggttt attgctgata atctggagc cggtgagcgt gggtctcgcg    7020
gtatcattgc agcactgggg ccagatggta agccctcccg tatcgtagtt atctacacga   7080
cggggagtca ggcaactatg gatgaacgaa atagacagat cgctgagata ggtgcctcac   7140
tgattaagca ttggtaactg tcagaccaag tttactcata tatactttag attgatttaa   7200
aacttcattt ttaatttaaa aggatctagg tgaagatcct ttttgataat ctcatgacca   7260
aaatccctta acgtgagttt tcgttccact gagcgtcaga ccccgtagaa aagatcaaag   7320
gatcttcttg agatcctttt tttctgcgcg taatctgctg cttgcaaaca aaaaaaccac   7380
```

-continued

```
cgctaccagc ggtggtttgt ttgccggatc aagagctacc aactctttt ccgaaggtaa       7440 ctggcttcag cagagcgcag ataccaaata ctgtccttct agtgtagccg tagttaggcc       7500
accacttcaa gaactctgta gcaccgccta catacctcgc tctgctaatc ctgttaccag       7560
tggctgctgc cagtggcgat aagtcgtgtc ttaccgggtt ggactcaaga cgatagttac       7620
cggataaggc gcagcggtcg ggctgaacgg ggggttcgtg cacacagccc agcttggagc       7680
gaacgaccta caccgaactg agataccta c agcgtgagct atgagaaagc gccacgcttc       7740
ccgaagggag aaaggcggac aggtatccgg taagcggcag ggtcggaaca ggagagcgca       7800
cgagggagct tccaggggga aacgcctggt atctttatag tcctgtcggg tttcgccacc       7860
tctgacttga gcgtcgattt ttgtgatgct cgtcaggggg gcggagccta tggaaaaacg       7920
ccagcaacgc ggccttttta cggttcctgg ccttttgctg gccttttgct cacatgttct       7980
ttcctgcgtt atccctgat tctgtggata accgtattac cgcctttgag tgagctgata       8040
ccgctcgccg cagccgaacg accgagcgca gcgagtcagt gagcgaggaa gcggaagagc       8100
gcccaatacg caaaccgcct ctccccgcgc gttggccgat tcattaatgc a               8151
```

<210> SEQ ID NO 3
<211> LENGTH: 2271
<212> TYPE: DNA
<213> ORGANISM: Adeno-associated virus
<220> FEATURE:
<221> NAME/KEY: misc_feature
<222> LOCATION: (1)..(2271)
<223> OTHER INFORMATION: B19/AAV chimeric capsid coding sequence
<220> FEATURE:
<221> NAME/KEY: CDS
<222> LOCATION: (1)..(2268)
<223> OTHER INFORMATION:

<400> SEQUENCE: 3

```
atg gct gcc gat ggt tat ctt cca gat tgg ctc gag gac act ctc tct        48
Met Ala Ala Asp Gly Tyr Leu Pro Asp Trp Leu Glu Asp Thr Leu Ser
1               5                  10                  15 gaa gga ata aga cag tgg tgg aag ctc aaa cct ggc cca cca cca cca        96
Glu Gly Ile Arg Gln Trp Trp Lys Leu Lys Pro Gly Pro Pro Pro Pro
            20                  25                  30 aag ccc gca gag cgg cat aag gac gac agc agg ggt ctt gtg ctt cct       144
Lys Pro Ala Glu Arg His Lys Asp Asp Ser Arg Gly Leu Val Leu Pro
        35                  40                  45 ggg tac aag tac ctc gga ccc ttc aac gga ctc gac aag gga gag ccg       192
Gly Tyr Lys Tyr Leu Gly Pro Phe Asn Gly Leu Asp Lys Gly Glu Pro
    50                  55                  60 gtc aac gag gca gac gcc gcg gcc ctc gag cac gac aaa gcc tac gac       240
Val Asn Glu Ala Asp Ala Ala Ala Leu Glu His Asp Lys Ala Tyr Asp
65                  70                  75                  80 cgg cag ctc gac agc gga gac aac ccg tac ctc aag tac aac cac gcc       288
Arg Gln Leu Asp Ser Gly Asp Asn Pro Tyr Leu Lys Tyr Asn His Ala
                85                  90                  95 gac gcg gag ttt cag gag cgc ctt aaa gaa gat acg tct ttt ggg ggc       336
Asp Ala Glu Phe Gln Glu Arg Leu Lys Glu Asp Thr Ser Phe Gly Gly
            100                 105                 110 aac ctc gga cga gca gtc ttc cag gcg aaa aag agg gtt ctt gaa cct       384
Asn Leu Gly Arg Ala Val Phe Gln Ala Lys Lys Arg Val Leu Glu Pro
        115                 120                 125 ctg ggc ctg gtt gag gaa cct gtt aag acg gct ccg gga aaa aag agg       432
Leu Gly Leu Val Glu Glu Pro Val Lys Thr Ala Pro Gly Lys Lys Arg
    130                 135                 140 ccg gta gag cac tct cct gtg gag cca gac tcc tcc tcg gga acc gga       480
```

-continued

```
Pro Val Glu His Ser Pro Val Glu Pro Asp Ser Ser Gly Thr Gly
145                 150                 155                 160 aag gcg ggc cag cag cct gca aga aaa aga ttg aat ttt ggt cag act    528
Lys Ala Gly Gln Gln Pro Ala Arg Lys Arg Leu Asn Phe Gly Gln Thr
                165                 170                 175 gga gac gca gac tca gta cct gac ccc cag cct ctc gga cag cca cca    576
Gly Asp Ala Asp Ser Val Pro Asp Pro Gln Pro Leu Gly Gln Pro Pro
            180                 185                 190 gca gcc ccc tct ggt ctg gga act aat acg atg act tca gtt aat tct    624
Ala Ala Pro Ser Gly Leu Gly Thr Asn Thr Met Thr Ser Val Asn Ser
        195                 200                 205 gca gaa gcc agc act ggt gca gga ggg ggg ggc agt aat tct gtc aaa    672
Ala Glu Ala Ser Thr Gly Ala Gly Gly Gly Gly Ser Asn Ser Val Lys
    210                 215                 220 agc atg tgg agt gag ggg gcc act ttt agt gct aac tct gta act tgt    720
Ser Met Trp Ser Glu Gly Ala Thr Phe Ser Ala Asn Ser Val Thr Cys
225                 230                 235                 240 aca ttt tcc aga cag ttt tta att cca tat gac cca gag cac cat tat    768
Thr Phe Ser Arg Gln Phe Leu Ile Pro Tyr Asp Pro Glu His His Tyr
                245                 250                 255 aag gtg ttt tct ccc gca gcg agt agc tgc cac aat gcc agt gga aag    816
Lys Val Phe Ser Pro Ala Ala Ser Ser Cys His Asn Ala Ser Gly Lys
            260                 265                 270 gag gca aag gtt tgc acc atc agt ccc ata atg gga tac tca acc cca    864
Glu Ala Lys Val Cys Thr Ile Ser Pro Ile Met Gly Tyr Ser Thr Pro
        275                 280                 285 tgg aga tat tta gat ttt aat gct tta aat tta ttt ttt tca cct tta    912
Trp Arg Tyr Leu Asp Phe Asn Ala Leu Asn Leu Phe Phe Ser Pro Leu
    290                 295                 300 gag ttt cag cac tta att gaa aat tat gga agt ata gct cct gat gct    960
Glu Phe Gln His Leu Ile Glu Asn Tyr Gly Ser Ile Ala Pro Asp Ala
305                 310                 315                 320 tta act gta acc ata tca gaa att gct gtt aag gat gtt aca gac aaa   1008
Leu Thr Val Thr Ile Ser Glu Ile Ala Val Lys Asp Val Thr Asp Lys
                325                 330                 335 act gga ggg ggg gta cag gtt act gac agc act aca ggg cgc cta tgc   1056
Thr Gly Gly Gly Val Gln Val Thr Asp Ser Thr Thr Gly Arg Leu Cys
            340                 345                 350 atg tta gta gac cat gaa tac aag tac cca tat gtg tta ggg caa ggt   1104
Met Leu Val Asp His Glu Tyr Lys Tyr Pro Tyr Val Leu Gly Gln Gly
        355                 360                 365 cag gat act tta gcc cca gaa ctt cct att tgg gta tac ttt ccc cct   1152
Gln Asp Thr Leu Ala Pro Glu Leu Pro Ile Trp Val Tyr Phe Pro Pro
    370                 375                 380 caa tat gct tac tta aca gta gga gat gtt aac aca caa gga att tct   1200
Gln Tyr Ala Tyr Leu Thr Val Gly Asp Val Asn Thr Gln Gly Ile Ser
385                 390                 395                 400 gga gac agc aaa aaa tta gca agt gaa gaa tca gca ttt tat gtt ttg   1248
Gly Asp Ser Lys Lys Leu Ala Ser Glu Glu Ser Ala Phe Tyr Val Leu
                405                 410                 415 gaa cac agt tct ttt cag ctt tta ggt aca gga ggt aca gca act atg   1296
Glu His Ser Ser Phe Gln Leu Leu Gly Thr Gly Gly Thr Ala Thr Met
            420                 425                 430 tct tat aag ttt cct cca gtg ccc cca gaa aat tta gag ggc tgc agt   1344
Ser Tyr Lys Phe Pro Pro Val Pro Pro Glu Asn Leu Glu Gly Cys Ser
        435                 440                 445 caa cac ttt tat gaa atg tac aat ccc tta tac gga tcc cgc tta ggg   1392
Gln His Phe Tyr Glu Met Tyr Asn Pro Leu Tyr Gly Ser Arg Leu Gly
    450                 455                 460
```

```
gtt cct gac aca tta gga ggt gac cca aaa ttt aga tct tta aca cat    1440
Val Pro Asp Thr Leu Gly Gly Asp Pro Lys Phe Arg Ser Leu Thr His
465                 470                 475                 480 gaa gac cat gca att cag ccc caa aac ttc atg cca ggg cca cta gta    1488
Glu Asp His Ala Ile Gln Pro Gln Asn Phe Met Pro Gly Pro Leu Val
                485                 490                 495 aac tca gtg tct aca aag gag gga gac agc tct aat act gga gct gga    1536
Asn Ser Val Ser Thr Lys Glu Gly Asp Ser Ser Asn Thr Gly Ala Gly
            500                 505                 510 aaa gcc tta aca ggc ctt agc aca ggt acc tct caa aac act aga ata    1584
Lys Ala Leu Thr Gly Leu Ser Thr Gly Thr Ser Gln Asn Thr Arg Ile
        515                 520                 525 tcc tta cgc cct ggg cca gtg tct cag cca tac cac cac tgg gac aca    1632
Ser Leu Arg Pro Gly Pro Val Ser Gln Pro Tyr His His Trp Asp Thr
    530                 535                 540 gat aaa tat gtc aca gga ata aat gcc att tct cat ggt cag acc act    1680
Asp Lys Tyr Val Thr Gly Ile Asn Ala Ile Ser His Gly Gln Thr Thr
545                 550                 555                 560 tat ggt aac gct gaa gac aaa gag tat cag caa gga gtg ggt aga ttt    1728
Tyr Gly Asn Ala Glu Asp Lys Glu Tyr Gln Gln Gly Val Gly Arg Phe
                565                 570                 575 cca aat gaa aaa gaa cag cta aaa cag tta cag ggt tta aac atg cac    1776
Pro Asn Glu Lys Glu Gln Leu Lys Gln Leu Gln Gly Leu Asn Met His
            580                 585                 590 acc tac ttt ccc aat aaa gga acc cag caa tat aca gat caa att gag    1824
Thr Tyr Phe Pro Asn Lys Gly Thr Gln Gln Tyr Thr Asp Gln Ile Glu
        595                 600                 605 cgc ccc cta atg gtg ggt tct gta tgg aac aga aga gcc ctt cac tat    1872
Arg Pro Leu Met Val Gly Ser Val Trp Asn Arg Arg Ala Leu His Tyr
    610                 615                 620 gaa agc cag ctg tgg agt aaa att cca aat tta gat gac agt ttt aaa    1920
Glu Ser Gln Leu Trp Ser Lys Ile Pro Asn Leu Asp Asp Ser Phe Lys
625                 630                 635                 640 act cag ttt gca gcc tta gga gga tgg ggt ttg cat cag cca cct cct    1968
Thr Gln Phe Ala Ala Leu Gly Gly Trp Gly Leu His Gln Pro Pro Pro
                645                 650                 655 caa ata ttt tta aaa ata tta cca caa agt ggg cca att gga ggt att    2016
Gln Ile Phe Leu Lys Ile Leu Pro Gln Ser Gly Pro Ile Gly Gly Ile
            660                 665                 670 aaa tca atg gga att act acc tta gtt cag tat gcc gtg gga att atg    2064
Lys Ser Met Gly Ile Thr Thr Leu Val Gln Tyr Ala Val Gly Ile Met
        675                 680                 685 aca gta act atg aca ttt aaa ttg ggg ccc cgt aaa gct acg gga cgg    2112
Thr Val Thr Met Thr Phe Lys Leu Gly Pro Arg Lys Ala Thr Gly Arg
    690                 695                 700 tgg aat cct caa cct gga gta tat ccc ccg cac gca gca ggt cat tta    2160
Trp Asn Pro Gln Pro Gly Val Tyr Pro Pro His Ala Ala Gly His Leu
705                 710                 715                 720 cca tat gta cta tat gac ccc aca gct aca gat gca aaa caa cac cac    2208
Pro Tyr Val Leu Tyr Asp Pro Thr Ala Thr Asp Ala Lys Gln His His
                725                 730                 735 aga cat gga tat gaa aag cct gaa gaa ttg tgg aca gcc aaa agc cgt    2256
Arg His Gly Tyr Glu Lys Pro Glu Glu Leu Trp Thr Ala Lys Ser Arg
            740                 745                 750 gtg cac cca ttg taa                                                 2271
Val His Pro Leu
        755
```

<210> SEQ ID NO 4
<211> LENGTH: 756

```
<212> TYPE: PRT
<213> ORGANISM: Adeno-associated virus
<220> FEATURE:
<221> NAME/KEY: misc_feature
<222> LOCATION: (1)..(2271)
<223> OTHER INFORMATION: B19/AAV chimeric capsid coding sequence

<400> SEQUENCE: 4
```

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Pro Val Lys Thr Ala Pro Gly Lys Lys Arg
    130                 135                 140

Pro Val Glu His Ser Pro Val Glu Pro Asp Ser Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
            180                 185                 190

Ala Ala Pro Ser Gly Leu Gly Thr Asn Thr Met Thr Ser Val Asn Ser
        195                 200                 205

Ala Glu Ala Ser Thr Gly Ala Gly Gly Gly Ser Asn Ser Val Lys
    210                 215                 220

Ser Met Trp Ser Glu Gly Ala Thr Phe Ser Ala Asn Ser Val Thr Cys
225                 230                 235                 240

Thr Phe Ser Arg Gln Phe Leu Ile Pro Tyr Asp Pro Glu His His Tyr
                245                 250                 255

Lys Val Phe Ser Pro Ala Ala Ser Ser Cys His Asn Ala Ser Gly Lys
            260                 265                 270

Glu Ala Lys Val Cys Thr Ile Ser Pro Ile Met Gly Tyr Ser Thr Pro
        275                 280                 285

Trp Arg Tyr Leu Asp Phe Asn Ala Leu Asn Leu Phe Phe Ser Pro Leu
    290                 295                 300

Glu Phe Gln His Leu Ile Glu Asn Tyr Gly Ser Ile Ala Pro Asp Ala
305                 310                 315                 320

Leu Thr Val Thr Ile Ser Glu Ile Ala Val Lys Asp Val Thr Asp Lys
                325                 330                 335

Thr Gly Gly Gly Val Gln Val Thr Asp Ser Thr Thr Gly Arg Leu Cys
            340                 345                 350

Met Leu Val Asp His Glu Tyr Lys Tyr Pro Tyr Val Leu Gly Gln Gly
        355                 360                 365

Gln Asp Thr Leu Ala Pro Glu Leu Pro Ile Trp Val Tyr Phe Pro Pro

```
                370             375             380
Gln Tyr Ala Tyr Leu Thr Val Gly Asp Val Asn Thr Gln Gly Ile Ser
385                 390                 395                 400

Gly Asp Ser Lys Lys Leu Ala Ser Glu Glu Ser Ala Phe Tyr Val Leu
                405                 410                 415

Glu His Ser Ser Phe Gln Leu Leu Gly Thr Gly Thr Ala Thr Met
            420                 425                 430

Ser Tyr Lys Phe Pro Pro Val Pro Pro Glu Asn Leu Glu Gly Cys Ser
                435                 440                 445

Gln His Phe Tyr Glu Met Tyr Asn Pro Leu Tyr Gly Ser Arg Leu Gly
            450                 455                 460

Val Pro Asp Thr Leu Gly Gly Asp Pro Lys Phe Arg Ser Leu Thr His
465                 470                 475                 480

Glu Asp His Ala Ile Gln Pro Gln Asn Phe Met Pro Gly Pro Leu Val
                485                 490                 495

Asn Ser Val Ser Thr Lys Glu Gly Asp Ser Ser Asn Thr Gly Ala Gly
                500                 505                 510

Lys Ala Leu Thr Gly Leu Ser Thr Gly Thr Ser Gln Asn Thr Arg Ile
                515                 520                 525

Ser Leu Arg Pro Gly Pro Val Ser Gln Pro Tyr His His Trp Asp Thr
530                 535                 540

Asp Lys Tyr Val Thr Gly Ile Asn Ala Ile Ser His Gly Gln Thr Thr
545                 550                 555                 560

Tyr Gly Asn Ala Glu Asp Lys Glu Tyr Gln Gln Gly Val Gly Arg Phe
                565                 570                 575

Pro Asn Glu Lys Glu Gln Leu Lys Gln Leu Gln Gly Leu Asn Met His
                580                 585                 590

Thr Tyr Phe Pro Asn Lys Gly Thr Gln Gln Tyr Thr Asp Gln Ile Glu
                595                 600                 605

Arg Pro Leu Met Val Gly Ser Val Trp Asn Arg Arg Ala Leu His Tyr
610                 615                 620

Glu Ser Gln Leu Trp Ser Lys Ile Pro Asn Leu Asp Asp Ser Phe Lys
625                 630                 635                 640

Thr Gln Phe Ala Ala Leu Gly Gly Trp Gly Leu His Gln Pro Pro Pro
                645                 650                 655

Gln Ile Phe Leu Lys Ile Leu Pro Gln Ser Gly Pro Ile Gly Gly Ile
                660                 665                 670

Lys Ser Met Gly Ile Thr Thr Leu Val Gln Tyr Ala Val Gly Ile Met
                675                 680                 685

Thr Val Thr Met Thr Phe Lys Leu Gly Pro Arg Lys Ala Thr Gly Arg
                690                 695                 700

Trp Asn Pro Gln Pro Gly Val Tyr Pro Pro His Ala Ala Gly His Leu
705                 710                 715                 720

Pro Tyr Val Leu Tyr Asp Pro Thr Ala Thr Asp Ala Lys Gln His His
                725                 730                 735

Arg His Gly Tyr Glu Lys Pro Glu Glu Leu Trp Thr Ala Lys Ser Arg
                740                 745                 750

Val His Pro Leu
        755

<210> SEQ ID NO 5
<211> LENGTH: 8179
<212> TYPE: DNA
<213> ORGANISM: Adeno-associated virus
```

<400> SEQUENCE: 5

```
aattcccatc atcaataata taccttattt tggattgaag ccaatatgat aatgaggggg      60
tggagtttgt gacgtggcgc ggggcgtggg aacggggcgg gtgacgtagt agtctctaga     120
gtcctgtatt agaggtcacg tgagtgtttt gcgacatttt gcgacaccat gtggtcacgc     180
tgggtattta agcccgagtg agcacgcagg gtctccattt tgaagcggga ggtttgaacg     240
cgcagccgcc atgccggggt tttacgagat tgtgattaag gtccccagcg accttgacgg     300
gcatctgccc ggcatttctg acagctttgt gaactgggtg gccgagaagg aatgggagtt     360
gccgccagat tctgacatgg atctgaatct gattgagcag gcacccctga ccgtggccga     420
gaagctgcag cgcgactttc tgacggaatg gcgccgtgtg agtaaggccc ggaggccct      480
tttctttgtg caatttgaga agggagagag ctacttccac atgcacgtgc tcgtggaaac     540
caccggggtg aaatccatgg ttttgggacg tttcctgagt cagattcgcg aaaaactgat     600
tcagagaatt taccgcggga tcgagccgac tttgccaaac tggttcgcgg tcacaaagac     660
cagaaatggc gccggaggcg ggaacaaggt ggtggatgag tgctacatcc ccaattactt     720
gctccccaaa acccagcctg agctccagtg ggcgtggact aatatggaac agtatttaag     780
cgcctgtttg aatctcacgg agcgtaaacg gttggtggcg cagcatctga cgcacgtgtc     840
gcagacgcag gagcagaaca aagagaatca gaatcccaat tctgatgcgc cggtgatcag     900
atcaaaaact tcagccaggt acatggagct ggtcggtgg ctcgtggaca agggattac      960
ctcggagaag cagtggatcc aggaggacca ggcctcatac atctccttca atgcggcctc    1020
caactcgcgg tcccaaatca aggctgcctt ggacaatgcg ggaaagatta tgagcctgac    1080
taaaaccgcc cccgactacc tggtgggcca gcagcccgtg gaggacattt ccagcaatcg    1140
gatttataaa attttggaac taaacgggta cgatccccaa tatgcggctt ccgtctttct    1200
gggatgggcc acgaaaaagt tcggcaagag gaacaccatc tggctgtttg ggcctgcaac    1260
taccgggaag accaacatcg cggaggccat agcccacact gtgcccttct acgggtgcgt    1320
aaactggacc aatgagaact ttcccttcaa cgactgtgtc gacaagatgg tgatctggtg    1380
ggaggagggg aagatgaccg ccaaggtcgt ggagtcggcc aaagccattc tcggaggaag    1440
caaggtgcgc gtggaccaga atgcaagtc ctcggcccag atagacccga ctcccgtgat    1500
cgtcacctcc aacaccaaca tgtgcgccgt gattgacggg aactcaacga ccttcgaaca    1560
ccagcagccg ttgcaagacc ggatgttcaa atttgaactc acccgccgtc tggatcatga    1620
ctttgggaag gtcaccaagc aggaagtcaa agactttttc cggtgggcaa aggatcacgt    1680
ggttgaggtg gagcatgaat tctacgtcaa aaagggtgga gccaagaaaa gacccgcccc    1740
cagtgacgca gatataagtg agcccaaacg ggtgcgcgag tcagttgcgc agccatcgac    1800
gtcagacgcg gaagcttcga tcaactacgc agacaggtac caaaacaaat gttctcgtca    1860
cgtgggcatg aatctgatgc tgtttccctg cagacaatgc gagagaatga atcagaattc    1920
aaatatctgc ttcactcacg gacagaaaga ctgtttagag tgctttcccg tgtcagaatc    1980
tcaacccgtt tctgtcgtca aaaggcgta tcagaaactg tgctacattc atcatatcat    2040
gggaaaggtg ccagacgctt gcactgcctg cgatctggtc aatgtggatt tggatgactg    2100
catctttgaa caataaatga tttaaatcag gtatggctgc cgatggttat cttccagatt    2160
ggctcgagga cactctctct gaaggaataa gacagtggtg gaagctcaaa cctggcccac    2220
caccaccaaa gcccgcagag cggcataagg acgacagcag gggtcttgtg cttcctgggt    2280
```

```
acaagtacct cggacccttc aacggactcg acaagggaga gccggtcaac gaggcagacg    2340
ccgcggccct cgagcacgac aaagcctacg accggcagct cgacagcgga gacaacccgt    2400
acctcaagta caaccacgcc gacgcggagt tcaggagcg ccttaaagaa gatacgtctt     2460
ttgggggcaa cctcggacga gcagtcttcc aggcgaaaaa gagggttctt gaacctctgg    2520
gcctggttga ggaacctgtt aagacggctc cgggaaaaaa gaggccggta gagcactctc    2580
ctgtggagcc agactcctcc tcgggaaccg gaaaggcggg ccagcagcct gcaagaaaaa    2640
gattgaattt tggtcagact ggagacgcag actcagtacc tgaccccag cctctcggac     2700 agccaccagc agcccctct ggtctgggaa ctaaatacgat ggctacaggc agtggcgcac    2760
caatggcaga caataacgag ggcgccgacg gagtgggtaa ttcctccgga aattggcatt    2820
gcgattccac atggatgggc gacagagtca tcaccaccag cacccgaacc tgggccctgc    2880
ccacctacaa caaccacctc tacaaacaaa tttccagcca atcaggagcc tcgaacgaca    2940
atcactactt tggctacagc accccttggg ggtattttga cttcaacaga ttccactgcc    3000
acttttcacc acgtgactgg caaagactca tcaacaacaa ctggggattc cgacccaaga    3060
gactcaactt caagctcttt aacattcaag tcaaagaggt cacgcagaat gacggtacga    3120
cgacgattgc caataaccctt accagcacgg ttcaggtgtt tactgactcg gagtaccagc    3180
tcccgtacgt gctcgggtcg gcgcaccaag gctgtctccc gccgtttcca gcggacgtct    3240
tcatggtccc tcagtatgga tacctcaccc tgaacaacgg aagtcaagcg gtgggacgct    3300 catccttta ctgcctggag tacttcccctt cgcagatgct aaggactgga ataacttcc     3360 aattcagcta taccttcgag gatgtacctt ttcacagcag ctacgctcac agccagagtt    3420
tggatcgctt gatgaatcct cttattgatc agtatctgta ctacctgaac agaacgcaag    3480
gaacaacctc tggaacaacc aaccaatcac ggctgctttt tagccaggct gggcctcagt    3540
ctatgtcttt gcaggccaga aattggctac ctgggccctg ctaccggcaa cagagacttt    3600
caaagactgc taacgacaac aacaacagta actttccttg gacagcggcc agcaaatatc    3660
atctcaatgg ccgcgactcg ctggtgaatc caggaccagc tatggccagt cacaaggacg    3720
atgaagaaaa atttttccct atgcacggca atctaatatt tggcaaagaa gggacaacgg    3780
caagtaacgc agaattagat aatgtaatga ttacgatga agaagagatt cgtaccacca    3840
atcctgtggc aacagagcag tatggaactg tggcaaataa cttgcagagc tcaaatacag    3900
ctcccacgac tggaactgtc aatcatcagg gggccttacc tggcatggtg tggcaagatc    3960
gtgacgtgta ccttcaagga cctatctggg caaagattcc tcacacggat ggacactttc    4020
atccttctcc tctgatggga ggctttggac tgaaacatcc gcctcctcaa atcatgatca    4080
aaaatactcc ggtacctgcg aatccttcga ccaccttcag tgcggcaaag tttgcttcct    4140
tcatcacaca gtactccacg ggacaggtca gcgtggagat cgagtgggag ctgcagaagg    4200
aaaacagcaa acgctggaat cccgaaattc agtacacttc caactacaac aagtctgtta    4260
atcgtggact taccgtggat actaatggcg tgtattcaga gcctcgcccc attggcacca    4320
gatacctgac tcgtaatctg taattgcttg ttaatcaata aaccgtttaa ttcgtttcag    4380
ttgaactttg gtctctgcgt atttctttct tatctagttt ccatgctcta gactactacg    4440
tcacccgccc cgttcccacg ccccgcgcca cgtcacaaac tccacccct cattatcata     4500 ttggcttcaa tccaaaataa ggtatattat tgatgatgca tcgctggcgt aatagcgaag    4560
aggcccgcac cgatcgccct tcccaacagt tgcgcagcct gaatggcgaa tggaattcca    4620
gacgattgag cgtcaaaatg taggtatttc catgagcgtt tttcctgttg caatggctgg    4680
```

```
cggtaatatt gttctggata ttaccagcaa ggccgatagt ttgagttctt ctactcaggc   4740
aagtgatgtt attactaatc aaagaagtat tgcgacaacg gttaatttgc gtgatggaca   4800
gactctttta ctcggtggcc tcactgatta taaaaacact tctcaggatt ctggcgtacc   4860
gttcctgtct aaaatccctt taatcggcct cctgtttagc tcccgctctg attctaacga   4920
ggaaagcacg ttatacgtgc tcgtcaaagc aaccatagta cgcgccctgt agcggcgcat   4980
taagcgcggc gggtgtggtg gttacgcgca gcgtgaccgc tacacttgcc agcgccctag   5040
cgcccgctcc tttcgctttc ttcccttcct tctcgccac gttcgccggc tttccccgtc   5100
aagctctaaa tcggggctc cctttagggt tccgatttag tgctttacgg cacctcgacc   5160
ccaaaaaact tgattagggt gatggttcac gtagtgggcc atcgccctga tagacggttt   5220
ttcgcccttt gacgttggag tccacgttct ttaatagtgg actcttgttc caaactggaa   5280
caacactcaa ccctatctcg gtctattctt tgatttata agggattttg ccgatttcgg   5340
cctattggtt aaaaaatgag ctgatttaac aaaaatttaa cgcgaatttt aacaaaatat   5400
taacgtttac aatttaaata tttgcttata caatcttcct gttttgggg cttttctgat   5460 tatcaaccgg ggtacatatg attgacatgc tagttttacg attaccgttc atcgattctc   5520
ttgtttgctc cagactctca ggcaatgacc tgatagcctt tgtagagacc tctcaaaaat   5580
agctaccctc tccggcatga atttatcagc tagaacggtt gaatatcata ttgatggtga   5640
tttgactgtc tccggccttt ctcacccgtt tgaatcttta cctacacatt actcaggcat   5700
tgcatttaaa atatatgagg gttctaaaaa tttttatcct tgcgttgaaa taaggcttc   5760 tcccgcaaaa gtattacagg gtcataatgt ttttggtaca accgatttag ctttatgctc   5820
tgaggcttta ttgcttaatt ttgctaattc tttgccttgc ctgtatgatt tattggatgt   5880
tggaattcct gatgcggtat tttctcctta cgcatctgtg cggtatttca caccgcatat   5940
ggtgcactct cagtacaatc tgctctgatg ccgcatagtt aagccagccc cgacacccgc   6000
caacacccgc tgacgcgccc tgacgggctt gtctgctccc ggcatccgct tacagacaag   6060
ctgtgaccgt ctccgggagc tgcatgtgtc agaggttttc accgtcatca ccgaaacgcg   6120
cgagacgaaa gggcctcgtg atacgcctat ttttataggt taatgtcatg ataataatgg   6180
tttcttagac gtcaggtggc acttttcggg gaaatgtgcg cggaacccct atttgtttat   6240
ttttctaaat acattcaaat atgtatccgc tcatgagaca ataaccctga taaatgcttc   6300
aataatattg aaaaggaag agtatgagta ttcaacattt ccgtgtcgcc cttattccct   6360 ttttgcggc attttgcctt cctgtttttg ctcacccaga aacgctggtg aaagtaaaag   6420
atgctgaaga tcagttgggt gcacgagtgg gttacatcga actggatctc aacagcggta   6480
agatccttga gagttttcgc cccgaagaac gttttccaat gatgagcact tttaaagttc   6540
tgctatgtgg cgcggtatta tcccgtattg acgccgggca agagcaactc ggtcgccgca   6600
tacactattc tcagaatgac ttggttgagt actcaccagt cacagaaaag catcttacgg   6660
atggcatgac agtaagagaa ttatgcagtg ctgccataac catgagtgat aacactgcgg   6720
ccaacttact tctgacaacg atcggaggac cgaaggagct aaccgctttt ttgcacaaca   6780
tgggggatca tgtaactcgc cttgatcgtt gggaaccgga gctgaatgaa gccataccaa   6840
acgacgagcg tgacaccacg atgcctgtag caatggcaac aacgttgcgc aaactattaa   6900
ctggcgaact acttactcta gcttcccggc aacaattaat agactggatg gaggcggata   6960
aagttgcagg accacttctg cgctcggccc ttccggctgg ctggtttatt gctgataaat   7020
```

```
ctggagccgg tgagcgtggg tctcgcggta tcattgcagc actggggcca gatggtaagc      7080
cctcccgtat cgtagttatc tacacgacgg ggagtcaggc aactatggat gaacgaaata      7140
gacagatcgc tgagataggt gcctcactga ttaagcattg gtaactgtca gaccaagttt      7200
actcatatat actttagatt gatttaaaac ttcatttta atttaaaagg atctaggtga      7260
agatcctttt tgataatctc atgaccaaaa tcccttaacg tgagttttcg ttccactgag      7320
cgtcagaccc cgtagaaaag atcaaaggat cttcttgaga tccttttttt ctgcgcgtaa      7380
tctgctgctt gcaaacaaaa aaaccaccgc taccagcggt ggtttgtttg ccggatcaag      7440
agctaccaac tctttttccg aaggtaactg gcttcagcag agcgcagata ccaaatactg      7500
tccttctagt gtagccgtag ttaggccacc acttcaagaa ctctgtagca ccgcctacat      7560
acctcgctct gctaatcctg ttaccagtgg ctgctgccag tggcgataag tcgtgtctta      7620
ccgggttgga ctcaagacga tagttaccgg ataaggcgca gcggtcgggc tgaacggggg      7680
gttcgtgcac acagcccagc ttggagcgaa cgacctacac cgaactgaga tacctacagc      7740
gtgagctatg agaaagcgcc acgcttcccg aagggagaaa ggcggacagg tatccggtaa      7800
gcggcagggt cggaacagga gagcgcacga gggagcttcc agggggaaac gcctggtatc      7860
tttatagtcc tgtcgggttt cgccacctct gacttgagcg tcgatttttg tgatgctcgt      7920
caggggggcg gagcctatgg aaaaacgcca gcaacgcggc ctttttacgg ttcctggcct      7980
tttgctggcc ttttgctcac atgttctttc ctgcgttatc ccctgattct gtggataacc      8040
gtattaccgc ctttgagtga gctgataccg ctcgccgcag ccgaacgacc gagcgcagcg      8100
agtcagtgag cgaggaagcg gaagagcgcc caatacgcaa accgcctctc cccgcgcgtt      8160
ggccgattca ttaatgcag                                                 8179

<210> SEQ ID NO 6
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 6
aattcgccgg cgatatc                                                    17

<210> SEQ ID NO 7
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 7
tcgagatatc gccggc                                                     16

<210> SEQ ID NO 8
<211> LENGTH: 12
<212> TYPE: DNA
<213> ORGANISM: Artificial sequence
<220> FEATURE:
<223> OTHER INFORMATION: Synthetic oligonucleotide

<400> SEQUENCE: 8
ggcgatatcg cc                                                         12

<210> SEQ ID NO 9
<211> LENGTH: 48
```

<212> TYPE: DNA
<213> ORGANISM: Artificial sequence
<220> FEATURE:
<223> OTHER INFORMATION: Synthetic oligonucleotide

<400> SEQUENCE: 9
gctagcggcg gacaccatca ccaccaccat caccacggcg gaagcgct            48

<210> SEQ ID NO 10
<211> LENGTH: 48
<212> TYPE: DNA
<213> ORGANISM: Artificial sequence
<220> FEATURE:
<223> OTHER INFORMATION: Synthetic oligonucleotide

<400> SEQUENCE: 10
agcgcttccg ccgtggtgat ggtggtggtg atggtgtccg ccgctagc            48

<210> SEQ ID NO 11
<211> LENGTH: 51
<212> TYPE: DNA
<213> ORGANISM: Artificial sequence
<220> FEATURE:
<223> OTHER INFORMATION: Synthetic oligonucleotide

<400> SEQUENCE: 11
acgctagcgg cggacaccat caccaccacc atcaccacgg cggaagcgct t         51

<210> SEQ ID NO 12
<211> LENGTH: 51
<212> TYPE: DNA
<213> ORGANISM: Artificial sequence
<220> FEATURE:
<223> OTHER INFORMATION: Synthetic oligonucleotide

<400> SEQUENCE: 12
aagcgcttcc gccgtggtga tggtggtggt gatggtgtcc gccgctagcg t         51

<210> SEQ ID NO 13
<211> LENGTH: 51
<212> TYPE: DNA
<213> ORGANISM: Artificial sequence
<220> FEATURE:
<223> OTHER INFORMATION: Synthetic oligonucleotide

<400> SEQUENCE: 13
gggttccgga gggcaccacc atcaccacca ccatcacgga ggcgccagcg a         51

<210> SEQ ID NO 14
<211> LENGTH: 51
<212> TYPE: DNA
<213> ORGANISM: Artificial sequence
<220> FEATURE:
<223> OTHER INFORMATION: Synthetic oligonucleotide

<400> SEQUENCE: 14
tcgctggcgc ctccgtgatg gtggtggtga tggtggtgcc ctccggaacc c         51

<210> SEQ ID NO 15
<211> LENGTH: 60
<212> TYPE: DNA
<213> ORGANISM: Artificial sequence
<220> FEATURE:
<223> OTHER INFORMATION: Synthetic oligonucleotide

<400> SEQUENCE: 15

```
gccggatccg gcggcggctc cagaccccccc ggcttcagcc ccttcagatc cggcggcgcc        60
```

<210> SEQ ID NO 16
<211> LENGTH: 60
<212> TYPE: DNA
<213> ORGANISM: Artificial sequence
<220> FEATURE:
<223> OTHER INFORMATION: Synthetic oligonucleotide

<400> SEQUENCE: 16

```
ggcgccgccg gatctgaagg ggctgaagcc ggggggtctg gagccgccgc cggatccggc        60
```

<210> SEQ ID NO 17
<211> LENGTH: 69
<212> TYPE: DNA
<213> ORGANISM: Artificial sequence
<220> FEATURE:
<223> OTHER INFORMATION: Synthetic oligonucleotide

<400> SEQUENCE: 17

```
gaggttcatg tgactgcggg ggaagacccc ctggcttcag cccattcaga ggtggctgct        60
tctgtggcg                                                                69
```

<210> SEQ ID NO 18
<211> LENGTH: 69
<212> TYPE: DNA
<213> ORGANISM: Artificial sequence
<220> FEATURE:
<223> OTHER INFORMATION: Synthetic oligonucleotide

<400> SEQUENCE: 18

```
cgccacagaa gcagccacct ctgaatgggc tgaagccagg gggtcttccc ccgcagtcac        60
atgaacctc                                                                69
```

<210> SEQ ID NO 19
<211> LENGTH: 69
<212> TYPE: DNA
<213> ORGANISM: Artificial sequence
<220> FEATURE:
<223> OTHER INFORMATION: Synthetic oligonucleotide

<400> SEQUENCE: 19

```
aggttcatgt gactgcgggg aagaccccc tggcttcagc ccattcagag gtggctgctt        60
ctgtggcgg                                                                69
```

<210> SEQ ID NO 20
<211> LENGTH: 69
<212> TYPE: DNA
<213> ORGANISM: Artificial sequence
<220> FEATURE:
<223> OTHER INFORMATION: Synthetic oligonucleotide

<400> SEQUENCE: 20

```
ccgccacaga agcagccacc tctgaatggg ctgaagccag gggtcttcc cccgcagtca        60
catgaacct                                                                69
```

<210> SEQ ID NO 21
<211> LENGTH: 36
<212> TYPE: DNA
<213> ORGANISM: Artificial sequence
<220> FEATURE:
<223> OTHER INFORMATION: Synthetic oligonucleotide

<400> SEQUENCE: 21

```
ggatcctgcg actgcagggg cgattgtttc tgcggc                         36

<210> SEQ ID NO 22
<211> LENGTH: 36
<212> TYPE: DNA
<213> ORGANISM: Artificial sequence
<220> FEATURE:
<223> OTHER INFORMATION: Synthetic oligonucleotide

<400> SEQUENCE: 22
gccgcagaaa caatcgcccc tgcagtcgca ggatcc                         36

<210> SEQ ID NO 23
<211> LENGTH: 36
<212> TYPE: DNA
<213> ORGANISM: Artificial sequence
<220> FEATURE:
<223> OTHER INFORMATION: Synthetic oligonucleotide

<400> SEQUENCE: 23
gatcctcgga ctgcaggggc gattgtttct gcggcg                         36

<210> SEQ ID NO 24
<211> LENGTH: 36
<212> TYPE: DNA
<213> ORGANISM: Artificial sequence
<220> FEATURE:
<223> OTHER INFORMATION: Synthetic oligonucleotide

<400> SEQUENCE: 24
cgccgcagaa acaatcgccc ctgcagtcgc aggatc                         36

<210> SEQ ID NO 25
<211> LENGTH: 36
<212> TYPE: DNA
<213> ORGANISM: Artificial sequence
<220> FEATURE:
<223> OTHER INFORMATION: Synthetic oligonucleotide

<400> SEQUENCE: 25
aggatcctgc gactgcaggg gcgattgttt ctgcgg                         36

<210> SEQ ID NO 26
<211> LENGTH: 36
<212> TYPE: DNA
<213> ORGANISM: Artificial sequence
<220> FEATURE:
<223> OTHER INFORMATION: Synthetic oligonucleotide

<400> SEQUENCE: 26
ccgcagaaac aatcgcccct gcagtcgcag gatcct                         36

<210> SEQ ID NO 27
<211> LENGTH: 63
<212> TYPE: DNA
<213> ORGANISM: Artificial sequence
<220> FEATURE:
<223> OTHER INFORMATION: Synthetic oligonucleotide

<400> SEQUENCE: 27
aggttcatgt gactgcgggg gaaagaagaa gaagaagaag aagggcggct gcttctgtgg   60
cgg                                                             63

<210> SEQ ID NO 28
```

<211> LENGTH: 63
<212> TYPE: DNA
<213> ORGANISM: Artificial sequence
<220> FEATURE:
<223> OTHER INFORMATION: Synthetic oligonucleotide

<400> SEQUENCE: 28
ccgccacaga agcagccgcc cttcttcttc ttcttcttct ttcccccgca gtcacatgaa    60
cct    63

<210> SEQ ID NO 29
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 29
tgccgagcca tcgacgtcag acgcg    25

<210> SEQ ID NO 30
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 30
gcagatgtta acacacaagg cgttcttcca    30

<210> SEQ ID NO 31
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 31
ttgtgtgtta acatctgcgg tagctgcttg    30

<210> SEQ ID NO 32
<211> LENGTH: 29
<212> TYPE: DNA
<213> ORGANISM: Artificial sequence
<220> FEATURE:
<223> OTHER INFORMATION: Synthetic oligonucleotide

<400> SEQUENCE: 32
cagagagtta acagacaagc agctaccgc    29

<210> SEQ ID NO 33
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 33
gtctgttaac tctctggagg ttggtagata    30

<210> SEQ ID NO 34
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 34
acaaatgtta acattgaaaa ggtcatgatt                                           30

<210> SEQ ID NO 35
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 35
ttcaatgtta acatttgttt tctctgagcc                                           30

<210> SEQ ID NO 36
<211> LENGTH: 28
<212> TYPE: DNA
<213> ORGANISM: Artificial sequence
<220> FEATURE:
<223> OTHER INFORMATION: Synthetic oligonucleotide

<400> SEQUENCE: 36
ggacgatatc gaaaagtttt ttcctcag                                             28

<210> SEQ ID NO 37
<211> LENGTH: 28
<212> TYPE: DNA
<213> ORGANISM: Artificial sequence
<220> FEATURE:
<223> OTHER INFORMATION: Synthetic oligonucleotide

<400> SEQUENCE: 37
acttttcgat atcgtccttg tggcttgc                                             28

<210> SEQ ID NO 38
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 38
tctctggtta acccgggccc ggccatggca                                           30

<210> SEQ ID NO 39
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 39
gcccgggtta accagagagt ctctgccatt                                           30

<210> SEQ ID NO 40
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 40
tgcgcagcca tcgacgtcag acgcg                                                25

<210> SEQ ID NO 41

<210> SEQ ID NO 41
<211> LENGTH: 31
<212> TYPE: DNA
<213> ORGANISM: Artificial sequence
<220> FEATURE:
<223> OTHER INFORMATION: Synthetic oligonucleotide

<400> SEQUENCE: 41
catgatgcat caaagttcaa ctgaaacgaa t                                    31

<210> SEQ ID NO 42
<211> LENGTH: 42
<212> TYPE: DNA
<213> ORGANISM: Artificial sequence
<220> FEATURE:
<223> OTHER INFORMATION: Synthetic oligonucleotide

<400> SEQUENCE: 42
gatacttaag atctagtgga accaccacgc actcaaaggc tt                        42

<210> SEQ ID NO 43
<211> LENGTH: 42
<212> TYPE: DNA
<213> ORGANISM: Artificial sequence
<220> FEATURE:
<223> OTHER INFORMATION: Synthetic oligonucleotide

<400> SEQUENCE: 43
ctagcttaag catgcataca ggtactggtc gatgagagga tt                        42

<210> SEQ ID NO 44
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 44
tgccgagcca tcgacgtcag acgcg                                           25

<210> SEQ ID NO 45
<211> LENGTH: 31
<212> TYPE: DNA
<213> ORGANISM: Artificial sequence
<220> FEATURE:
<223> OTHER INFORMATION: Synthetic oligonucleotide

<400> SEQUENCE: 45
catgatgcat caaagttcaa ctgaaacgaa t                                    31

<210> SEQ ID NO 46
<211> LENGTH: 33
<212> TYPE: DNA
<213> ORGANISM: Artificial sequence
<220> FEATURE:
<223> OTHER INFORMATION: Synthetic oligonucleotide

<400> SEQUENCE: 46
cgagctcttc gatggctaca ggcagtggcg cac                                  33

<210> SEQ ID NO 47
<211> LENGTH: 36
<212> TYPE: DNA
<213> ORGANISM: Artificial sequence
<220> FEATURE:
<223> OTHER INFORMATION: Synthetic oligonucleotide

<400> SEQUENCE: 47
agcgctcttc ccatcgtatt agttcccaga ccagag        36

<210> SEQ ID NO 48
<211> LENGTH: 33
<212> TYPE: DNA
<213> ORGANISM: Artificial sequence
<220> FEATURE:
<223> OTHER INFORMATION: Synthetic oligonucleotide

<400> SEQUENCE: 48
cgagctcttc gacggctccg ggaaaaaaga ggc        33

<210> SEQ ID NO 49
<211> LENGTH: 36
<212> TYPE: DNA
<213> ORGANISM: Artificial sequence
<220> FEATURE:
<223> OTHER INFORMATION: Synthetic oligonucleotide

<400> SEQUENCE: 49
agcgctcttc ccgtcttaac aggttcctca accagg        36

<210> SEQ ID NO 50
<211> LENGTH: 36
<212> TYPE: DNA
<213> ORGANISM: Artificial sequence
<220> FEATURE:
<223> OTHER INFORMATION: Synthetic oligonucleotide

<400> SEQUENCE: 50
cgagctcttc gatgcgtgca gcagctggag gagctg        36

<210> SEQ ID NO 51
<211> LENGTH: 36
<212> TYPE: DNA
<213> ORGANISM: Artificial sequence
<220> FEATURE:
<223> OTHER INFORMATION: Synthetic oligonucleotide

<400> SEQUENCE: 51
agcgctcttc gcatctcact gtcatcagac gagtcg        36

<210> SEQ ID NO 52
<211> LENGTH: 33
<212> TYPE: DNA
<213> ORGANISM: Artificial sequence
<220> FEATURE:
<223> OTHER INFORMATION: Synthetic oligonucleotide

<400> SEQUENCE: 52
cgagctcttc gacggctcct ggaaagaaga gac        33

<210> SEQ ID NO 53
<211> LENGTH: 36
<212> TYPE: DNA
<213> ORGANISM: Artificial sequence
<220> FEATURE:
<223> OTHER INFORMATION: Synthetic oligonucleotide

<400> SEQUENCE: 53
agcgctcttc ccgtctcacc cgcttgctca accaga        36

<210> SEQ ID NO 54
<211> LENGTH: 36
<212> TYPE: DNA

```
<213> ORGANISM: Artificial sequence
<220> FEATURE:
<223> OTHER INFORMATION: Synthetic oligonucleotide

<400> SEQUENCE: 54
agttactctt ccatgacttc agttaattct gcagaa                                  36

<210> SEQ ID NO 55
<211> LENGTH: 36
<212> TYPE: DNA
<213> ORGANISM: Artificial sequence
<220> FEATURE:
<223> OTHER INFORMATION: Synthetic oligonucleotide

<400> SEQUENCE: 55
agttactctt ctttacaatg ggtgcacacg gctttt                                  36

<210> SEQ ID NO 56
<211> LENGTH: 36
<212> TYPE: DNA
<213> ORGANISM: Artificial sequence
<220> FEATURE:
<223> OTHER INFORMATION: Synthetic oligonucleotide

<400> SEQUENCE: 56
agttactctt cttaatcgtg gacttaccgt ggatac                                  36

<210> SEQ ID NO 57
<211> LENGTH: 36
<212> TYPE: DNA
<213> ORGANISM: Artificial sequence
<220> FEATURE:
<223> OTHER INFORMATION: Synthetic oligonucleotide

<400> SEQUENCE: 57
agttactctt cccatcgtat tagttcccag accaga                                  36

<210> SEQ ID NO 58
<211> LENGTH: 29
<212> TYPE: DNA
<213> ORGANISM: Artificial sequence
<220> FEATURE:
<223> OTHER INFORMATION: Synthetic oligonucleotide

<400> SEQUENCE: 58
aagcgccgcg gccgctgctt atgtacgca                                          29

<210> SEQ ID NO 59
<211> LENGTH: 27
<212> TYPE: DNA
<213> ORGANISM: Artificial sequence
<220> FEATURE:
<223> OTHER INFORMATION: Synthetic oligonucleotide

<400> SEQUENCE: 59
gacgcggaag cttcggtgga ctacgcg                                            27
```